United States Patent
Hanes et al.

(10) Patent No.: US 11,007,279 B2
(45) Date of Patent: May 18, 2021

(54) HIGHLY STABLE BIODEGRADABLE GENE VECTOR PLATFORMS FOR OVERCOMING BIOLOGICAL BARRIERS

(71) Applicant: The Johns Hopkins University, Baltimore, MD (US)

(72) Inventors: Justin Hanes, Baltimore, MD (US); Jung Soo Suk, Baltimore, MD (US); Panagiotis Mastorakos, Charlottesville, VA (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 0 days.

(21) Appl. No.: 16/431,507

(22) Filed: Jun. 4, 2019

(65) Prior Publication Data

US 2019/0321488 A1 Oct. 24, 2019

Related U.S. Application Data

(62) Division of application No. 15/310,643, filed as application No. PCT/US2015/030397 on May 12, 2015, now Pat. No. 10,335,500.

(60) Provisional application No. 61/991,946, filed on May 12, 2014, provisional application No. 62/001,884, filed on May 22, 2014.

(51) Int. Cl.
| | |
|---|---|
| *A61K 48/00* | (2006.01) |
| *A61K 47/60* | (2017.01) |
| *A61K 47/59* | (2017.01) |
| *A61K 47/69* | (2017.01) |
| *A61K 9/00* | (2006.01) |
| *C12N 15/88* | (2006.01) |
| *A61K 9/51* | (2006.01) |

(52) U.S. Cl.
CPC .......... *A61K 48/005* (2013.01); *A61K 9/0043* (2013.01); *A61K 9/0085* (2013.01); *A61K 9/5153* (2013.01); *A61K 47/593* (2017.08); *A61K 47/60* (2017.08); *A61K 47/6935* (2017.08); *A61K 48/00* (2013.01); *A61K 48/0041* (2013.01); *C12N 15/88* (2013.01)

(58) Field of Classification Search
CPC .. A61K 47/60; A61K 47/593; A61K 48/0041; A61K 48/005
See application file for complete search history.

(56) References Cited

U.S. PATENT DOCUMENTS

| | | | |
|---|---|---|---|
| 6,531,128 | B1 | 3/2003 | Wax |
| 9,327,037 | B2 | 5/2016 | Suk |
| 9,415,020 | B2 | 8/2016 | Ensign |
| 9,629,813 | B2 | 4/2017 | Ensign |
| 9,675,711 | B2 | 6/2017 | Suk |
| 9,889,208 | B2 | 2/2018 | Hanes |
| 9,937,130 | B2 | 4/2018 | Mcdonnell |
| 2003/0118550 | A1 | 6/2003 | Kabanov |
| 2003/0180366 | A1 | 9/2003 | Kirschner |
| 2005/0176945 | A1 | 8/2005 | Mount, Jr. |
| 2006/0276473 | A1 | 12/2006 | Bostion |
| 2007/0111959 | A1 | 5/2007 | Yockman |
| 2007/0292475 | A1 | 12/2007 | Campbell |
| 2008/0166414 | A1 | 7/2008 | Hanes |
| 2010/0068285 | A1 | 3/2010 | Zale |
| 2010/0160252 | A1 | 6/2010 | Chetoni |
| 2010/0166865 | A1 | 7/2010 | Kumar |
| 2010/0196492 | A1 | 8/2010 | Green |
| 2010/0215580 | A1 | 8/2010 | Hanes |
| 2011/0165074 | A1 | 7/2011 | Gruell |
| 2012/0083037 | A1 | 4/2012 | Wendorff |
| 2012/0121718 | A1 | 5/2012 | Lai |
| 2012/0149630 | A1 | 6/2012 | Zugates |
| 2012/0225129 | A1* | 9/2012 | Eliasof ............... A61P 9/10 424/499 |
| 2013/0101672 | A1 | 4/2013 | Cheng |
| 2013/0183244 | A1 | 7/2013 | Hanes |
| 2013/0236556 | A1 | 9/2013 | Lai |
| 2013/0256868 | A1 | 10/2013 | Aliyev |

(Continued)

FOREIGN PATENT DOCUMENTS

| | | |
|---|---|---|
| CA | 2559208 | 9/2005 |
| CN | 101797232 | 8/2010 |

(Continued)

OTHER PUBLICATIONS

Kim et al (Intech Open Science, 2013, Chapter 15, pp. 375-396) (Year: 2013).*
Akinc and Langer, "Measuring the pH environment of DNA delivered using nonviral vectors: implications for lysosomal trafficking", Biotechnol Bioeng, 78(5):503-8 (2002).
Akinc, et al., "Synthesis of poly(beta-amino ester)s optimized for highly effective gene delivery", Bioconjug Chem, 14(5):979-88 (2003).
Akinc, et al., "Exploring polyethylenimine-mediated DNA transfection and the proton sponge hypothesis", J Gene Med, 7(5):657-63 (2005).
Anderson, et al., "Semi-automated synthesis and screening of a large library of degradable cationic polymers for gene delivery", Angew Chem Int Ed Engl, 42(27): 3153-8 (2003).

(Continued)

*Primary Examiner* — Mark V Stevens
(74) *Attorney, Agent, or Firm* — Pabst Patent Group LLP

(57) ABSTRACT

A major challenge in non-viral gene delivery remains finding a safe and effective delivery system. Colloidally stable non-viral gene vector delivery systems capable of overcoming various biological barriers, are disclosed. The gene vectors are biodegradable, non-toxic and highly tailorable for use in specific applications. The vectors include a mixture of biodegradable copolymers, such as PBAE, and biodegradable polymers conjugated with hydrophilic, neutrally charged polymer, such as PEG. The gene vectors demonstrate broad vector distribution and high transgene delivery in vivo, providing an efficient non-viral gene delivery system for localized therapeutic gene transfer. Methods of using the vectors to overcome biological barriers including mucus gel and extracellular matrix are provided. Methods of formulating the vectors are also provided.

7 Claims, 26 Drawing Sheets

(56) References Cited

U.S. PATENT DOCUMENTS

| | | | |
|---|---|---|---|
| 2013/0323313 A1* | 12/2013 | Suk | C12N 15/87 424/497 |
| 2015/0086484 A1 | 3/2015 | Hanes | |
| 2016/0235674 A1 | 8/2016 | Mcdonnell | |
| 2016/0243257 A1 | 8/2016 | Suk | |
| 2018/0151472 A1 | 5/2018 | Chen | |

FOREIGN PATENT DOCUMENTS

| | | | |
|---|---|---|---|
| CN | 101926775 | 9/2011 | |
| EP | 1356809 | 10/2003 | |
| EP | 19855309 | 10/2008 | |
| EP | 2156848 | 2/2010 | |
| EP | 2161020 | 3/2010 | |
| EP | 2351556 | 8/2011 | |
| WO | 9503357 | 2/1995 | |
| WO | 9859064 | 12/1998 | |
| WO | 0066180 | 11/2000 | |
| WO | 0224232 | 3/2002 | |
| WO | 02060412 | 8/2002 | |
| WO | 2004112695 | 12/2004 | |
| WO | 2005012407 | 2/2005 | |
| WO | 2005072710 | 8/2005 | |
| WO | 2006114739 | 11/2006 | |
| WO | 2006122542 | 11/2006 | |
| WO | 2007133812 | 11/2007 | |
| WO | 2008030557 | 3/2008 | |
| WO | 2008117927 | 10/2008 | |
| WO | 2009121631 | 1/2009 | |
| WO | 2010017184 | 2/2010 | |
| WO | 2010040188 | 4/2010 | |
| WO | 2010075072 | 7/2010 | |
| WO | 2010086406 | 8/2010 | |
| WO | 2012109363 | 8/2012 | |
| WO | WO-2012109363 A2 * | 8/2012 | A61K 47/59 |
| WO | 2013090804 | 6/2013 | |
| WO | 2013110028 | 7/2013 | |
| WO | 2013158719 | 10/2013 | |
| WO | 2013166408 | 11/2013 | |
| WO | 2014066811 | 5/2014 | |

OTHER PUBLICATIONS

Chirmule, et al., Humoral immunity to adeno-associated virus type 2 vectors following administration to murine and nonhuman primate muscle J Virol, 74(5): 2420-5 (2000).

Dunlap, et al., "Nanoscopic structure of DNA condensed for gene delivery", Nucleic Acids Res, . 25(15): 3095-101 (1997).

Green, et al., "Biodegradable polymeric vectors for gene delivery to human endothelial cells", Bioconjug Chem, 17(5):1162-9 (2006).

Kim, et al., "Non-degradative intracellular trafficking of highly compacted polymeric DNA nanoparticles", J Control Release, 158(1):102-7 (2012).

Konstan, et al., "Compacted DNA nanoparticles administered to the nasal mucosa of cystic fibrosis subjects are safe and demonstrate partial to complete cystic fibrosis transmembrane regulator reconstitution.", Hum Gene Ther, 15(12): 1255-69 (2004).

Kukowska-Latallo, et al., "Intravascular and endobronchial DNA delivery to murine lung tissue using a novel, nonviral vector", Hum Gene Ther, 11(10): 1385-95 (2000).

Lowenstein, et al., "Immune responses to adenovirus and adeno-associated vectors used for gene therapy of brain diseases: the role of immunological synapses in understanding the cell biology of neuroimmune interactions", Curr Gene Ther, 7(5):347-60 (2007).

Lowenstein, et al., "Immunology of neurological gene therapy: how T cells modulate viral vector-mediated therapeutic transgene expression through immunological synapses", Neurotherapeutics, 4(4):715-24 (2007b).

Mastorakos, et al., "Brain penetrating gene vectors for efficient gene transfer to the CNS", Mol Therapy, 22(1):S50 (2014).

Mastorakos, et al., "Highly compacted biodegradable DNA nanoparticles capable of ocercoming thr mucus barrier for inhaled lung gene therapy", PNAS, 112(28):8720-5 (2015).

Mintzer and Simanek, "Nonviral vectors for gene delivery", Chem Rev, 109(2): 259-302 (2009).

Nance, et al., "A dense poly(ethylene glycol) coating improves penetration of large polymeric nanoparticles within brain ti", Sci Transl Med, 4(149):149ra119 (2012).

Neuberg, et al., "Recent developments in nucleic acid delivery with polyethylenimines", Adv. Genet. 88:263-288 (2014).

Olsen and Stein, "New drugs for rheumatoid arthritis", N Engl J Med, . 350(21): 2167-79 (2004).

O'Mahony, et al., "Non-viral nanosystems for gene and small interfering RNA delivery to the central nervous system: formulating the solution", J Pharm Sci, 102(10): 3469-84 (2013).

Suk, et al., "Gene delivery to differentiated neurotypic cells with RGD and HIV Tat peptide functionalized polymeric nanoparticles", Biomaterials, 27:5143-50 (2006).

Suk, et al., "Lung Gene Therapy with Highly Compacted DNA Nanoparticles that Overcome the Mucus Barrier", J Control Release, 178:8-17 (2014).

Sun and Zhang, "Cationic polymer optimization for efficient gene delivery", Mini Rev Med Chem, 10(2):108-25 (2010).

Thomas, et al., "Progress and problems with the use of viral vectors for gene therapy", Nat Rev Genet, 4(5):346-58 (2003).

Tzeng, et al., Non-viral gene delivery nanoparticles based on poly(β-amino esters) for treatment of glioblastoma Biomaterials, 32(23):5402-10 (2011).

Xiao, et al., "Efficient long-term gene transfer into muscle tissue of immunocompetent mice by adeno-associated virus vector", J Virol, 70(11): 8098-108 (1996).

Yadav, et al., "Evaluations of combination MDR-1 gene silencing and paclitaxel administration in biodegradable polymeric nanoparticles formulations to overcome multidrug resistance in cancer cells", Cancer Chemo Pharma., 63(4):711-22 (2009).

Zugates, et al., "Gene delivery properties of end-modified poly([beta]-amino ester)'s", Bioconjug Chem, 18(6): 1887-96 (2007).

International Search Report for corresponding PCT application PCT/US2015/030397 dated Aug. 24, 2015.

Suk et al., "Lung gene therapy with highly compacted DNA nanoparticles that overcome the mucus barrier", Journal of Controlled Release, 178:8-17 (2014).

Arifin, "Remote MR sensing of pH and cell viability using LipoCEST-filled microcapsules", Proc. Intl. Soc. Mag. Reson. Med., 18:42 (2010a).

Arifin, et al., "Remote MRI sensing of pH and cell viability using immunoprotective microcapsules crosslinked with polycationic DIACEST peptides", Intl Soc Magnetic Resonance in Med., 18: 42 , Stockholm Apr. 30-May 7, (2010b).

Auguste, et al. "pH triggered release of protective poly(ethylene glycol)-b-polycation copolymers from liposomes", Biomaterials, 27(12)2599-2608 (2006).

Chan, et al., "Development of CEST liposomes for monitoring nanoparticle-based cancer therapies", Proceeding Intl. Soc Magnetic Resonance Med., 21:0422 21'st meeting, Salt Lake City, Apr. 20-26, 2013.

Cu and Saltzman, "Controlled surface modification with poly(ethylene)glycol enhances diffusion of PLGA nanoparticles in human cervical mucus", Mol. Pharma., 6(1):173-81 (2009).

Cu, et al., "In vivo distribution of surface-modified PLGA nanoparticles following intravaginal delivery", Journal of Controlled Release, 156(2):258-264 (2011).

Ensign, et al., "Oral drug delivery with polymeric nanoparticles: The gastrointestinal mucus barriers", Advanced Drug Delivery Reviews, 64:557-570 (2012).

Ensign, et al., "Mucus Penetrating Nanoparticles: Biophysical Tool and Method of Drug and Gene Delivery", Adv. Mater. 24(28):3887-94 (2012b).

Evbuomwan, et al., "Nanoparticle-based PARACEST agents: the quenching effect of silica nanoparticles on the CEST signal from surface-conjugated chelates", Contrast Media Mol Imaging, 7(1):19-25 (2012).

(56) References Cited

OTHER PUBLICATIONS

Eyles, et al., "The transfer of polystyrene microspheres from the gastrointestinal tract to the circulation after oral administration in the rat", J. Pharm. Pharmacol., 47:561-5 (1995).
Fahmy, et al., "Surface modification of biodegradable polyesters with fatty acid conjugates for improved drug targeting", Biomaterials, 26:5727-5736 (2005).
Ferrari, et al., "Polyethylenimine shows properties of interest for cystic fibrosis gene therapy", Biochemica Biophysica Acta., 1447(2-3):219-25 (1999).
Freichels, et al., "Sugar-labeled and PEGylated (bio) degradable polymers intended for targeted drug delivery systems", Carbohydrate Polymers, 86(3):1093-1106 (2011).
Giannavola, et al., "Influence of preparation conditions on Acyclovir-loaded poly-d, l-lactic acid nanospheres and effect of PEG coating on ocular drug bioavailability", Pharma. Res., 20(4):584-90 (2003).
Gref, et al., "'Stealth' corona-core nanoparticles surface modified by polyethylene glycol (PEG): influences of the corona (PEG chain length and surface density) and of the core composition on phagocytic uptake and plasma protein adsorption", Colloids Surf Biointerfaces, 18:301-13 (2000).
International Search Report for PCT/US2011/026321 dated Nov. 25, 2011.
International Search Report for PCT/US2012/024344 dated Jan. 10, 2013.
International Search Report for PCT/US2012/069882 dated Jun. 19, 2013.
International Search Report for PCT/US2013/022387 dated Jun. 20, 2013.
International Search Report for PCT/US2014/014872 dated Jun. 11, 2014.
International Search Report for PCT/US2016/059661 dated Jan. 20, 2017.
Jeong, et al., "Cellular recognition of paclitaxel-loaded polymeric nanoparticles composed of poly (y-benzyl l-glutamate) and poly (ethylene glycol) diblock copolymer endcapped with galactose moiety", International Journal of Pharmaceutics, 29(1-2):151-16 (2005).
Kemtong, "Polymeric nanomedicine for cancer MR imaging and drug delivery", Chem. Commun., 3497-3510 (2009a).
Kichler, et al., "Intranasal gene delivery with a polyethylenimine-PEG conjugate", J. Control. Release, 81:379-8 (2002).
Kleemann, et al., "Modified polyethylenimines as non-viral gene delivery systems for aerosol gene therapy: investigations of the complex structure and stability during air-jet and ultrasonic nebulization", J Controlled Release, 100(3):437-50 (2004).
Kleemann, et al., "Nano-carriers for DNA delivery to the lung based upon a TAT-derived peptide covalently coupled to PEG-PEI", J Controlled Release, 109(1-3):299-316 (2005).
Lai, et al., "Mucus-penetrating nanoparticles for drug and gene delivery to mucosal tissues", Adv Drug Deliver Rev., 61:158-71 (2009).
Lai, et al., "Rapid transport of large polymeric nanoparticles in fresh undiluted human mucus", PNAS, 104(5):1482-7 (2007).
Lemoine, et al., "Mechanism of efficient transfection of the nasal airway epithelium by hypotonic shock", Gene Ther., 12(16):1275-85 (2005).
Liu, et al., "Developments of mucus penetrating nanoparticles", Asian Journal of Pharmaceutical Sciences, 10:275-282 (2015).
Liu, et al., "In vivo detection of DIACEST contrast agent labeled liposomes using MRI", Contrast Media & Molecular Imaging, 4(6): 294 (2009).
Liu, et al., "In vivo multicolor molecular MR imaging using diamagnetic chemical exchange saturation transfer liposomes", Magnetic Resonance in Medicine, 67(4):1106-1113 (2012).
Ludwig, "The use of mucoadhesive polymers in ocular drug delivery", Adv Drug Deliv Rev., 57:1595-639 (2005).
Maisel, et al., "Nanoparticles coated with high molecular weight PEG penetrate mucus and provide uniform vaginal and colorectal distribution in vivo", Nanomedicine, 11(11):1337-1343 (2016).
McMahon, et al., "New multicolor polypeptide diamagnetic chemical exchange saturation transfer (DIACEST) contrast agents for MRI", Magnetic Resonance Med., 60(4):803-12 (2008).
Peeters, et al., "Can ultrasound solve the transport barrier of the neural retina", Pharma Res., 25(11):2657-65 (2008).
Rajapaksa, et al., "Intranasal M cell uptake of nanoparticles is independently influenced by targeting ligands and buffer ionic strength", J. Biol. Chem., 285:23739-46 (2010).
Sanders, et al., "Extracellular barriers in respiratory gene therapy", Adv. Drug Deliv. Rev. 61:115-27 (2009).
Sheng, et al., "In vitro macrophage uptake and in vivo biodistribution of PLA-PEG nanoparticles loaded with hemoglobin as blood substitutes: effect of PEG content", J. Mater. Sci. Mater. Med., 20(9):1881-91 (2009).
Sherry, "Chemical Exchange Saturation Transfer Contrast Agents for Magnetic Resonance Imaging", Annu. Rev. Biomed. Eng., 10:391-411 (2008).
Song, et al., Quantitative CEST imaging with reduced MT interference using dual-frequency irradiation, Proceedings Intl Soc Magnetic Resonance Med, 20:4190 (2012).
Soppimath, et al., "Biodegradable polymeric nanoparticles as drug delivery devise", J Cont. Release, 70:1-20 (2001).
Suk, et al., "Overcoming the cystic fibrosis sputum barrier to nanoparticle-based gene carriers", Ph. D. thesis, 93-94 (2011).
Tang, et al., "Polyethylene glycol modified polyethylenimine for improved CNS gene transfer: effects of PEGylation extent", Biomaterials, 24(13):2351-62 (2003).
Terry, "Ternary particles for effective vaccine delivery to the pulmonary system", (Ph.D. Thesis, UMI ProQuest, Ann Arbor (2008).
Vega, et al., "Flurbiprofen Loaded Biodegradable Nanoparticles for Ophtalmic Administration", J. Pharma. Sci., 95(11):2393-2405 (2006).
Wang, et al., "Addressing the PEG mucoadhesivity Paradox to Engineer Nanoparticles that "Slip" through the Human Mucus Barrier", Angewandte Chemie International Edition, 47:9726-9729 (2008).
Ward, et al., "A new class of contrast agents for MRI based on proton chemical exchange dependent saturation transfer (CEST)", J Magnetic Resonance, 143:79-87 (2000).
Yen, et al., "Controlled Surface Modification with Poly (ethylene) glycol Enhances Diffusion of PLGA Nanoparticles in Human Cervical Mucus", J. Contr. Rel., 158(2):258-264 (2011).
Zhang, et al., "Micelles based on biodegradable poly(L-glutamic acid)-b-polylactide with paramagnetic Gd ions chelated to the shell layer as a potential nanoscale MRI-visible delivery system", Biomacromolecules, 9:36-42 (2008).
Zimmer, et al., "Microspheres and nanoparticles used in ocular delivery systems", Advanced Drug Delivery Reviews, 16:61-73 (1995).

\* cited by examiner

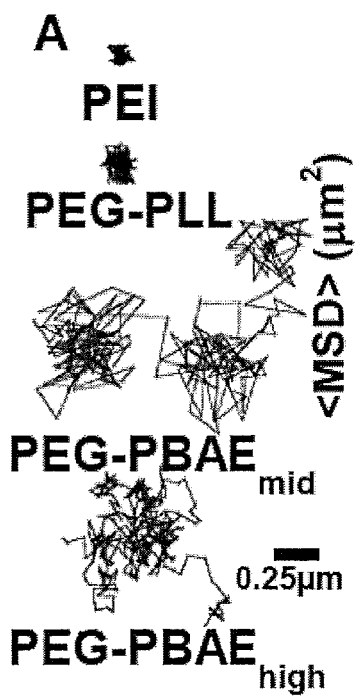
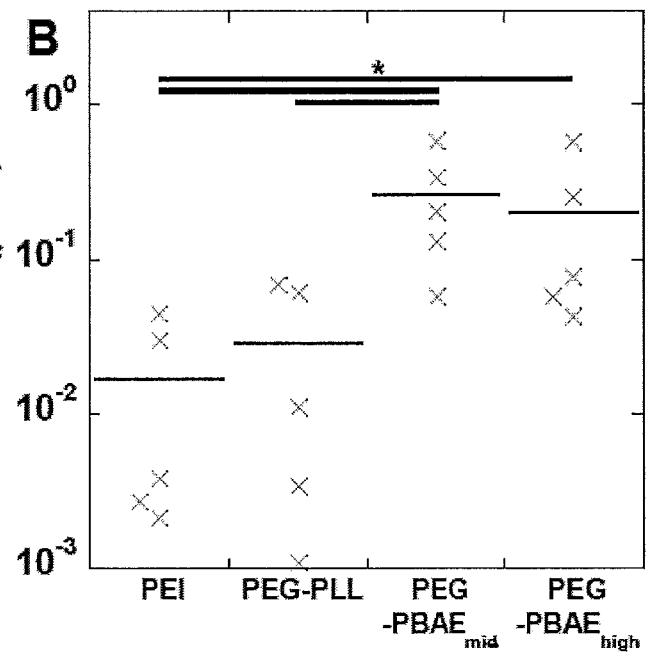
FIG. 3A          FIG. 3B
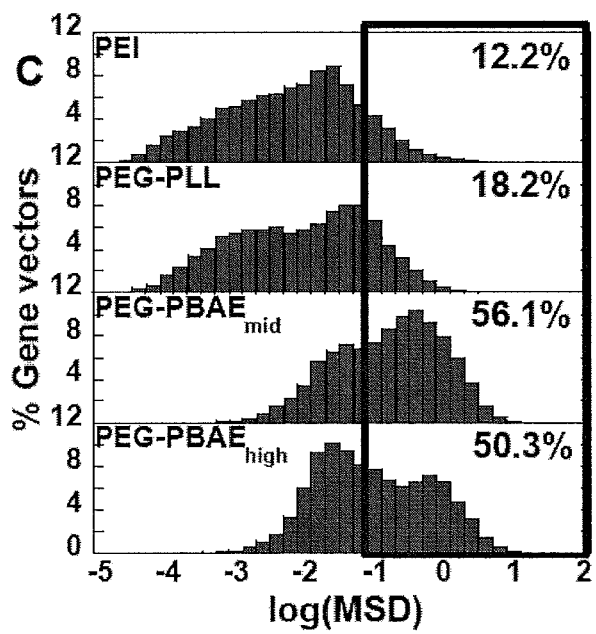
FIG. 3C

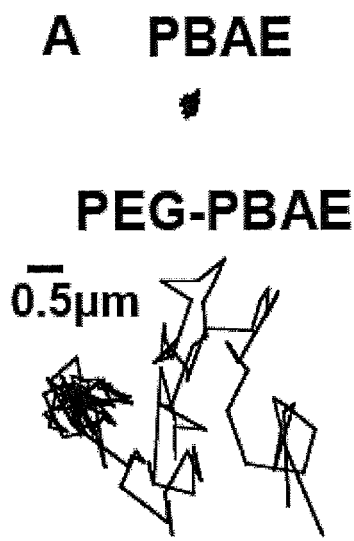
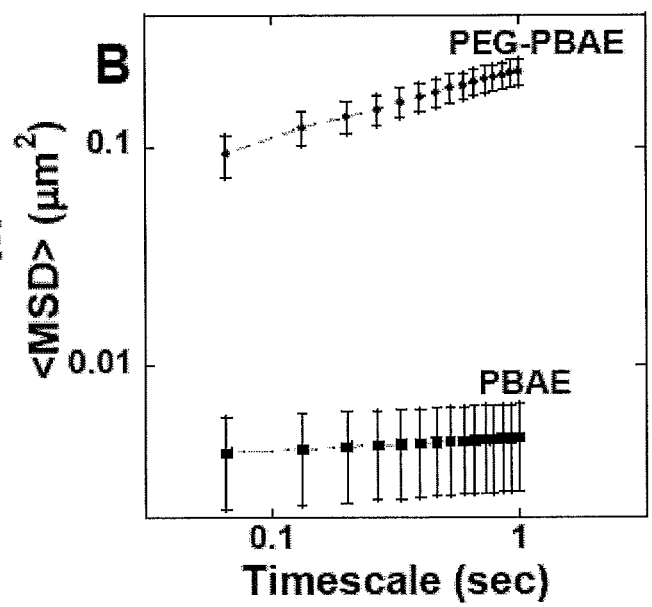
FIG. 8A
FIG. 8B
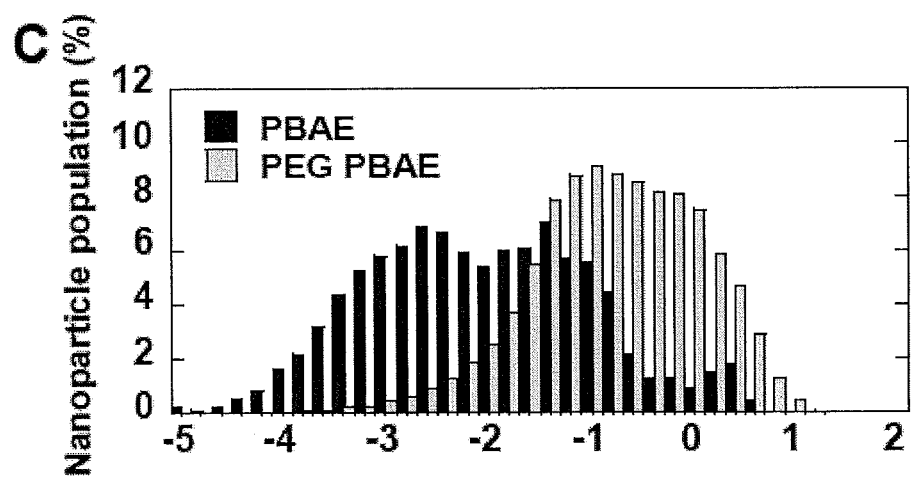
FIG 8C

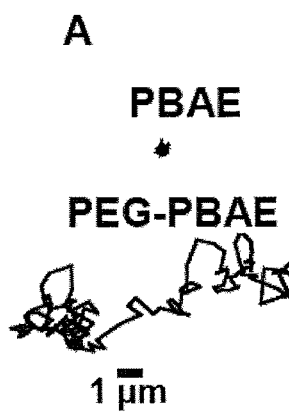
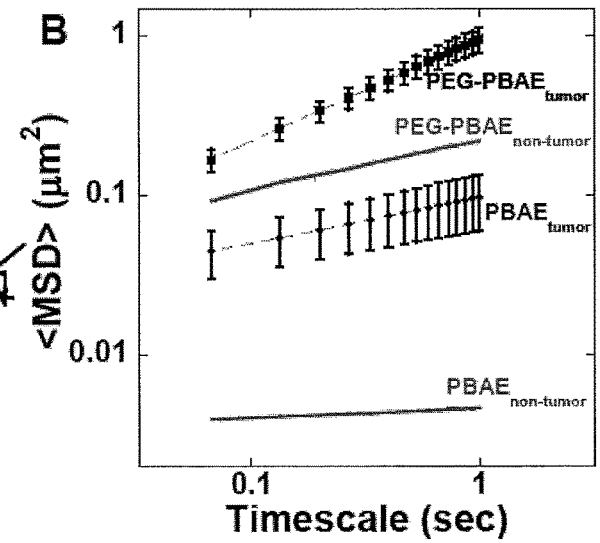
FIG. 9A  FIG. 9B
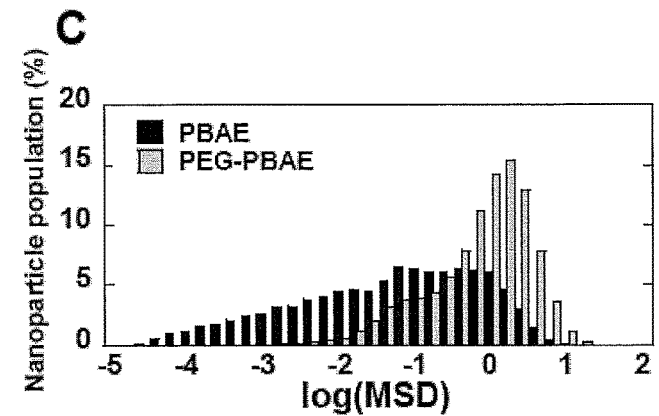
FIG. 9C

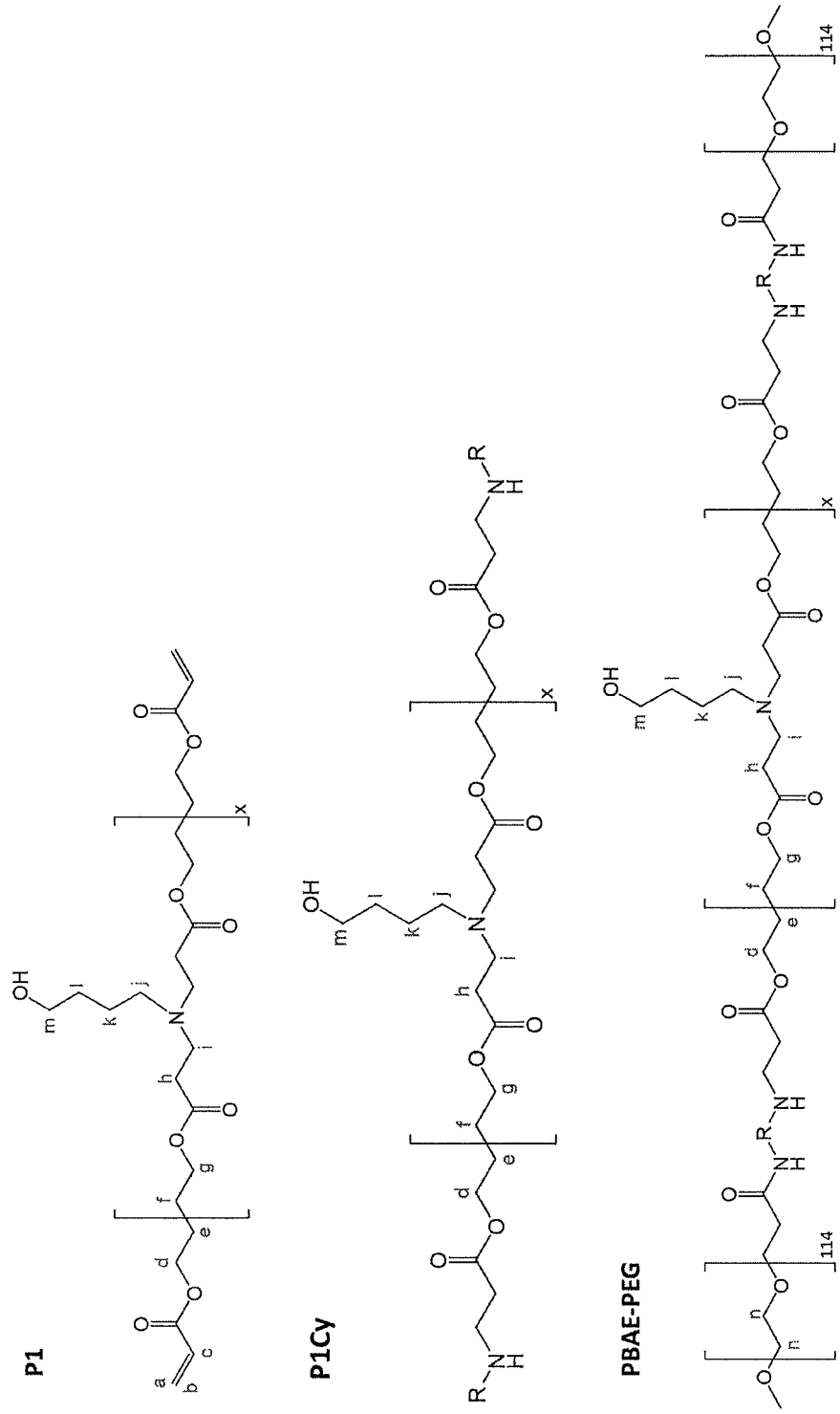
FIG. 16A, 16B, and 16C

HIGHLY STABLE BIODEGRADABLE GENE VECTOR PLATFORMS FOR OVERCOMING BIOLOGICAL BARRIERS

CROSS-REFERENCE TO RELATED APPLICATIONS

This application is a divisional of U.S. Ser. No. 15/310,643, filed Nov. 11, 2016, which is a national phase application under 35 U.S.C. § 371 of International Application No. PCT/US2015/030397, filed May 12, 2015, which claims priority to and benefit of U.S. Ser. No. 61/991,946 filed May 12, 2014 and U.S. Ser. No. 62/001,884 filed May 12, 2014, the disclosures of which are expressly incorporated herein by reference.

STATEMENT REGARDING FEDERALLY SPONSORED RESEARCH OR DEVELOPMENT

This invention was made with Government Support under EB003558 and CA164789 awarded by the National Institutes of Health. The Government has certain rights in the invention.

FIELD OF THE INVENTION

This invention is generally in the field of gene delivery, and in particular, using coated, stable, biodegradable particles to penetrate anatomical barriers in order to achieve high level and widespread transgene expression.

BACKGROUND OF THE INVENTION

Gene therapy has rapidly emerged as an attractive strategy for the treatment of a wide variety of genetic disorders with particular focus on the respiratory and central nervous system (CNS).

Viruses have been extensively studied both pre-clinically and clinically and have demonstrated relatively efficient gene transfer, they exhibit certain limitations. Viral gene vectors, though relatively efficient, present a number of drawbacks including: low packaging capacity, technical difficulties in scale-up, high cost of production (Thomas, et al., *Nat Rev Genet*, 2003. 4(5): 346-58) and risk of mutagenesis (Olsen and Stein, *N Engl J Med*, 2004. 350(21): 2167-79). Furthermore, neutralizing immune responses may occur secondary to repeated administrations (Xiao, et al., *J Virol*, 1996. 70(11): 8098-108) or prior exposures (Chirmule, et al., *J Virol*, 2000. 74(5): 2420-5; Lowenstein, et al., *Curr Gene Ther*, 2007. 7(5): 347-60; Lowenstein, et al., *Neurotherapeutics*, 2007. 4(4): 715-24).

Non-viral gene vectors offer an attractive alternate strategy for gene delivery (O'Mahony, et al., *J Pharm Sci*, 2013. 102(10): 3469-84). Cationic polymer-based gene vectors provide a tailorable platform for DNA condensation and efficient gene transfer. Their positive charge density allows for stable compaction of negatively charged nucleic acids (Sun and Zhang, *Mini Rev Med Chem*, 2010. 10(2): 108-25; Dunlap, et al., *Nucleic Acids Res*, 1997. 25(15): 3095-101) and protects them from enzymatic degradation (Kukowska-Latallo, et al., *Hum Gene Ther*, 2000. 11(10): 1385-95). Also, the number of protonable amines provides increased buffering capacity that facilitates endosome escape via the "proton sponge effect", leading to efficient transfection (Akinc, et al., *J Gene Med*, 2005. 7(5): 657-63; Akinc, and Langer, *Biotechnol Bioeng*, 2002. 78(5): 503-8). For these reasons cationic polymer based gene vectors exhibit successful gene delivery in vitro.

However, gene vectors offering high level transgene expression are usually associated with some level of cytotoxicity due to the highly cationic nature of these platforms. Moreover, in vivo delivery is hindered by their instability under physiological conditions (Mintzer and Simanek, *Chem Rev*, 2009. 109(2): 259-302) as well as their inability to penetrate biological barriers, such as the airway mucus (Suk, et al., *J Control Release*, 2014), the extracellular matrix and tumor tissues. Poly (β-amino ester) polymers (PBAE), in particular, provide a non-toxic, biodegradable polymer library for the compaction of DNA, offering highly effective gene delivery in vitro even in cells that are hard to transfect (Akinc, et al., *Bioconjug Chem*, 2003. 14(5): 979-88; Green, et al., *Bioconjug Chem*, 2006. 17(5): 1162-9; Zugates, et al., *Bioconjug Chem*, 2007. 18(6): 1887-96). Moreover, the subtle variations in the polymer backbone and end-capping groups offer cell type specific transgene expression (Tzeng, et al., *Biomaterials*, 2011. 32(23): 5402-10).

These vectors generally lack the means to overcome numerous extracellular biological barriers, resulting in low in vivo transgene delivery. The hydrolytic nature and relatively low positive charge density of these polymers results in drastically reduced colloidal stability and loose DNA compaction, thereby limiting their use in vivo and their potential for clinical applications. A delivery system for nucleic acid must provide efficient DNA compaction that will protect the DNA from serum nucleases and deliver the DNA to the target cells with effective high level transgene expression. Additionally, the formulation must be suitable for large scale production and stable in physiological conditions.

It is therefore an object of the present invention to provide biodegradable vectors having improved colloidal stability in physiological environments, enhanced penetration through biological barriers, tissue distribution, and delivery of nucleic acid payloads to the target cells.

It is a further object of the present invention to provide gene delivery vectors with low in vivo toxicity (i.e. acceptable safety profiles).

SUMMARY OF THE INVENTION

Compact, colloidally stable PBAE-based gene vectors that have a dense surface coverage of hydrophilic and neutrally charged PEG (PEG-PBAE) have been developed. These gene vectors stably retain their physicochemical characteristics over at least a week in aqueous solution and post-lyophilization, and are highly stable in physiological solutions. Moreover, they demonstrate the ability to penetrate physiological barriers such as airway mucus and brain tissue/tumor allowing for widespread distribution and high level transgene expression in vivo. These advantages provide the opportunity to expand this highly tailorable and biodegradable polymeric platform, otherwise limited to in vitro applications, to in vivo applications and render it more clinically relevant.

Methods of making nanoparticles densely coated with hydrophilic, neutrally charged polymer for the delivery of nucleic acids across biological barriers include preparing a blended polymer by mixing free polymer with polymer conjugated to hydrophilic, neutrally charged polymer. Typically, the molar ratio of free polymer to conjugated polymer is optimized for producing colloidally stable nanoparticles with a hydrodynamic diameter less than 100 nm and a near neutral surface charge. The methods also include the use of hydrochloride solution (HCL) to adjust the polymer and DNA solution pH for efficient DNA compaction. The methods also include adding nucleic acid to the blended polymer, wherein up to 10 volumes of nucleic acid are added to one volume of blended polymer at a steady rate of up to 10 ml/min. The mass ratio of the nucleic acid to blended polymer is optimized for producing colloidally stable nanoparticles with a hydrodynamic diameter less than 100 nm and a near neutral surface charge. The methods also include purifying the nanoparticles to remove unused (unbound) polymers and concentrating to therapeutically relevant concentration for local administration.

The examples demonstrate using a mixture of polyethylene glycol/poly (β-amino ester) (PEG-PBAE) copolymer and poly (β-amino ester) (PBAE) to formulate highly compact 50 nm gene vectors with a near neutral surface charge. By blending non-PEGylated PBAE core polymers of different molecular weights (4 kDa, $PBAE_{low}$; 7 kDa, $PBAE_{mid}$; 11 kDa, $PBAE_{high}$) with PEGylated $PBAE_{low}$, three gene vectors: $PEG-PBAE_{low}$, $PEG-PBAE_{mid}$, and $PEG-PBAE_{high}$, respectively, with similar physicochemical characteristics were prepared. $PEG-PBAE_{mid}$ was compared to non-PEGylated PBAE gene vectors which formed gene vectors with a diameter less than 100 nm, high polydispersity and positive surface charge. Lyophilization of these nanoparticles using 2% sucrose as a cryopreservant drastically increased the size and polydispersity of PBAE gene vectors, while only minor changes were observed with the PEG-PBAE gene vectors. Following incubation of PBAE and PEG-PBAE gene vectors in ultra-pure water in room temperature, PEG-PBAE demonstrated high stability over 1 week while PBAE started increasing in size after 20 hours and reached PDI>0.5 after 30 hours, indicating aggregation and lack of colloidal stability. In vitro stability in BALF and aCSF at 37° C. over time showed that PBAE gene vectors reached PDI>0.5 at 1 hour incubation in aCSF or BALF, indicating rapid loss of colloidal stability. PEG-PBAE retained their colloidal stability in BALF with a sub-100 nm hydrodynamic diameter over 20 hours of incubation. The hydrodynamic diameter of PEG-PBAE increased to 80 nm following addition to aCSF and remained stable over 6 hours. After 6 hours the gene vectors doubled in size and retained their colloidal stability for up to 15 hours.

The transfection efficacy of these gene vectors to conventionally used polyethylenimine (PEI) and PEG-poly-L-lysine (PEG-PLL) gene vectors was assessed in bronchial epithelial cells. $PEG-PBAE_{mid}$ and $PEG-PBAE_{high}$ demonstrated high transfection efficacy, while $PEG-PBAE_{low}$ resulted in significantly lower transfection. All PEG-PBAE formulations had significantly lower in vitro transfection than PEI gene vectors. This may be attributed to their dense PEG surface coating reducing cell uptake and endosome escape. The diffusion of PEG-PBAE in comparison to PEI and PEG-PLL, in freshly expectorated sputum from cystic fibrosis patients, was assessed using multiple particle tracking (MPT). PEI and PEG-PLL were strongly hindered with constrained non-Brownian time-lapse traces. PEG-PBAE trajectories spanned over greater distances indicating unhindered diffusion in CF sputum. At least half of PEG-PBAE gene vectors were able to efficiently penetrate CF sputum, whereas only 12.2% of PEI and 18.2% of PEG-PLL could do so.

PEG-PBAE homogeneously distributed in the large airways and effectively reached the alveoli covering the entire lung parenchyma, following intratracheal administration to the mouse lungs. Mice dosed identically with PEI or PEG-PLL demonstrated sparse areas of highly accumulated gene vectors in the large airways, suggesting aggregation and entrapment of gene vectors in the luminal mucus gel layer covering the airway epithelium. PEG-PBAE gene vectors with both high and low molecular weights resulted in significantly higher transfection in comparison to PEI and PEG-PLL. The intranasal administration of PEG-PBAE, despite a large fraction being retained in nostril or delivered to gastrointestinal tract, resulted in transgene expression comparable to that achieved by intratracheal administration of PEI where the gene vectors are directly aerosolized in the respiratory tract. Repeated administrations of PEG-PBAE gene vectors do not decrease transfection efficacy. Different storage methods do not affect in vivo transfection efficacy of PEG-PBAE. The high level transfection achieved by PEG-PBAE and the use of a unmethylated CpG-free β-actin promoter resulted in long term transgene expression over at least 4 months. Also, PEG-PBAE demonstrated negligible lung inflammation similar to that of clinically tested PEG-PLL and non-treated mice and significantly lower than that of PEI gene vectors.

PEG-PBAE is able to effectively transfect primary astrocytes and human glioblastoma cells in vitro. PEG-PBAE is taken up by cells 6 and 3-fold more than PEG-PLL, for primary astrocytes and human glioblastoma cells, respectively. However, PEI gene vectors are taken up by cells 1.5 and 2.8 fold more than PEG-PBAE for primary astrocytes and human glioblastoma cells, respectively. Luciferase expression following PEG-PBAE treatment did not differ significantly from PEI for primary astrocytes while PEG-PBAE transfected U87 cells lower than PEI.

The diffusion of PEG-PBAE and PBAE in healthy rodent brain was assessed using MPT. The PBAE were strongly hindered in the brain parenchyma with constrained non-Brownian time-lapse traces. In contrast, PEG-PBAE trajectories spanned over greater distances, indicating the unhindered diffusion in brain tissue. 65% of PEG-PBAE could rapidly penetrate the brain in comparison to only 19% of PBAE. Both gene vectors diffused more rapidly in tumor tissue in comparison to non-tumor tissue. However, PEG-PBAE achieved significantly higher tumor penetration in comparison to PBAE gene vectors.

When separately administered in the rodent striatum using convection enhanced delivery (CED), PEG-PBAE covered a 6.3-fold larger area than PBAE did and the difference in distribution was statistically significant ($p<0.05$). Moreover, the overall volume of distribution of PEG-PBAE was calculated to be 20-fold higher than for PBAE. PEG-PBAE is able to effectively transfect cells far from the injection site while PBAE resulted in transgene expression only in cells in the immediate vicinity to the injection site. The volume of transfection was 11.1-fold higher for PEG-PBAE in comparison to PBAE. The improved distribution of PEG-PBAE resulted in a 2-fold higher absolute level of transgene expression compared to PBAE.

Similarly, infusion of PEG-PBAE in a rodent orthotopic F98 brain tumor resulted in improved distribution and transfection away from the point of administration. The volume of transfection was 5.3-fold higher compared to PBAE. PEG-PBAE were able to reach and transfect more than 50% of tumor cells, while conventional particles resulted in transgene expression in less than 20% of cells. The absolute levels of transgene expression were 2.7-fold higher for PEG-PBAE compared to PBAE. The improved distribution and transfection efficiency of PEG-PBAE lead to markedly enhanced therapeutic effect following administration of therapeutic plasmids in an orthotopic glioblastoma model.

Dosage formulations for delivery of nucleic acids, including a therapeutically effective amount of the disclosed nanoparticles and a pharmaceutically acceptable excipient for delivery, are also provided. The nanoparticles can be formulated for administration to different organs including but not limited to the brain, or the lung. In some embodiments the nanoparticle releases an effective amount of the one or more nucleic acids over a period of at least 10 minutes, 20 minutes, 30 minutes, one hour, two hours, three hours, six hours, ten hours, one day, three days, seven days, ten days, two weeks, one month, or longer.

Methods for treating a disease or disorder, including administering to a subject in need thereof a formulation including a therapeutically effective amount of the disclosed nanoparticles and a pharmaceutically acceptable excipient for delivery to alleviate one or more symptoms of the disease or disorder, are provided. The methods can include administering the formulation to the brain, or to the lung. In some embodiments the methods include administering the particles in combination with one or more techniques to facilitate bypassing of the blood brain barrier. Exemplary techniques include topical bolus administration, convection enhanced delivery, electron paramagnetic resonance, ultrasound, and ultrasound plus microbubbles. The methods can be useful for treating disorders including tumors, neurological disorders, and brain injury or trauma, lung injury or trauma, cystic fibrosis, asthma, chronic obstructive pulmonary disease, diseases caused by infection with bacteria and diseases caused by infections with viruses. In certain embodiments the methods include nanoparticles that previously have been lyophilized.

BRIEF DESCRIPTION OF THE DRAWINGS

FIGS. 3A to 3C show a schematic of representative particle trajectories over 20S in freshly expectorated CF mucus (FIG. 3A), a dot-blot graph showing MSD ($\mu m^2$) (FIG. 3B) and a set of histograms showing % gene vectors over log (MSD) (FIG. 3C) for PEI, PEG-PLL, PEG-PBAE (LOW), PEG-PBAE (MID) and PEG-PBAE (HIGH) gene vectors, respectively. Polyethyleneimine (PEI) and Polyethylene glycol poly-lysine (PEG-PLL) based gene vectors were used as controls. FIG. 3E is a bar graph of percentage of epithelium coverage by the particles. FIG. 3F is a bar graph showing airway distribution variation of the particles. FIG. 3G is a bar graph showing percentage of lung coverage by the particles. FIG. 3H is a bar graph showing lung distribution variation of the particles.

FIGS. 8A to 8C show a schematic of representative particle trajectories over 20 seconds (20S) (FIG. 8A); a graph showing ensemble averaged mean of MSD ($\mu m^2$) over time (seconds) with N≥500 particles tracked for each expt. (FIG. 8B); and histograms showing nanoparticle population (%) at a timescale of T=1 second, (FIG. 8C) respectively, for each of PBAE and PEG PBAE gene vectors in rodent brain tissue.

FIGS. 9A to 9C show a schematic of representative particle trajectories over 20S in brain tissue (FIG. 9A); a graph showing ensemble averaged mean of MSD ($\mu m^2$) over time (seconds) with N≤500 particles tracked for each experiment, overlayed with representative trace obtained for particles in non-tumor tissue (FIG. 9B); and histograms showing nanoparticle population (%) at a timescale of T=1 second, (FIG. 9C) respectively, for each of PBAE and PEG PBAE gene vectors in rodent brain tumor tissue.

FIGS. 16A, 16B and 16C are schematics of P1 (FIG. 16A), P1Cy (FIG. 16B) and PBAE-PEG (FIG. 16C) chemical structures.

FIG. 17A is NMR spectra of high MW (6.0-6.5 kDa) P1 PBAE polymer synthesized by a Michael addition reaction of 1,4-butanediol diacrylate and 4-amino-1-butanol (P1; x=19-20). FIG. 17B is NMR spectra of high MW P1 PBAE capped by 2-(3-aminopropylamino)ethanol (C5) (P1C5). FIG. 17C is NMR spectra of low MW (3.8-4.2 kDa) P1 PBAE (x=13-14). FIG. 17D is NMR spectra of low MW P1 PBAE capped by 1,3-diaminopropane (C1) (P1C1). FIG. 17E is NMR spectra of PEGylated P1C1 PBAE (PBAE-PEG) at a 2:1 PEG to PBAE molar ratio. End capping is confirmed by the loss of diacrylate peaks (a, b and c).

DETAILED DESCRIPTION OF THE INVENTION

I. Definitions

Figures 1A, 1B:
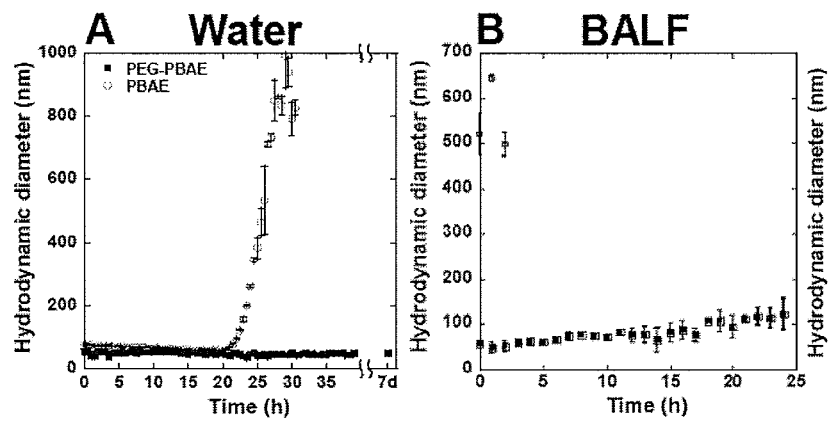
FIGS. 1A to 1C are graphs showing the hydrodynamic diameter (nm) of PEG-PBAE (■) and PBAE (○) vectors over time (hours) in water (FIG. 1A), Bronchoalveolar lavage fluid (BALF) (FIG. 1B) and artificial cerebrospinal fluid (aCSF) (FIG. 1C), respectively. Size was measured by dynamic light scattering (DLS) in aCSF at pH 7.0. Measurements continued for 40 hours every 15 mins or half an hour or until polydispersity (PDI)>0.5. Data represents the mean±SEM.

The terms "biocompatible" as used herein refers to one or more materials that are neither themselves toxic to the host (e.g., an animal or human), nor degrade (if the polymer degrades) at a rate that produces monomeric or oligomeric subunits or other byproducts at toxic concentrations in the host.

The term "biodegradable" as used herein means that the materials degrades or breaks down into its component subunits, or digestion, e.g., by a biochemical process, of the polymer into smaller, non-polymeric subunits.

The term "corresponding particle", "conventional particle" or "reference particles" as used herein refers to a particle that is substantially identical to another particle to which it is compared, but typically lacking a surface modification to promote effective compaction, colloidal stability and transport differences through the pores of airway mucus and of the extracellular matrix (ECM) of the brain. In certain embodiments, a corresponding particle is a particle that does not have a dense coating of polyethylene glycol. In certain embodiments, a comparable particle is a particle that is not formed of a blended mixture containing free polymer and polymer conjugated to polyethylene glycol.

The term "densely coated particle" refers to a particle that is modified to specifically enhance the density of coating agent at the surface of the particle, for example, relative to a reference particle. In some embodiments, a densely coated particle is formed from a ratio of polyethylene glycol to polymer that is sufficient to alter the physicochemical properties of the particle relative to a less densely coated, or non-coated particle. In some embodiments, the density of coating agent is sufficient to completely mask the charge of the particle, resulting in a near neutral charge and near neutral zeta potential value and colloidal stability in physiological solutions. In a particular embodiment, a densely coated particle is achieved using branched polyethylene glycol or branched polymer, wherein the branching enhances the ratio of polyethylene glycol to polymer as compared to a reference particle that does not contain a branched polymer or branched polyethylene glycol The term "nucleic acids" refers to isolated DNA, cDNA, RNA, miRNA, siRNA, plasmids, vectors, and expression constructs.

The term "diameter" is art-recognized and is used herein to refer to either of the physical diameter or the hydrodynamic diameter. The diameter of an essentially spherical particle may refer to the physical or hydrodynamic diameter. The diameter of a non-spherical particle may refer preferentially to the hydrodynamic diameter. As used herein, the diameter of a non-spherical particle may refer to the largest linear distance between two points on the surface of the particle. When referring to multiple particles, the diameter of the particles typically refers to the average diameter of the particles.

The term "microspheres", "microparticles", and "microcapsules are used interchangeably unless otherwise stated. These have a size between about one up to about 1000 microns. In general, "microcapsules," have a core of a different material than the shell material. A microparticle may be spherical or nonspherical and may have any regular or irregular shape. If the structures are less than about one micron in diameter, then the corresponding art-recognized terms "nanosphere," "nanocapsule," and "nanoparticle" may be utilized. In certain embodiments, the nanospheres, nanocapsules and nanoparticles have an average diameter of about 100 nm, or less than 100 nm, such as 50 nm, or 10 nm.

A composition comprising microparticles or nanoparticles may include particles of a range of particle sizes. In certain embodiments, the particle size distribution may be uniform, e.g., within less than about a 20% standard deviation of the median volume diameter, and in other embodiments, still more uniform, e.g., within about 10% of the median volume diameter.

The phrases "parenteral administration" and "administered parenterally" are art-recognized terms, and include modes of administration other than enteral and topical administration, such as injections, and include without limitation intravenous, intramuscular, intrapleural, intravascular, intrapericardial, intraarterial, intrathecal, intracapsular, intraorbital, intracardiac, intradennal, intraperitoneal, transtracheal, subcutaneous, subcuticular, intraarticular, subcapsular, subarachnoid, intraspinal and intrastemal injection and infusion.

The term "therapeutic agent" refers to an agent that can be administered to prevent or treat a disease or disorder. Examples include, but are not limited to, a nucleic acid, a nucleic acid analog, a small molecule, a peptidomimetic, a protein, peptide, carbohydrate or sugar, lipid, or surfactant, or a combination thereof.

The term "treating" refers to preventing or alleviating one or more symptoms of a disease, disorder or condition. Treating the disease or condition includes ameliorating at least one symptom of the particular disease or condition, even if the underlying pathophysiology is not affected, such as treating the pain of a subject by administration of an analgesic agent even though such agent does not treat the cause of the pain.

The phrase "pharmaceutically acceptable" refers to compositions, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The phrase "pharmaceutically acceptable carrier" refers to pharmaceutically acceptable materials, compositions or vehicles, such as a liquid or solid filler, diluent, solvent or encapsulating material involved in carrying or transporting any subject composition, from one organ, or portion of the body, to another organ, or portion of the body. Each carrier must be "acceptable" in the sense of being compatible with the other ingredients of a subject composition and not injurious to the patient.

The phrase "therapeutically effective amount" refers to an amount of the therapeutic agent that produces some desired effect at a reasonable benefit/risk ratio applicable to any medical treatment. The effective amount may vary depending on such factors as the disease or condition being treated, the particular targeted constructs being administered, the size of the subject, or the severity of the disease or condition. One of ordinary skill in the art may empirically determine the effective amount of a particular compound without necessitating undue experimentation.

As used herein, "convection enhanced delivery" (CED) refers to drug delivery through one to several catheters placed stereotactically directly within a tumor mass or around the tumor or the resection cavity or within the brain.

As used herein, "intrathecal administration" refers to the introduction of a therapeutic substance by injection into the subarachnoid space of the spinal cord. This is a strategy to bypass the blood-brain barrier by using an alternate route of delivery.

As used herein, "inhalation", results from the negative pressure in the lungs caused by contraction of the diaphragm, which causes it to move downwards and to expand the chest cavity, providing a means for delivery of drug directly into the bloodstream.

The terms "incorporated" and "encapsulated" refer to incorporating, formulating, or otherwise including an active agent into and/or onto a composition that allows for release, such as sustained release, of such agent in the desired application. The terms contemplate any manner by which a therapeutic agent or other material is incorporated into a polymer matrix, including chemically or physically coupled, in physical admixture, or enveloping the agent in a coating layer.

II. Compositions

A. Nanoparticles

Synthetic gene delivery platforms with a dense surface coating of hydrophilic and neutrally charged polymer, capable of rapid diffusion and widespread distribution through mesh-like biological barriers, such as the airway mucus and the healthy and tumor brain extracellular matrix, are disclosed.

Gene vector platforms formed from polymers such as poly (β-amino ester) polymers (PBAE) conjugated to hydrophilic, neutrally charged polymer such as polyethylene glycol (PEG) provide a non-toxic, biodegradable polymer library for the compaction of DNA, offering highly effective gene delivery in vitro and in vivo. The polymers can be synthesized using semi-automated high-throughput combinatorial chemistry offering a large variety of polymers ((Akinc, et al., *Bioconjug Chem,* 2003. 14(5): 979-88)) for the formulation of gene vectors with different chemical properties, while providing high density surface PEG coatings.

PEGylation of cationic polymers may have negative influences on DNA complexation due to reduction of available positive charges resulting from the PEG conjugation to the amine groups of cationic polymers and additional steric hindrance imposed by grafted PEG chains. To overcome this limitation and achieve dense PEG surface coating, a non-PEGylated polymer core was used for compact DNA complexation. In some embodiments the blended polymer contains a molar ratio of free polymer to conjugated polymer of between 0.25 and 1, for example, about 0.67. An exemplary polymer is poly (β-amino ester) polymer. In some embodiments the mass ratio of the total PBAE polymer to the nucleic acid is up to 100, for example, about 60. The concentration of the blended polymer can be up to 2,000 times the concentration of the nucleic acid, for example the concentration of polymer can be about 300 times the concentration of the nucleic acid in their respective solutions. The concentration of nucleic acid solution can be up to 5 mg/ml.

Exemplary colloidally stable nanoparticles for delivery of nucleic acids across biological barriers include nucleic acid, poly (β-amino ester) polymer and hydrophilic, neutrally charged polymer. At least 25% of the poly (β-amino ester) in the nanoparticles is conjugated to hydrophilic, neutrally charged polymer and the nucleic acids are encapsulated within the nanoparticles or are associated with the surface of the nanoparticles. The nanoparticles are coated with hydrophilic, neutrally charged polymer at a density that imparts a near neutral surface charge, and have a diameter of less than 100 nm. Typically, the poly (β-amino ester) has a molecular weight greater than 2,000 Daltons, for example, 7,000 Daltons. In one embodiment, the hydrophilic, neutrally charged polymer is polyethylene glycol that has a molecular weight between 1,000 Daltons and 10,000 Daltons, for example 5,000 Daltons.

Effective DNA compaction was achieved using a mixture of polymers conjugated with a hydrophilic, neutrally charged polymer and non-conjugated polymers. Formulation parameters such as polymer/DNA weight ratio, free polymer/conjugated polymer ratio, pH of DNA and polymer solutions, type of buffering solution and method of mixing can be optimized to increase stability and transfection efficiency. These gene vectors retain their physicochemical characteristics, including hydrodynamic diameter, polydispersity index and surface charge, over at least a week in aqueous solution and post-lyophilization. They are also highly stable in physiological solutions, including bronchoalveolar laveage fluid (BALF) and artificial cerebrospinal fluid (aCSF).

The increased stability of this platform overcomes an important limitation of the conventional PBAE nanoparticles. Moreover, the dense coating of a hydrophilic, neutrally charged polymer, indicated by their near neutral surface charge, in combination with their relatively small diameter allows them to rapidly penetrate through mesh-like biological barriers such as the airway mucus and the healthy and tumor brain extracellular matrix. These attributes offer a window of opportunity for in vivo transgene delivery to different organs, especially the respiratory and central nervous systems.

1. Coating Agents

Surface-altering coating agents that impart a near-neutral negative charge and promote penetration and diffusion of the particles through biological barriers are disclosed. The coating agents minimize interactions with the highly adhesive and electrostatically charged components of mesh like biological barriers, such as the airway mucus, brain extracellular matrix and tumor tissue.

Exemplary coating agents include, but are not limited to, anionic proteins (e.g., albumin), surfactants (e.g. polyvinyl alcohol), sugars or sugar derivatives (e.g., cyclodextrin), and polymers. Examples of coating agents include polyethylene glycol ("PEG") and poloxomers (polyethylene oxide block copolymers).

A preferred coating agent is poly(ethylene glycol), also known as PEG. PEG may be employed to improve compaction, enhance stability and reduce adhesion in brain ECM and airway mucus in certain configurations, e.g., wherein the length of PEG chains extending from the surface is controlled (such that long, unbranched chains that interpenetrate into the ECM are reduced or eliminated). For example, linear high MW PEG may be employed in the preparation of particles such that only portions of the linear strands extend from the surface of the particles (e.g., portions equivalent in length to lower MW PEG molecules). Alternatively, branched high MW PEG may be employed. In such embodiments, although the molecular weight of a PEG molecule may be high, the linear length of any individual strand of the molecule that extends from the surface of a particle would correspond to a linear chain of a lower MW PEG molecule.

Representative PEG molecular weights in daltons (Da) include 300 Da, 600 Da, 1 kDa, 2 kDa, 3 kDa, 4 kDa, 5 kDa, 6 kDa, 8 kDa, 10 kDa, 15 kDa, 20 kDa, 30 kDa, 50 kDa, 100 kDa, 200 kDa, 500 kDa, and 1 MDa. In preferred embodiments, the PEG has a molecular weight of about 5,000 Daltons. PEG of any given molecular weight may vary in other characteristics such as length, density, and branching. In a particular embodiment, a coating agent is methoxy-PEG-amine, with a MW of 5 kDa. In another embodiment, a coating agent is methoxy-PEG-N-hydroxysuccinimide with a MW of 5 kDa (mPEG-NHS 5 kDa).

In preferred embodiments the nanoparticles are coated with PEG or other hydrophilic coating agent at a density that imparts a near neutral surface charge. The density of the coating can be varied based on a variety of factors including the material and the composition of the particle.

In a preferred embodiment the molar ratio of PEG or other coating agent to cationic polymer for formulation of the PEG-PBAE co-polymer is equal to or greater than 2. In the nanoparticle formulated using a blended strategy the mass ratio of PEG to PBAE is equal to or greater than 0.5. The ratio by mass of PEG or other coating agent to cationic polymer can be 0.5, 1, 2, 3, 4, 5, 6, 7, 8, 9, 10, 11, 12, 13, 14 15, 16, 17, 18, 19, 20, 21, 22, 23, 24, 25, 26, 27, 28, 29, 30, 37, 50 or more than 50. In one embodiment, the density of the PEG or other coating agent is at least 0.001, 0.002, 0.005, 0.01, 0.02, 0.05, 0.1, 0.2, 0.5, 1, 2, 5, 10, 20, 50, or 100 units per $nm^2$.

2. Core Polymer

Any number of biocompatible polymers can be used to prepare the nanoparticles. In preferred embodiments, the biocompatible polymer(s) is a cationic polymer. Typically, the biocompatible polymer(s) is biodegradable.

i. Poly (β-Amino Ester)

In a preferred embodiment, the core polymer is poly (β-amino ester) (PBAE). PBAEs, when added to pH 5 buffer, are positively charged and can spontaneously form positively-charged nanoparticles (generally less than 200 nm) when added to negatively charged nucleic acid. They are taken up via endocytosis, and enable endosomal escape by buffering the endosome. PBAE can be readily degraded by hydrolysis of the ester bonds in the polymer backbone, enabling reduced cytotoxicity when compared to non-degradable controls. Modification of the polymer ends of PBAE can further improve transfection efficiency. Poly (β-amino ester) polymers can provide a non-toxic, biodegradable polymer library for the compaction of DNA, offering highly effective gene delivery in vitro even in cells that are hard to transfect.

PBAEs can be synthesized using semi-automated high-throughput combinatorial chemistry offering a large variety of polymers for the formulation of gene vectors with different properties. PBAE core polymers of different molecular weights can be used to formulate nanoparticle gene carriers. Representative PBAE polymers include PBAE with a molecular weight of 1 kilo-Dalton (1 kDa), 2 kDa, 3 kDa, 4 kDa, 5 kDa, 6 kDa, 8 kDa, 9 kDa 10 kDa, 11 kDa, 12 kDa, 13 kDa, 14 kDa, 15 kDa, and more than 15 kDa.

Methods for synthesizing PBAE of different molecular weights are known in the art. For example, PBAE can be synthesized by reacting 1,4-butanediol diacrylate and 4-amino-1-butanol at the molar ratios of 1.2:1 (PBAElow, MW~4 kDa), 1.1:1 (PBAEmid, MW~7 kDa) and 1.05:1 (PBAEhigh, MW~11 kDa) while stirring at 90° C. for 24 hours. Polymers can be precipitated and washed in cold ether and dried under vacuum. The molecular weights of the PBAE base polymers can be any methods known in eth art, including gel permeation chromatography and nuclear magnetic resonance spectroscopy.

ii. Other Polymers

Other polymers, including biodegradable and bioreducible polymers, may be used to produce the disclosed gene vectors. A representative list of polymers that can be used includes cyclodextrin-containing polymers, in particular cationic cyclodextrin-containing polymers, such as those described in U.S. Pat. No. 6,509,323, polyethylenimine (PEI), poly(L-lysine) (PLL), polymethacrylate, chitosan, poly(glycoamidoamine), schizophyllan, DEAE-dextran, dextran-spermine, poly(amido-amine) (PAA), poly(4-hydroxy-L-proline ester), poly[R-(4-aminobutyl)-L-glycolic acid] (PAGA), poly(amino-ester), poly(phosphazenes) (PPZ), poly(phosphoesters) (PPE), poly(phosphoramidates) (PPA), TAT-based peptides, Antennapedia homeodomain peptide, MPG peptide, poly(propylenimine), carbosilane, amine-terminated polyaminophosphine. In a particular embodiment the polymer is a cationic polymer with multiple free amines. Preferred polymers include polyethylenimine (PEI) and poly-L-lysine (PLL).

Copolymers of two or more polymers described above, including block and/or random copolymers, may also be employed to make the polymeric particles.

ii. Branched Polymers

In polymer chemistry, branching occurs by the replacement of a substituent, e.g., a hydrogen atom, on a monomer subunit, by another covalently bonded chain of that polymer; or, in the case of a graft copolymer, by a chain of another type. Branching may result from the formation of carbon-carbon or various other types of covalent bonds. Branching by ester and amide bonds is typically by a condensation reaction, producing one molecule of water (or HCl) for each bond formed.

The branching index measures the effect of long-chain branches on the size of a macromolecule in solution. It is defined as $g=<sb2>/<sl2>$, where sb is the mean square radius of gyration of the branched macromolecule in a given solvent, and sl is the mean square radius of gyration of an otherwise identical linear macromolecule in the same solvent at the same temperature. A value greater than 1 indicates an increased radius of gyration due to branching.

In preferred embodiments, the core polymer or PEG is a branched polymer that is capable of enhancing conjugation of the coating agent and core polymer. Exemplary branched polymers include 25 kDa branched polyethyleneimine (PEI) and 5 kDa branched methoxy-PEG.

iii. Copolymers

In preferred embodiments, copolymers of PEG or other coating agents with any of the polymers described above may be used to make the polymeric particles. In certain embodiments, the PEG or other coating agents may locate in the interior positions of the copolymer. Alternatively, the PEG or other coating agents may locate near or at the terminal positions of the copolymer. In certain embodiments, the nanoparticles are formed under conditions that allow regions of PEG other coating agents to phase separate or otherwise locate to the surface of the particles. For example, the surface-localized PEG regions alone may perform the function of, or include, a surface-altering agent.

3. Nucleic Acids

The disclosed nanoparticles are used for delivery of nucleic acid, including DNA, RNA, nucleic acid modified to increase resistance to nucleases and to increase stability, nucleic acid encoding or complementary to genes, and nucleic acid such as triple helix forming oligonucleotides which can be used to correct gene defects.

Nanoparticle gene carriers typically carry nucleic acids to alter, correct, or replace an endogenous nucleic acid sequence. In preferred embodiments, the nucleic acid is used to treat cancers, correct defects in genes in brain diseases, lung disorders such as cystic fibrosis and metabolic diseases affecting brain function, genes such as those for the treatment of Parkinsons and ALS.

Gene therapy is a technique for correcting defective genes responsible for disease development. Researchers may use one of several approaches for correcting faulty genes:

A normal gene may be inserted into a nonspecific location within the genome to replace a nonfunctional gene. This approach is most common.

An abnormal gene could be swapped for a normal gene through homologous recombination.

The abnormal gene could be repaired through selective reverse mutation, which returns the gene to its normal function.

The regulation (the degree to which a gene is turned on or off) of a particular gene could be altered.

The nucleic acid carried by the nanoparticle gene carrier can be a DNA, RNA, a chemically modified nucleic acid, or combinations thereof. Nucleic acids other than plasmid DNA, including mRNA, siRNA, miRNA, aptamers and oligonucleotides can also be incorporated into the nanoparticle vectors.

Methods for increasing stability of nucleic acid half-life and resistance to enzymatic cleavage are known in the art, and can include one or more modifications or substitutions to the nucleobases, sugars, or linkages of the polynucleotide. For example, the nucleic acid can be custom synthesized to contain properties that are tailored to fit a desired use. Common modifications include, but are not limited to, use of locked nucleic acids (LNAs), unlocked nucleic acids (UNAs), morpholinos, peptide nucleic acids (PNA), phosphorothioate linkages, phosphonoacetate linkages, propyne analogs, 2'-O-methyl RNA, 5-Me-dC, 2'-5' linked phosphodiester lineage, Chimeric Linkages (Mixed phosphorothioate and phosphodiester linkages and modifications), conjugation with lipid and peptides, and combinations thereof.

In some embodiments, the nucleic acid includes internucleotide linkage modifications such as phosphate analogs having achiral and uncharged intersubunit linkages (e.g., Sterchak, E. et al., *Organic Chem.*, 52:4202, (1987)), or uncharged morpholino-based polymers having achiral intersubunit linkages (see, e.g., U.S. Pat. No. 5,034,506). Some internucleotide linkage analogs include morpholidate, acetal, and polyamide-linked heterocycles. Other backbone and linkage modifications include, but are not limited to, phosphorothioates, peptide nucleic acids, tricyclo-DNA, decoy oligonucleotide, ribozymes, spiegelmers (containing L nucleic acids, an apatamer with high binding affinity), or CpG oligomers.

Phosphorothioates (or S-oligos) are a variant of normal DNA in which one of the non-bridging oxygens is replaced by sulfur. The sulfurization of the internucleotide bond dramatically reduces the action of endo- and exonucleases including 5' to 3' and 3' to 5' DNA POL 1 exonuclease, nucleases S1 and P1, RNases, serum nucleases and snake venom phosphodiesterase. In addition, the potential for crossing the lipid bilayer increases. Because of these important improvements, phosphorothioates have found increasing application in cell regulation. Phosphorothioates are made by two principal routes: by the action of a solution of elemental sulfur in carbon disulfide on a hydrogen phosphonate, or by the more recent method of sulfurizing phosphite triesters with either tetraethylthiuram disulfide (TETD) or 3H-1,2-bensodithiol-3-one 1, 1-dioxide (BDTD). The latter methods avoid the problem of elemental sulfur's insolubility in most organic solvents and the toxicity of carbon disulfide. The TETD and BDTD methods also yield higher purity phosphorothioates. (See generally Uhlmann and Peymann, 1990, Chemical Reviews 90, at pages 545-561 and references cited therein, Padmapriya and Agrawal, 1993, Bioorg. & Med. Chem. Lett. 3, 761).

Peptide nucleic acids (PNA) are molecules in which the phosphate backbone of oligonucleotides is replaced in its entirety by repeating N-(2-aminoethyl)-glycine units and phosphodiester bonds are replaced by peptide bonds. The various heterocyclic bases are linked to the backbone by methylene carbonyl bonds. PNAs maintain spacing of heterocyclic bases that is similar to oligonucleotides, but are achiral and neutrally charged molecules. Peptide nucleic acids are typically comprised of peptide nucleic acid monomers. The heterocyclic bases can be any of the standard bases (uracil, thymine, cytosine, adenine and guanine) or any of the modified heterocyclic bases described below. A PNA can also have one or more peptide or amino acid variations and modifications. Thus, the backbone constituents of PNAs may be peptide linkages, or alternatively, they may be non-peptide linkages. Examples include acetyl caps, amino spacers such as 8-amino-3,6-dioxaoctanoic acid (referred to herein as O-linkers), and the like. Methods for the chemical assembly of PNAs are well known. See, for example, U.S. Pat. Nos. 5,539,082, 5,527,675, 5,623,049, 5,714,331, 5,736,336, 5,773,571 and 5,786,571.

In some embodiments, the nucleic acid includes one or more chemically-modified heterocyclic bases including, but are not limited to, inosine, 5-(1-propynyl) uracil (pU), 5-(1-propynyl) cytosine (pC), 5-methylcytosine, 8-oxo-adenine, pseudocytosine, pseudoisocytosine, 5 and 2-amino-5-(2'-deoxy-β-D-ribofuranosyl)pyridine (2-aminopyridine), and various pyrrolo- and pyrazolopyrimidine derivatives, 4-acetylcytosine, 8-hydroxy-N-6-methyladenosine, aziridinylcytosine, 5-(carboxyhydroxylmethyl) uracil, 5-bromouracil, 5-carboxymethylaminomethyl-2-thiouracil, 5-carboxymethylaminomethyluracil, dihydrouracil, N6-isopentenyladenine, 1-methyladenine, 1-methylpseudouracil, 1-methyl guanine, 1-methylinosine, 2,2-dimethylguanine, 2-methyladenine, 2-methylguanine, 3-methylcytosine, N6-methyladenine, 7-methylguanine, 5-methylaminomethyluracil, 5-methoxy-aminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, 2,6-diaminopurine, and 2'-modified analogs such as, but not limited to O-methyl, amino-, and fluoro-modified analogs. Inhibitory RNAs modified with 2'-flouro (2'-F) pyrimidines appear to have favorable properties in vitro. 2'-F modified siRNAs may have enhanced activity in cell culture as compared to 2'-OH containing siRNAs. 2'-F modified siRNAs are functional in mice but that they do not necessarily have enhanced intracellular activity over 2'-OH siRNAs.

In some embodiments the nucleic acid includes one or more sugar moiety modifications, including, but not limited to, 2'-O-aminoethoxy, 2'-O-amonioethyl (2'-OAE), 2'-O-methoxy, 2'-O-methyl, 2-guanidoethyl (2'-OGE), 2'-O,4'-C-methylene (LNA), 2'-O-(methoxyethyl) (2'-OME) and 2'-O—(N-(methyl)acetamido) (2'-OMA).

Nanoparticle gene carriers carrying one or more nucleic acid can be utilized to deliver nucleic acid cargo in a method of gene therapy. Methods of gene therapy typically rely on the introduction into the cell of a nucleic acid molecule that alters the genotype of the cell. For example, corrective genes can be introduced into a non-specific location within the host's genome. This approach typically requires delivery systems to introduce the replacement gene into the cell, such as genetically engineered viral vectors.

In other embodiments, functional nucleic acids are introduced to prevent the function or expression of a particular gene that causes a defect or disease. Functional nucleic acids are nucleic acid molecules that have a specific function, such as binding a target molecule or catalyzing a specific reaction. For example, functional nucleic acids include, but are not limited to, antisense molecules, siRNA, miRNA, aptamers, ribozymes, triplex forming molecules, RNAi, and external guide sequences. The functional nucleic acid molecules can act as effectors, inhibitors, modulators, and stimulators of a specific activity possessed by a target molecule, or the functional nucleic acid molecules can possess a de novo activity independent of any other molecules.

Functional nucleic acid molecules can interact with any macromolecule, such as DNA, RNA, polypeptides, or carbohydrate chains. Thus, functional nucleic acids can interact with the mRNA or the genomic DNA of a target polypeptide or they can interact with the polypeptide itself. Often functional nucleic acids are designed to interact with other nucleic acids based on sequence homology between the target molecule and the functional nucleic acid molecule. In other situations, the specific recognition between the functional nucleic acid molecule and the target molecule is not based on sequence homology between the functional nucleic acid molecule and the target molecule, but rather is based on the formation of tertiary structure that allows specific recognition to take place.

In a particular embodiment, the inhibitory nucleic acids are antisense nucleic acids. Antisense molecules are designed to interact with a target nucleic acid molecule through either canonical or non-canonical base pairing. The interaction of the antisense molecule and the target molecule promotes the destruction of the target molecule through, for example, RNAseH mediated RNA-DNA hybrid degradation. Alternatively the antisense molecule interrupts a processing function that normally would take place on the target molecule, such as transcription or replication. Antisense molecules can be designed based on the sequence of the target molecule. Numerous methods for optimization of antisense efficiency by finding the most accessible regions of the target molecule exist. Exemplary methods would be in vitro selection experiments and DNA modification studies using DMS and DEPC. It is preferred that antisense molecules bind the target molecule with a dissociation constant ($K_d$) less than or equal to $10^{-6}$, $10^{-8}$, $10^{-10}$, or $10^{-12}$.

Aptamers are molecules that interact with a target molecule, preferably in a specific way. Typically aptamers are small nucleic acids ranging from 15-50 bases in length that fold into defined secondary and tertiary structures, such as stem-loops or G-quartets. Aptamers can bind small molecules, such as ATP and theophiline, as well as large molecules, such as reverse transcriptase and thrombin. Aptamers can bind very tightly with $K_d$'s from the target molecule of less than 10-12 M. It is preferred that the aptamers bind the target molecule with a $K_d$ less than $10^{-6}$, $10^{-8}$, $10^{-10}$, or $10^{-12}$. Aptamers can bind the target molecule with a very high degree of specificity. For example, aptamers have been isolated that have greater than a 10,000 fold difference in binding affinities between the target molecule and another molecule that differ at only a single position on the molecule. It is preferred that the aptamer have a $K_d$ with the target molecule at least 10, 100, 1000, 10,000, or 100,000 fold lower than the $K_d$ with a background binding molecule. It is preferred when doing the comparison for a polypeptide for example, that the background molecule be a different polypeptide.

Ribozymes are nucleic acid molecules that are capable of catalyzing a chemical reaction, either intramolecularly or intermolecularly. It is preferred that the ribozymes catalyze intermolecular reactions. There are a number of different types of ribozymes that catalyze nuclease or nucleic acid polymerase type reactions which are based on ribozymes found in natural systems, such as hammerhead ribozymes. There are also a number of ribozymes that are not found in natural systems, but which have been engineered to catalyze specific reactions de novo. Preferred ribozymes cleave RNA or DNA substrates, and more preferably cleave RNA substrates. Ribozymes typically cleave nucleic acid substrates through recognition and binding of the target substrate with subsequent cleavage. This recognition is often based mostly on canonical or non-canonical base pair interactions. This property makes ribozymes particularly good candidates for target specific cleavage of nucleic acids because recognition of the target substrate is based on the target substrates sequence. Triplex forming functional nucleic acid molecules are molecules that can interact with either double-stranded or single-stranded nucleic acid. When triplex molecules interact with a target region, a structure called a triplex is formed, in which there are three strands of DNA forming a complex dependent on both Watson-Crick and Hoogsteen base-pairing. Triplex molecules are preferred because they can bind target regions with high affinity and specificity. It is preferred that the triplex forming molecules bind the target molecule with a $K_d$ less than $10^{-6}$, $10^{-8}$, $10^{-10}$, or $10^{-12}$.

External guide sequences (EGSs) are molecules that bind a target nucleic acid molecule forming a complex, and this complex is recognized by RNase P, which cleaves the target molecule. EGSs can be designed to specifically target a RNA molecule of choice. RNAse P aids in processing transfer RNA (tRNA) within a cell. Bacterial RNAse P can be recruited to cleave virtually any RNA sequence by using an EGS that causes the target RNA:EGS complex to mimic the natural tRNA substrate. Similarly, eukaryotic EGS/RNAse P-directed cleavage of RNA can be utilized to cleave desired targets within eukarotic cells. Representative examples of how to make and use EGS molecules to facilitate cleavage of a variety of different target molecules are known in the art.

Gene expression can also be effectively silenced in a highly specific manner through RNA interference (RNAi). This silencing was originally observed with the addition of double stranded RNA (dsRNA) (Fire, A., et al. (1998) Nature, 391:806-11; Napoli, C., et al. (1990) Plant Cell 2:279-89; Hannon, G. J. (2002) Nature, 418:244-51). Once dsRNA enters a cell, it is cleaved by an RNase III-like enzyme, Dicer, into double stranded small interfering RNAs (siRNA) 21-23 nucleotides in length that contains 2 nucleotide overhangs on the 3' ends (Elbashir, S. M., et al. (2001) Genes Dev., 15:188-200; Bernstein, E., et al. (2001) Nature, 409:363-6; Hammond, S. M., et al. (2000) Nature, 404:293-6). In an ATP dependent step, the siRNAs become integrated into a multi-subunit protein complex, commonly known as the RNAi induced silencing complex (RISC), which guides the siRNAs to the target RNA sequence (Nykanen, A., et al. (2001) Cell, 107:309-21). At some point the siRNA duplex unwinds, and it appears that the antisense strand remains bound to RISC and directs degradation of the complementary mRNA sequence by a combination of endo and exonucleases (Martinez, J., et al. (2002) Cell, 110:563-74). However, the effect of iRNA or siRNA or their use is not limited to any type of mechanism.

Short Interfering RNA (siRNA) is a double-stranded RNA that can induce sequence-specific post-transcriptional gene silencing, thereby decreasing or even inhibiting gene expression. In one example, an siRNA triggers the specific degradation of homologous RNA molecules, such as mRNAs, within the region of sequence identity between both the siRNA and the target RNA. For example, WO 02/44321 discloses siRNAs capable of sequence-specific degradation of target mRNAs when base-paired with 3' overhanging ends, herein incorporated by reference for the method of making these siRNAs. Sequence specific gene silencing can be achieved in mammalian cells using synthetic, short double-stranded RNAs that mimic the siRNAs produced by the enzyme dicer (Elbashir, S. M., et al. (2001) Nature, 411:494 498) (Ui-Tei, K., et al. (2000) FEBS Lett. 479:79-82). siRNA can be chemically or in vitro-synthesized or can be the result of short double-stranded hairpin-like RNAs (shRNAs) that are processed into siRNAs inside the cell. Synthetic siRNAs are generally designed using algorithms and a conventional DNA/RNA synthesizer. Suppliers include Ambion (Austin, Tex.), ChemGenes (Ashland, Mass.), Dharmacon (Lafayette, Colo.), Glen Research (Sterling, Va.), MWB Biotech (Esbersberg, Germany), Proligo (Boulder, Colo.), and Qiagen (Vento, The Netherlands). siRNA can also be synthesized in vitro using kits such as Ambion's SILENCER® siRNA Construction Kit.

The production of siRNA from a vector is more commonly done through the transcription of a short hairpin RNAs (shRNAs). Kits for the production of vectors comprising shRNA are available, such as, for example, Imgenex's GENESUPPRESSOR™ Construction Kits and Invitrogen's BLOCK-IT™ inducible RNAi plasmid and lentivirus vectors.

An miRNA or pre-miRNA can be 18-100 nucleotides in length, and more preferably from 18-80 nucleotides in length. Mature miRNAs can have a length of 19-30 nucleotides, preferably 21-25 nucleotides, particularly 21, 22, 23, 24, or 25 nucleotides. MicroRNA precursors typically have a length of about 70-100 nucleotides and have a hairpin conformation.

Given the sequence of an miRNA or a pre-miRNA, an miRNA antagonist that is sufficiently complementary to a portion of the miRNA or a pre-miRNA can be designed according to the rules of Watson and Crick base pairing. As used herein, the term "sufficiently complementary" means that two sequences are sufficiently complementary such that a duplex can be formed between them under physiologic conditions. An miRNA antagonist sequence that is sufficiently complementary to an miRNA or pre-miRNA target sequence can be 70%, 80%, 90%, or more identical to the miRNA or pre-miRNA sequence. In one embodiment, the miRNA antagonist contains no more than 1, 2 or 3 nucleotides that are not complementary to the miRNA or pre-miRNA target sequence. In a preferred embodiment, the miRNA antagonist is 100% complementary to an miRNA or pre-miRNA target sequence. In some embodiments, the miRNA antagonist is complementary to a portion of the miRNA or pre-miRNA sequence of a human. Sequences for miRNAs are available publicly, for example, through the miRBase registry (Griffiths-Jones, et al., *Nucleic Acids Res.*, 36(Database Issue):D154-D158 (2008); Griffiths-Jones, et al., *Nucleic Acids Res.*, 36(Database Issue):D140-D144 (2008); Griffiths-Jones, et al., *Nucleic Acids Res.*, 36(Database Issue):D109-D111 (2008)) and other publically accessible databases.

In some embodiments, there will be nucleotide mismatches in the region of complementarity. In a preferred embodiment, the region of complementarity will have no more than 1, 2, 3, 4, or 5 mismatches.

In one embodiment, the miRNA antagonists are oligomers or polymers of ribonucleic acid (RNA) or deoxyribonucleic acid (DNA) or modifications thereof. miRNA antagonists include oligonucleotides that contain naturally-occurring nucleobases, sugars and covalent internucleoside (backbone) linkages.

In some embodiments, the miRNA antagonists are antagomirs. Antagomirs are a specific class of miRNA antagonists that are described, for example, in US2007/0213292 to Stoffel et al. Antagomirs are RNA-like oligonucleotides that contain various modifications for RNase protection and pharmacologic properties such as enhanced tissue and cellular uptake. Antagomirs differ from normal RNA by having complete 2'-O-methylation of sugar, phosphorothioate backbone and a cholesterol-moiety at 3'-end.

Antagomirs can include a phosphorothioate at least the first, second, or third internucleotide linkage at the 5' or 3' end of the nucleotide sequence. In one embodiment, antagomirs contain six phosphorothioate backbone modifications; two phosphorothioates are located at the 5'-end and four at the 3'-end. Phosphorothioate modifications provide protection against RNase activity and their lipophilicity contributes to enhanced tissue uptake.

Examples of antagomirs and other miRNA inhibitors are described in WO2009/020771, WO2008/091703, WO2008/046911, WO2008/074328, WO2007/090073, WO2007/027775, WO2007/027894, WO2007/021896, WO2006/093526, WO2006/112872, WO2007/112753, WO2007/112754, WO2005/023986, or WO2005/013901, all of which are hereby incorporated by reference.

Custom designed Anti-miR™ molecules are commercially available from Applied Biosystems. Thus, in some embodiments, the antagomir is an Ambion® Anti-miR™ inhibitor. These molecules are chemically modified and optimized single-stranded nucleic acids designed to specifically inhibit naturally occurring mature miRNA molecules in cells.

Custom designed Dharmacon Meridian™ microRNA Hairpin Inhibitors are also commercially available from Thermo Scientific. These inhibitors include chemical modifications and secondary structure motifs. For example, Vermeulen et al. reports in US2006/0223777 the identification of secondary structural elements that enhance the potency of these molecules. Specifically, incorporation of highly structured, double-stranded flanking regions around the reverse complement core significantly increases inhibitor function and allows for multi-miRNA inhibition at subnanomolar concentrations. Other such improvements in antagomir design are contemplated for use in the disclosed methods.

Methods to construct expression vectors containing genetic sequences and appropriate transcriptional and translational control elements are well known in the art. These methods include in vitro recombinant DNA techniques, synthetic techniques, and in vivo genetic recombination. Expression vectors generally contain regulatory sequences necessary elements for the translation and/or transcription of the inserted coding sequence. For example, the coding sequence is preferably operably linked to a promoter and/or enhancer to help control the expression of the desired gene product. Promoters used in biotechnology are of different types according to the intended type of control of gene expression. They can be generally divided into constitutive promoters, tissue-specific or development-stage-specific promoters, inducible promoters, and synthetic promoters.

Gene targeting via target recombination, such as homologous recombination (HR), is another strategy for gene correction. Gene correction at a target locus can be mediated by donor DNA fragments homologous to the target gene (Hu, et al., Mol. Biotech., 29:197-210 (2005); Olsen, et al., J. Gene Med., 7:1534-1544 (2005)). One method of targeted recombination includes the use of triplex-forming oligonucleotides (TFOs) which bind as third strands to homopurine/homopyrimidine sites in duplex DNA in a sequence-specific manner. Triplex forming oligonucleotides can interact with either double-stranded or single-stranded nucleic acids. When triplex molecules interact with a target region, a structure called a triplex is formed, in which there are three strands of DNA forming a complex dependent on both Watson-Crick and Hoogsteen base-pairing. Triplex molecules are preferred because they can bind target regions with high affinity and specificity. It is preferred that the triplex forming molecules bind the target molecule with a Kd less than 10-6, 10-8, 10-10, or 10-12.

Methods for targeted gene therapy using triplex-forming oligonucleotides (TFO's) and peptide nucleic acids (PNAs) are described in U.S. Published Application No. 20070219122 and their use for treating infectious diseases such as HIV are described in U.S. Published Application No. 2008050920. The triplex-forming molecules can also be tail clamp peptide nucleic acids (tcPNAs), such as those described in U.S. Published Application No. 2011/0262406. Highly stable PNA:DNA:PNA triplex structures can be formed from strand invasion of a duplex DNA with two PNA strands. In this complex, the PNA/DNA/PNA triple helix portion and the PNA/DNA duplex portion both produce displacement of the pyrimidine-rich triple helix, creating an altered structure that has been shown to strongly provoke the nucleotide excision repair pathway and to activate the site for recombination with the donor oligonucleotide. Two PNA strands can also be linked together to form a bis-PNA molecule. The triplex-forming molecules are useful to induce site-specific homologous recombination in mammalian cells when used in combination with one or more donor oligonucleotides which provides the corrected sequence. Donor oligonucleotides can be tethered to triplex-forming molecules or can be separate from the triplex-forming molecules. The donor oligonucleotides can contain at least one nucleotide mutation, insertion or deletion relative to the target duplex DNA.

Double duplex-forming molecules, such as a pair of pseudocomplementary oligonucleotides, can also induce recombination with a donor oligonucleotide at a chromosomal site. Use of pseudocomplementary oligonucleotides in targeted gene therapy is described in U.S. Published Application No. 2011/0262406. Pseudocomplementary oligonucleotides are complementary oligonucleotides that contain one or more modifications such that they do not recognize or hybridize to each other, for example due to steric hindrance, but each can recognize and hybridize to complementary nucleic acid strands at the target site. In some embodiments, pseudocomplementary oligonucleotides are pseudocomplemenary peptide nucleic acids (pcPNAs). Pseudocomplementary oligonucleotides can be more efficient and provide increased flexibility over methods of induced recombination such as triple-helix oligonucleotides and bis-peptide nucleic acids which require a polypurine sequence in the target double-stranded DNA.

The mass ratio of the nucleic acid to the core polymer within the nanoparticles can be at least 0.5, 1, 10, 60, 100, 1000 or more than 1000.

4. Additional Active Agents

Nanoparticle gene vectors may can carry only "genetic" materials. Other therapeutic, prophylactic and/or diagnostic agents can be co-delivered depending on the application. However, any "genetic" materials that can perform the listed functions can be packaged into the nanoparticles. For example, tumor suppressor genes such as p53 and Rb can be complexed into nanoparticles to be used for cancer patients, so as any plasmid DNA or siRNA that possess anti-inflammatory, anti-viral functions, etc.

These additional active agents can be dispersed in the nanoparticle gene carriers or be covalently attached to one or more of the polymeric components of the nanoparticle.

Suitable additional active agents include, but are not limited to, other nucleic acid-based medicine, anti-inflammatory drugs, antiproliferatives, chemotherapeutics, vasodilators, and anti-infective agents. In certain embodiments, the nanoparticle gene carriers contain one or more antibiotics, such as tobramycin, colistin, or aztreonam. The disclosed nanoparticle gene carriers can optionally contain one or more antibiotics which are known to possess anti-inflammatory activity, such as erythromycin, azithromycin, or clarithromycin. Nanoparticles may also be used for the delivery of chemotherapeutic agents, and anti-proliferative agents.

Nanoparticle gene carriers can carry only "genetic" materials. Others can be co-delivered depending on the application. However, any "genetic" materials that can perform the listed functions can be packaged into the nanoparticles. For example, tumor suppressor genes such as p53 and Rb can be complexed into nanoparticles to be used for cancer patients, so as any plasmid DNA or siRNA that possess anti-inflammatory, anti-viral functions, etc.

The disclosed nanoparticle gene carriers can optionally contain one or more additional, non-nucleic acid active agents. The one or more additional active agents can be dispersed in the nanoparticle gene carriers or be covalently attached to one or more of the polymeric components of the nanoparticle.

Suitable additional active agents include, but are not limited to, other nucleic acid-based medicine, anti-inflammatory drugs, antiproliferatives, chemotherapeutics, vasodilators, and anti-infective agents. In certain embodiments, the nanoparticle gene carriers contain one or more antibiotics, such as tobramycin, colistin, or aztreonam. The disclosed nanoparticle gene carriers can optionally contain one or more antibiotics which are known to possess anti-inflammatory activity, such as erythromycin, azithromycin, or clarithromycin. Nanoparticles may also be used for the delivery of chemotherapeutic agents, and anti-proliferative agents.

5. Nanoparticle Properties

As shown in the examples, the disclosed nanoparticles diffuse through the pores of the airway mucus (and are referred to as mucus penetrating nanoparticles, MPP) or the extracellular matrix ("ECM") of the brain (and are referred to as brain penetrating nanoparticles, or BPN) at a greater rate of diffusivity than a reference nanoparticle, such as an uncoated particle, e.g., uncoated PEI and PBAE particles, or a conventionally coated nanoparticle (CP), e.g., PEGylated PLL particles (PLL-CP). The gene vectors can stably retain their physicochemical characteristics over at least a week in aqueous solution and post-lyophilization, and are highly stable in physiological solutions. Moreover, they demonstrate the ability to penetrate physiological barriers such as airway mucus and brain tissue/tumor allowing for widespread distribution and high level transgene expression in vivo. These advantages provide the opportunity to expand this highly efficient, tailorable and biodegradable gene delivery platform in vivo and render it more compatible with clinical applications.

i. Particle Diffusivity

The transport rates of the particles can be measured using a variety of techniques in the art. In one embodiment, the rate of diffusion is measured by geometric ensemble mean squared displacements (MSD). In a particular embodiment, the particles may diffuse through the pores of the the of the airway mucus with an MSD that is at least 10, 20, 30, 50, 60, 80, 100, 125, 150, 200, 250, 500, 600, 750, 1000, 1500, 2000, 2500, 3000, 4000, 5000, 10000- or greater fold higher than a reference particle. In a particular embodiment, the particles may diffuse through the pores of the of the ECM of the brain with an MSD that is at least 9, 10, 20, 30, 50, 60, 80, 100, 125, 150, 200, 250, 500, 600, 750, 1000, 1500, 2000, 2500, 3000, 4000, 5000, 10000- or greater fold higher than a reference particle.

In other embodiments, the disclosed nanoparticles diffuse through the pores of the ECM of the brain at a rate approaching the rate of diffusivity at which the particles diffuse through water. In a particular embodiment, the rate of diffusivity is at least $1/1000$, $1/800$, $1/700$, $1/600$, $1/500$, $1/400$, $1/250$, $1/200$, $1/150$, $1/100$, $1/75$, $1/50$, $1/25$, $1/10$, $1/7$, $1/5$, $1/2$, or 1 times the rate of diffusivity of the particle in water under identical conditions. For example, at a time scale of 1 s, the rates of diffusion of unmodified or reference particles can be slower in brain tissue than the same particles in water.

The density of coating of PEG or other material can affect the diffusion of nanoparticle within the airway mucus or the brain parenchyma. In some embodiments the MSD at 1 sec of densely PEGylated particles in airway mucus is at least 12-fold greater than that of less-densely PEGylated PLL particles, or at least 15-fold higher than that of non-PEGylated PEI particles. The MSD at 1 sec of densely PEGylated particles in the brain parenchyma is at least 10 fold higher than that of non-PEGylated PBAE particles.

The heterogeneity in particle transport rates can also be evaluated by examining the distribution of individual particle diffusivities over a particular time period, e.g., 1 s.

The particles can be classified based on their mode of transport: diffusive, hindered, or immobile. In one embodiment, PEI and PEG-PLL are strongly hindered with constrained non-Brownian time-lapse traces, in airway mucus. In contrast, PEG-PBAE trajectories spanned over greater distances indicating unhindered diffusion in CF sputum. Defining rapidly moving gene vectors by log 10 MSD≥−1 at least half of PEG-PBAE gene vectors were able to efficiently penetrate CF sputum, whereas only 12.2% of PEI and 18.2% of PEG-PLL could do so. In the brain parenchyma, PEG-PBAE trajectories spanned over greater distances, indicating the unhindered diffusion in brain tissue, the non-PEGylated nanoparticles were strongly hindered in the brain parenchyma with constrained non-Brownian time-lapse traces. Defining rapidly moving gene vectors by log 10 MSD≥−1, it was observed that 65% of PEG-PBAE could rapidly penetrate the brain in comparison to only 19% of PBAE. In some embodiments, at least 15%, 20%, 25%, 30%, 35%, 40%, 45%, 50%, 55%, 60%, 65%, 70%, 75%, 80%, or greater of coated particles of a given average particle size are classified as diffusive.

ii. Electro-Kinetic Potential

The presence of the PEG or coating agent can affect the zeta-potential of the particle. In one embodiment, the zeta potential of the particles is between −10 mV and 100 mV, between −10 mV and 50 mV, between −10 mV and 25 mV, between −5 mV and 20 mV, between −10 mV and 10 mV, between −10 mV and 5 mV, between −5 mV and 5 mV, or between −2 mV and 2 mV. In a preferred embodiment, the surface charge is near neutral.

iii. Particle Size

In some embodiments, the disclosed nanoparticles have an average diameter equal to or smaller than the pores in the brain ECM and airway mucus. Particle size can be measured using any technique known in the art, for example using dynamic light scattering.

In another embodiment, the particles have an average diameter such that a majority of the particles do not become localized within cells or micro-domains within tissue compared to larger particles. As shown in the Table 1, particles having an average particle size of 50 nm showed a larger MSD at 1 sec when densely PEGylated, as measured using multiple particle tracking (MPT) of fluorescently labeled gene vectors in rodent brain.

iv. Toxicity

The disclosed nanoparticles densely-coated with PEG or other coating agents are less toxic than non-coated particles. The in vitro or in vivo toxicity of nanoparticles can be assessed using any technique known in the art, such as histopathological assessment and BALF cell count. In one embodiment, the densely PEGylated biodegradable nanoparticles demonstrate significantly lower toxicity in vivo than non-PEGylated PEI nanoparticles and similar safety profiles as clinically tested PEG-PLL.

B. Pharmaceutical Formulations

The particles may be administered in combination with a physiologically or pharmaceutically acceptable carrier, excipient, or stabilizer. The term "pharmaceutically acceptable" means a non-toxic material that does not interfere with the effectiveness of the biological activity of the active ingredients. The term "carrier" refers to an organic or inorganic ingredient, natural or synthetic, with which the active ingredient is combined to facilitate the application.

Pharmaceutical compositions may be formulated in a conventional manner using one or more physiologically acceptable carriers including excipients and auxiliaries which facilitate processing of the active compounds into preparations which can be used pharmaceutically. Proper formulation is dependent upon the route of administration chosen. In preferred embodiments, the particles are formulated for parenteral delivery to the brain. Typically the particles will be formulated in sterile saline or buffered solution for injection into the tissues or cells to be treated. The particles can be stored lyophilized in single use vials for rehydration immediately before use. Other means for rehydration and administration are known to those skilled in the art.

Formulations contain an effective amount of nanoparticle carriers in a pharmaceutical carrier appropriate for administration to a mucosal surface. Pharmaceutical formulations and methods for the pulmonary administration of active agents to patients are known in the art. Pharmaceutical formulations can be administered to any mucosal surface in a patient to treat or lessen one or more symptoms. Generally, the formulations are administered to the pulmonary tract. Aerosolized pharmaceutical formulations can be delivered to the lungs, preferably using a device, such as a dry powder inhaler, nebulizer, or pressurized metered dose inhaler (pMDI). Liquid formulations can also be administered to the respiratory tract by other suitable methods such as intranasal instillation, intratracheal instillation, and intratracheal injection. The formulations can also be administered to other mucosal surfaces including nasal, buccal, rectal and vaginal surfaces.

The respiratory tract is the structure involved in the exchange of gases between the atmosphere and the blood stream. The respiratory tract encompasses the upper airways, including the oropharynx and larynx, followed by the lower airways, which include the trachea followed by bifurcations into the bronchi and bronchioli. The upper and lower airways are called the conducting airways. The terminal bronchioli then divide into respiratory bronchioli which then lead to the ultimate respiratory zone, the alveoli, or deep lung, where the exchange of gases occurs.

Formulations can be divided into dry powder formulations and liquid formulations. Both dry powder and liquid formulations can be used to form aerosol formulations. The term aerosol as used herein refers to any preparation of a fine mist of particles, which can be in solution or a suspension, whether or not it is produced using a propellant.

II. Methods of Manufacture

Methods for formulating sub-100 nm, compact, colloidally stable PBAE gene carriers that have a dense surface coverage of hydrophilic and neutrally charged PEG (PEG-PBAE) are disclosed. The formulation methods are highly tailorable and thus can be applied to various biodegradable and bioreducible cationic polymers. As previously reported, PEGylation of cationic polymers may have negative influences on DNA complexation due to reduction of available positive charges resulting from the PEG conjugation to the amine groups of cationic polymers and additional steric hindrance imposed by grafted PEG chains. The technique of incorporating a non-PEGylated polymer core to allow compact DNA complexation was used to overcome this limitation and achieve dense PEG surface coating. Achieving effective DNA compaction using a mixture of PEGylated and non-PEGylated PBAE required thorough characterization and careful optimization of formulation parameters including but not limited to polymer/DNA weight ratio, PBAE-PEG/PBAE ratio, pH of DNA and polymer solutions, type of buffering solution and method of mixing.

The disclosed formulation methods can be applied to various biodegradable and bioreducible cationic polymers.

A. Polymer Preparation

The polymers can be synthesized by any means known in the art. PEG or other coating agents can be conjugated to the core polymer using a variety of techniques known in the art depending on whether the coating is covalently or non-covalently associated with the particles.

In some embodiments the PEG or other coating agent can be covalently attached to the core polymer by reacting functional groups on the particles with reactive functional groups on the PEG or other coating agent to make a copolymer. For example, PEG-succinimidyl succinate can be reacted with primary amine groups to covalently attach the agent via an amide bond.

In one embodiment, polyethylene glycol (PEG)-conjugated poly(β-amino ester) (PBAE) (PBAE-PEG) polymer is synthesized by a two-step reaction from the uncapped base PBAElow polymers: end diacrylate group capping and purification can be conducted using with 1,3-diaminopropane; subsequently, the end capped PBAE polymers and 2.05 molar excess of 5 kDa methoxy-PEG-N-hydroxysuccinimide can be mixed, vacuumed and purged with nitrogen. The extent of PEGylation of the resulting PBAE copolymer can be varied by varying the molar ratio of PEG added to the PBAE.

B. Nanoparticles

The disclosed nanoparticle gene carriers can be formed from one or more cationic polymers, one or more PEGs or other coating agents, and one or more nucleic acids using any suitable method for the formation of polymer nanoparticles known in the art.

Methods of making nanoparticles densely coated with polyethylene glycol that are optimized for the delivery of nucleic acids across biological barriers are provided. Factors that can influence the physicochemical properties of the nanoparticles can include: the molar ratio of free polymer and polymer conjugated to PEG within the blended polymer; the mass ratio of nucleic acid to blended polymer; the volume ratio of nucleic acid added to the polymer; the rate at which the nucleic acid and polymer are combined, and the concentration ratio of the nucleic acid to the polymer.

1. Composition of the Blended Polymer

In some embodiments nanoparticles are formed of a mixture of PEGylated and non-pegylated ("free") polymers, such as charged polymers. The blended free and PEG-conjugated polymer mixture can retain a charge that is useful for enhancing conjugation with nucleic acid, as compared to polymers that contain 100% PEG conjugated polymer, or 100% free polymer. In some embodiments the use of a free polymer/PEGylated polymer blend enables formation of a compact nanoparticle that has a smaller hydrodynamic radius and is more stable than a reference particle. The non-PEGylated polymers can contribute a defined amount of the total free amines, such as 5%, 10%, 15%, 20%, 25%, 30%, 35%, 40%, 45%, 50% or more than 50% of the total free amines in the particles. In some embodiments, the ratio of non-PEGylated polymers to PEGylated polymers is optimized for colloidally stable nanoparticles with a diameter less than 100 nm and a near neutral surface charge. The blended polymer can contain a molar ratio of free polymer to polymer conjugated with polyethylene glycol of between 0.5 and 1, or more than 1. In a particular embodiment the blended polymer contains a molar ratio of free polymer to polymer conjugated with polyethylene glycol of 0.67.

2. The Ratio of Nucleic Acid to Blended Polymer

In some embodiments nanoparticles are formed using a mass:mass ratio of the blended polymer to the nucleic acid that is optimized for producing colloidally stable nanoparticles with a diameter less than 100 nm and a near neutral surface charge. Typically, the mass:mass ratio of the blended polymer to the nucleic acid is up to 1:1,000, such as 1 to 500, 1 to 100, or 1 to less than 100, such as 1:60.

In further embodiments nanoparticles are formed using a volume:volume ratio of nucleic acid solution added to polymer solution that is optimized for producing colloidally stable nanoparticles with a diameter less than 100 nm and a near neutral surface charge. In certain embodiments up to 10 volumes of nucleic acid are added to one volume of blended polymer. In a particular embodiment, 5 volumes of DNA solution is added to one volume of polymer solution.

The rate at which the nucleic acid is added to the polymer solution can also influence the physicochemical properties of the nanoparticles. In some embodiments the nucleic acid is added to the polymer at a steady rate of up to 10 ml/min. In one embodiment the nucleic acid is added to the polymer at a rate of 1 ml/min.

The concentration of the blended polymer can be up to 2,000 times the concentration of the nucleic acid, such as up to 300 times. In some embodiments, the concentration of the blended polymer is about 100 mg/ml and the concentration of the nucleic acid is about 0.1 mg/ml.

The concentration of the nucleic acid solution that can be used is 0.01, 0.05, 0.1, 0.2 or greater than 0.2 mg/ml up to 1 mg/ml. 0.1 mg/ml concentration of nucleic acid is preferred.

In circumstances where a monodisperse population of particles is desired, the particles may be formed using a method which produces a monodisperse population of nanoparticles. Alternatively, methods producing polydisperse nanoparticle distributions can be used, and the particles can be separated using methods known in the art, such as sieving, following particle formation to provide a population of particles having the desired average particle size and particle size distribution.

Methods of making polymeric particles are known in the art. Common microencapsulation techniques include, but are not limited to, spray drying, interfacial polymerization, hot melt encapsulation, phase separation encapsulation (spontaneous emulsion microencapsulation, solvent evaporation microencapsulation, and solvent removal microencapsulation), coacervation, low temperature microsphere formation, and phase inversion nanoencapsulation (PIN). A brief summary of these methods is presented below.

Pharmaceutically acceptable excipients, including pH modifying agents, disintegrants, preservatives, and antioxidants, can optionally be incorporated into the particles during particle formation. As described above, one or more additional active agents can also be incorporated into the nanoparticle gene carrier during particle formation.

1. Phase Separation Microencapsulation

In phase separation microencapsulation techniques, a polymer solution is stirred, optionally in the presence of one or more active agents to be encapsulated. While continuing to uniformly suspend the material through stirring, a non-solvent for the polymer is slowly added to the solution to decrease the polymer's solubility. Depending on the solubility of the polymer in the solvent and nonsolvent, the polymer either precipitates or phase separates into a polymer rich and a polymer poor phase. Under proper conditions, the polymer in the polymer rich phase will migrate to the interface with the continuous phase, encapsulating the active agent(s) in a droplet with an outer polymer shell.

2. Spontaneous Emulsion Microencapsulation

Spontaneous emulsification involves solidifying emulsified liquid polymer droplets formed above by changing temperature, evaporating solvent, or adding chemical cross-linking agents. The physical and chemical properties of the encapsulant, as well as the properties of the one or more active agents optionally incorporated into the nascent particles, dictates suitable methods of encapsulation. Factors such as hydrophobicity, molecular weight, chemical stability, and thermal stability affect encapsulation.

3. Solvent Evaporation Microencapsulation

Methods for forming microspheres using solvent evaporation techniques are described in E. Mathiowitz et al., J. Scanning Microscopy, 4:329 (1990); L. R. Beck et al., Fertil. Steril., 31:545 (1979); L. R. Beck et al, Am. J Obstet. Gynecol., 135(3) (1979); S. Benita et al., J. Pharm. Sci., 73:1721 (1984); and U.S. Pat. No. 3,960,757 to Morishita et al. The polymer is dissolved in a volatile organic solvent, such as methylene chloride. One or more active agents to be incorporated are optionally added to the solution, and the mixture is suspended in an aqueous solution that contains a surface active agent such as poly(vinyl alcohol). The resulting emulsion is stirred until most of the organic solvent evaporated, leaving solid microparticles/nanoparticles. This method is useful for relatively stable polymers like polyesters and polystyrene.

4. Phase Inversion Nanoencapsulation (PIN)

Nanoparticles can also be formed using the phase inversion nanoencapsulation (PIN) method, wherein a polymer is dissolved in a "good" solvent, fine particles of a substance to be incorporated, such as a drug, are mixed or dissolved in the polymer solution, and the mixture is poured into a strong non solvent for the polymer, to spontaneously produce, under favorable conditions, polymeric microspheres, wherein the polymer is either coated with the particles or the particles are dispersed in the polymer. See, e.g., U.S. Pat. No. 6,143,211 to Mathiowitz, et al. The method can be used to produce monodisperse populations of nanoparticles and microparticles in a wide range of sizes, including, for example, about 100 nanometers to about 10 microns.

5. Microfluidics

Nanoparticles can be prepared using microfluidic devices. A polymeric material is mixed with a drug or drug combinations in a water miscible organic solvent. The water miscible organic solvent can be one or more of the following: acetone, ethanol, methanol, isopropyl alcohol, acetonitrile and Dimethyl sulfoxide (DMSO). The resulting mixture solution is then added to an aqueous solution to yield nanoparticle solution.

Other methods known in the art that can be used to prepare nanoparticles include, but are not limited to, polyelectrolyte condensation (see Suk et al., Biomaterials, 27, 5143-5150 (2006)); single and double emulsion (probe sonication); nanoparticle molding, and electrostatic self-assembly (e.g., polyethylene imine-DNA or liposomes).

III. Methods of Use

The disclosed nanoparticles with a neutral surface charge and hydrodynamic diameter of less than 100 nm can be used to deliver nucleic acids across biological barriers such as the mucosa and the brain extracellular matrix ("ECM"). Effective gene delivery requires widespread distribution and high level transgene expression. The diffusion limitation of PBAE-PEG nanoparticles was investigated ex vivo, in excised rodent brain slices, as described in the Examples. Using multiple-particle tracking (MPT) and optimized PEGylation protocols, it was shown that differences in PEG coating density have a significant impact on shielding particles from adhesive interactions and enabling them to penetrate and distribute more uniformly in vivo. Therefore, the nanoparticle gene carriers can be used to deliver nucleic acids across biological barriers to treat one or more diseases or disorders.

A. Therapeutic Uses

The physicochemical properties of the disclosed nanoparticle allow for unhindered diffusion throughout various biological barriers to achieve enhanced penetration and delivery of nucleic acids.

Many debilitating diseases and disorders are caused by gene deletion or mutations. Methods of gene therapy typically rely on the introduction into the cell of a nucleic acid molecule that alters the genotype of the cell. Thus, nanoparticle gene carriers carrying nucleic acids have a wide variety of therapeutic and prophylactic uses. The nanoparticle gene carriers can be utilized to deliver nucleic acid cargo for therapeutic or prophylactic purposes, such as in a method of gene therapy.

1. Disorders or Diseases to be Treated

The disclosed nanoparticle gene carriers carrying one or more nucleic acid can be utilized to deliver nucleic acid cargo across biological barriers. Exemplary biological barriers include the extracellular matrix (ECM), tumor tissues and mucous gel lining, such as the mucous lining the respiratory tract.

i. Central Nervous System

The disclosed nanoparticle gene carriers carrying one or more nucleic acid can be utilized to deliver nucleic acid cargo through the blood/brain barrier (BB) and throughout the ECM of the brain parenchyma.

The central nervous system (CNS), as a target for gene therapy, presents multiple practical advantages for intervention. The existence of numerous genetic targets that can alter the natural history of CNS diseases renders gene therapy an attractive approach for the development of treatments. Effective gene delivery requires widespread distribution and high level transgene expression. However, the anisotropic and electrostatically charged extracellular matrix (ECM) found between brain cells creates a 'brain tissue barrier' which, regardless of administration method, hampers widespread distribution of nanoparticles in the brain (WO 2012/039979 A2).

Exemplary diseases and disorders of the brain that can be treated by the disclosed compositions and methods include neoplasms (cancers, tumors, growths), infections (HIV/AIDS), inflammation (multiple sclerosis, transverse myelitis and other autoimmune processes, cerebral or tissue edema and other reactive processes), acquired or degenerative conditions (Alzheimer's disease, Parkinson's disease, stroke, amylotrophic lateral sclerosis, acute and chronic traumatic and pain syndromes), congenital or genetic abnormalities (neurofibromatosis, mucopolysaccaridoses, tuberous sclerosis, Von Hippel Lindau), epigenetic conditions and brain trauma or injury.

ii. Respiratory System

The disclosed nanoparticle gene carriers can be utilized to deliver nucleic acid cargo across the airway mucus. A number of viral and non-viral gene delivery systems have been developed and for the treatment of pulmonary disorders, including cystic fibrosis, chronic obstructive pulmonary disease and asthma. Viral gene therapy has been extensively tested in clinical trials. However, immunogenicity, safety concerns, and inefficient gene transfer has limited their success. Non-viral gene delivery offers an alternative strategy to overcome these limitations. However, the adhesive and viscoelastic mucus gel covering the airway epithelium traps gene vectors, both viral and non-viral, and the gel layer is subsequently removed from the lung airways via mucociliary clearance mechanism, preventing the delivery of DNA payload to the underlying cells. The physicochemical characteristics of the PEG-PBAE gene vectors formulated by these methods provide remarkable colloidal stability and muco-inert PEG surface coverage, and thus allow these gene vectors to rapidly penetrate human airway mucus, homogeneously distribute in the lung airways and leads to high level sustained transgene expression compared to conventional gene carriers, including a system tested in a clinical trial. Importantly, storage in aqueous solutions (regardless of hydrolytic nature of PBAE), lyophilization or repeated administrations do not reduce the transfection efficiency of PEG-PBAE.

Exemplary diseases and disorders of the respiratory tract that can be treated by the disclosed compositions and methods include Cystic fibrosis (CF). Cystic fibrosis (CF) is an autosomal recessive genetic disease caused by mutations in the cystic fibrosis transmembrane regulator (CFTR) gene, which encodes for an apical membrane epithelial protein that functions as a regulator of several channels, including the c-AMP-regulated chloride channel. Patients with suffering from CF produce excessive quantities of abnormally viscous mucus, which blocks the patient's bronchi and readily becomes infected. As a result, CF patients are stricken with chronic respiratory infections, including *Pseudomonas* infections, causing inflammation, progressive airway damage, and bronchiectasis.

A non-limiting list of other diseases and disorders of the respiratory tract that can be treated by the disclosed compositions and methods include neoplasms (cancers, tumors, growths), infections (Tuberculosis), inflammation (autoimmune processes, tissue edema and other reactive processes), acquired or degenerative conditions, congenital or genetic abnormalities (cystic fibrosis neurofibromatosis, mucopolysaccaridoses, tuberous sclerosis), epigenetic conditions and lung trauma or injury.

iii. Other Mucus Covered Epithelial Surfaces

The disclosed nanoparticle gene carriers carrying one or more nucleic acid can be utilized to deliver nucleic acid cargo across the mucosa linings throughout the body.

Exemplary mucous-lined epithelial surfaces include the urogenital tract, the gastro-intestinal tract, the ocular cavities, the oral cavity as well as mucosal linings of the ears, eyes, nose or throat.

Exemplary diseases and disorders of the urogenital tract include infections (bacterial vaginosis (BV), cystitis, pyelonephritis, prostatitis, urethritis, renal candidiasis, candidal urethritis, urethral obstruction, inflammatory vaginitis, pelvic inflammatory disease, cervicitis, trichomoniasis (such as Trichomal vaginitis) mucopurulent cervicitis, Lymphogranuloma Venereum (LGV), nongonococcal urethritis, Chancroid, *Chlamydia*, Gonorrhea, gonococcal urethritis, Granuloma inguinale, Syphilis, Candidiasis, Viral hepatitis, Herpes simplex (HSV), Human Immunodeficiency Virus (HIV), Human Papillomavirus (HPV) and Molluscum contagiosum) and complications thereof.

Exemplary diseases and disorders of the gastrointestinal tract include gastroenteritis and irritable bowel syndrome (IBS), diarrhea, dysentery, cholera, hemorrhagic colitis, peptic ulcer disease, gastritis, and enteric fever (e.g., typhoid fever), viral infections including adenoviruses, hepatitis E virus, astroviruses, noroviruses and other caliciviruses, reoviruses and rotaviruses.

Exemplary diseases and disorders or infection of the oral cavity can be caused by fungal, viral or bacterial infection in the mouth (including inflammatory disorders, gingivitis, mucosal lesions, odontogenic and periodontal diseases such as dental caries) and viral disease (herpes labialis (cold sores or fever blisters), herpes genitalis, herpes zoster (shingles), varicella zoster (chickenpox).

Exemplary infections of the ears include chronic or acute otitis externa (swimmer's ear), conditions associated with the breakdown of the cerumen, Erysipelas of the concha and/or ear canal.

Exemplary diseases and disorders of the throat include acute pharyngitis, infectious mononucleosis (also known as Epstein-Barr virus), Anaerobic pharyngitis (also known as Vincent's angina), Peritonsillar abscess (also known as quinsy), thrombophlebitis (Lemierre syndrome), Tularemia, Kawasaki syndrome and acute laryngitis.

Exemplary diseases and disorders of the eyes include bacterial conjunctivitis, viral conjunctivitis, (caused by, for example, adenoviruses, herpes simplex viruses enteroviruses and Coxsackievirus), fungal conjunctivitis, parasitic conjunctivitis, keratitis (corneal ulcer), scleritis, keratoconjunctivitis, Iritis, uveitis, ocular lymphogranuloma venereum, trachoma and endophthalmitis. A variety of genetic diseases in the retina, including retinitis pigmentosa and leber congenital amaurosis, might be excellent targets for gene delivery as treatment.

iv. Tumor Tissue

The disclosed nanoparticles efficiently penetrate tumor tissue and can be used to deliver nucleic acid cargo into and throughout tumors.

Cells undergoing unregulated growth, invasion, or metastasis are generally referred to as cancerous, neoplastic or transformed cells. Typically, the growth of a cancerous or neoplastic cell exceeds and is not coordinated with that of the normal, non-cancerous tissues around it. The growth can persist in the same excessive manner even after cessation of a pro-proliferative stimuli, and typically causes formation of a tumor. Neoplasms may be benign, pre-malignant or malignant. In some embodiments nanoparticle gene carriers are effective to deliver nucleic acid cargo to tumor tissue to prevent, reduce, inhibit, or delay one or more symptoms of a cancer in a subject.

A representative list of cancers that the disclosed nanoparticles can be used to penetrate and treat include cancers of the genitourinary system (including prostate cancer, bladder cancer, renal cancer, urethral cancer, penile cancer, testicular cancer), cancers of the nervous system (including meningiomas, gliomas, glioblastomas, ependymomas) cancers of the head and neck (including squamous cell carcinomas of the oral cavity, nasal cavity, nasopharyngeal cavity, oropharyngeal cavity, larynx, and paranasal sinuses), lung cancers (including small cell and non-small cell lung cancer), gynecologic cancers (including cervical cancer, endometrial cancer, vaginal cancer, vulvar cancer ovarian and fallopian tube cancer), gastrointestinal cancers (including gastric, small bowel, colorectal, liver, hepatobiliary, and pancreatic cancers), skin cancers (including melanoma, squamous cell carcinomas, and basal cell carcinomas), breast cancer (including ductal and lobular cancer), and pediatric cancers (including neuroblastoma, Ewing's sarcoma, Wilms tumor, medulloblastoma), as well as breast cancer, ovarian cancer and prostate cancer.

B. Methods of Administration and Dosing

The nanoparticles can be administered by a variety of routes of administration. In certain embodiments the particles are administered directly to the brain. In other embodiments the particles are administered systemically.

The composition of the brain ECM, including the physicochemical properties of its components and the space between them ('pores'), are key factors that determine the penetration of substances within the brain.

Unshielded, positively charged particles with exposed hydrophobic regions have significantly hindered diffusion regardless of particle size. The hydrophobic interactions between particle surfaces and ECM components can be a source of significant adhesion. Adequate surface shielding from potential interactions, including electrostatic and hydrophobic forces, are crucial for rapid diffusion in the brain.

Mechanisms for the enhanced delivery of the disclosed nanoparticles to the brain are disclosed. Enhanced local delivery can be achieved via convection, electromagnetic, or other forces. Enhanced systemic delivery can be achieved via co- or sequential administration with permeabliization agents such as but not limited to pharmacologic substances (e.g. cytokines), mechanical barrier disruption (e.g. ultrasound), or osmotic changes (e.g. mannitol). Other methods of delivery include intrathecal or intra-ventricular delivery via cerebro-spinal fluid spaces, intra-nasal administration or delivery via the olfactory bulb and systemic delivery via oral, intravenous, or intra-arterial administration.

1. Convection Enhanced Delivery

In some embodiments the brain penetrating capability of the disclosed nanoparticles is enhanced following convection enhanced delivery (CED). The properties of the disclosed nanoparticles can drastically enhance their distribution in the CNS following CED, allowing for widespread transgene expression.

CED has been designed to overcome some of the difficulties so that pharmacological agents that would not normally cross the BBB can be used for treatment. CED is a method in which drugs are delivered through a needle installed intraparenchymally into the brain and attached to a pump providing positive pressure and constant flow of the infusates. For example, densely PEGylated nanoparticles drugs can be delivered through one to several catheters placed stereotactically, for example, directly within a brain tumor mass or around the tumor or the resection cavity.

In some embodiments CED can significantly enhance distribution of varied-size molecules and increase the infused compounds' locoregional concentration. In certain embodiments the use of CED to deliver densely PEGylated particles enhances the distribution of the particles throughout the brain to an extent that is greater than the expected increase. In some embodiments gene vector distribution and high-level transgene expression can be achieved throughout the entire striatum. CED is unlikely to provide a significant benefit if particles remain entrapped in the brain parenchyma due to adhesive interactions and/or steric obstruction. Thus, physicochemical properties of particles that allow unhindered diffusion in the brain parenchyma remain critical for achieving enhanced particle penetration following the CED.

Nanoparticles may be infused in different solutions that have been shown to further enhance gene vector distribution in the brain. In some embodiments the gene vectors can be administered with sodium chloride or mannitol solutions with varying osmolality.

2. Administration Regimes

In general the timing and frequency of administration will be adjusted to balance the efficacy of a given treatment or diagnostic schedule with the side-effects of the given delivery system. Exemplary dosing frequencies include continuous infusion, single and multiple administrations such as hourly, daily, weekly, monthly or yearly dosing.

Regardless of systemic, intrathecal, or local delivery into the brain parenchyma itself, penetration of bioactive or imaging agents in the brain and other tissues has been a key hurdle to effective therapy and diagnostics. Numerous studies using viral, nanoparticle, and convection-enhanced delivery have failed due to limited movement of substances within the brain. Therefore, defining the critical limiting parameters and designing strategies to enhance brain penetration will likely improve the efficacy of these treatments. Densely-pegylated nanoparticles offer numerous additional advantages, including increased particle diffusion, improved stability, and prolonged sustained-release kinetics. These factors are known to correlate with the efficacy of many therapeutics and will likely have a significant impact on the utility of nano-sized carriers for diagnostic and therapeutic delivery to the brain.

3. Additional Active Agents

Nanoparticle gene carriers can carry only "genetic" materials. Others can be co-delivered depending on the application. However, any "genetic" materials that can perform the listed functions can be packaged in the nanoparticles. For example, tumor suppressor genes such as p53 and Rb can be complexed into nanoparticles to be used for lung cancer patients, so as any plasmid DNA or siRNA that possess anti-inflammatory, anti-viral functions, etc.

Nanoparticle gene carriers can optionally contain one or more additional, non-nucleic acid active agents. The one or more additional active agents can be dispersed in the nanoparticle gene carriers or be covalently attached to one or more of the polymeric components of the nanoparticle Nanoparticles may also be used for the delivery of chemotherapeutic agents, and anti-proliferative agents. Suitable additional active agents include, but are not limited to, other nucleic acid-based medicine, mucus degrading agents, bronchodilators, anti-inflammatory drugs, antiproliferatives, chemotherapeutics, vasodilators, and anti-infective agents.

Nanoparticle gene carriers can optionally contain one or more mucus degrading agents. Suitable mucus degrading agents include N-acetylcysteine (NAC), mugwort, bromelain, papain, clerodendrum, acetylcysteine, bromhexine, carbocisteine, eprazinone, mesna, ambroxol, sobrerol, domiodol, letosteine, stepronin, tiopronin, gelsolin, thymosin β4, neltenexine, erdosteine, denufosol, and various DNases including rhDNase (such as Dornase Alfa, sold under the tradename PULMOZYME® by Genentech), although care should be taken to deliver DNase separate from DNA.

Nanoparticle gene carriers can optionally contain one or more anti-infective agents. In certain embodiments, the nanoparticle gene carriers contain one or more antibiotics, such as tobramycin, colistin, or aztreonam.

Nanoparticle gene carriers can optionally contain one or more inhaled corticosteroids, such as flunisolide, triamcinolone acetonide, beclomethasone dipropionate, mometasone, budesonide, ciclesonide, or fluticasone propionate.

Nanoparticle gene carriers can optionally contain one or more antibiotics which are known to possess anti-inflammatory activity, such as erythromycin, azithromycin, or clarithromycin.

EXAMPLES

Example 1: Densely PEGylated Vectors Formulated from PEG-PBAE have a Near Neutral Surface Charge and a Drastically Improved Stability Profile Materials and Methods Polymer Synthesis The base poly(β-amino ester) (PBAE) polymers with varying molecular weights were synthesized by reacting 1,4-butanediol diacrylate and 4-amino-1-butanol at the molar ratios of 1.2:1 (PBAE low, MW~4 kDa), 1.1:1 (PBAE mid, MW~7 kDa) and 1.05:1 (PBAE high, MW~11 kDa) while stirring at 90° C. for 24 hours. Polymers were then precipitated and washed in cold ether and dried under vacuum. The molecular weights of the three PBAE base polymers were estimated by gel permeation chromatography and nuclear magnetic resonance spectroscopy. For the capping of end diacrylate groups, each base PBAE polymer was dissolved in tetrahydrofuran (THF) at 100 mg/ml, 30 molar excess of 2-(3-aminopropylamino ethanol) was added, and reaction was undertaken while stirring at room temperature for 2-3 hours. The end capped PBAE polymers with three different molecular weights were retrieved by crashing out polymers in cold ether. Polyethylene glycol (PEG)-conjugated PBAE (PBAE-PEG) polymer was synthesized by a two-step reaction from the uncapped base PBAElow polymers. First, end diacrylate group capping and purification was conducted using the same method above, but with 1,3-diaminopropane instead of 2-(3-aminopropylamino ethanol). Subsequently, the end capped PBAE-low polymers and 2.05 molar excess of 5 kDa methoxy-PEG-N-hydroxysuccinimide transferred to a glass virtual, vacuumed and purges with nitrogen. The mixture of reactants were dissolved in anhydrous THF and reacted while stirring at room temperature overnight. The final PBAE-PEG polymers were precipitated and washed with cold ether and dried. PEG conjugation was confirmed with NMR. Polymers were dissolved in Dimethyl sulfoxide anhydrase (DMSO) at 100 mg/ml for further use.

Gene Vector Complexation

The pBAL and pBACH plasmid was produced by Copernicus Therapeutics Inc. (Cleveland, Ohio) and pEGFP plasmid was purchased by Clontech Laboratories Inc. (Mountainview, Calif.). Mirus Label IT® Tracker™ Intracellular Nucleic Acid Localization Kit (Mirus Bio, Madison, Wis.) was used to fluorescently tag plasmid DNA with a Cy3 or Cy5 fluorophore. PEG-PBAE gene vectors were formed by the drop-wise addition of 5 volumes of labeled or non-labeled plasmid DNA (0.1 mg/ml) to 1 volume of a swirling polymer solution; both solutions had been pre-adjusted to pH 6.5-7.0 using a 0.1M hydrochloride solution (HCL). The optimal PBAE to DNA weight ratio was determined to be 60 and a mixture of PBAE to PBAE-PEG at a molar ratio of 0.67 was used. Depending on the molecular weight of the core non-PEGylated PBAE polymer component (PBAElow, PBAEmid and PBAEhigh) this process resulted in three nanoparticles PEG-PBAElow, PEG-PBAEmid and PEG-PBAEhigh, respectively. In addition, conventional polyethylenimine (PEI) (Suk, et al., *J Control Release*, 2014), PEG-poly-L-lysine (PEG-PLL) (Suk, J. S., et al., *J Control Release*, 2014; Kim, et al., *J Control Release*, 2012. 158(1): 102-7) and PBAE (Akinc, et al., *Bioconjug Chem*, 2003. 14(5): 979-88; Green, et al., *Bioconjug Chem*, 2006. 17(5): 1162-9; Zugates, et al., *Bioconjug Chem*, 2007. 18(6): 1887-96; Tzeng, et al., *Biomaterials*, 2011. 32(23): 5402-10; Anderson, et al., *Angew Chem Int Ed Engl*, 2003. 42(27): 3153-8) gene vectors used for comparison purposes where formulated as previously described.

Gene vectors were washed with 3 volumes of ultrapure distilled water, and re-concentrated to 0.5-1 mg/ml using AMICON® Ultra Centrifugal Filters (100,000 MWCO, Millipore Corp., Billerica, Mass.) to remove free polymers. For PBAE based gene vectors DNA concentration was determined by one of the following methods. For gene vectors containing fluorescently labeled DNA the concentration was calculated based on fluorescence intensity using the Synergy Mx Multi-Mode Microplate Reader (Biotek, Instruments Inc.). For non-fluorescently tagged gene vectors the concentration was measured using the Quant-iT™ PicoGreen® dsDNA Assay Kit (Life Technologies, NY).

Physicochemical Characterization of Nanoparticles

Hydrodynamic diameter and polydispersity (PDI) were measured in ultra-pure water and ζ-potential in 10 mM NaCl at pH 7.0 by dynamic light scattering (DLS) and laser Doppler anemometry, respectively, using a Nanosizer ZS90 (Malvern Instruments, Southborough, Mass.). PBAE and PEG-PBAE gene vector stability was assessed by incubating the nanoparticles in ultra-pure water at room temperature, artificial cerebrospinal fluid (aCSF; Harvard Apparatus, Holliston, Mass.) at 37° C., bronchoalveolar laveage fluid (BALF) at 37° C. To assess their stability in ultrapure water gene vector hydrodynamic diameter was measured for 40 hours every 15 min and following that every 24 hours or until polydispersity (PDI)>0.5. For aCSF and BALF stability DLS was performed every half hour for 15 and 25 hours, respectively; or until PDI>0.5.

Results

Gene Vector Characterization

Using a mixture of Polyethylene glycol/poly (β-amino ester) (PEG-PBAE) copolymer and poly (β-amino ester) (PBAE), highly compact 50 nm gene vectors were formulated with a near neutral surface charge.

By blending non-PEGylated PBAE core polymers of different molecular weights (4 kDa, PBAE-low; 7 kDa, PBAE-mid; 11 kDa, PBAE-high) with PEGylated PBAElow, three gene vectors were formulated: PEG-PBAE (low), PEG-PBAE(mid), and PEG-PBAE(high), respectively, with similar physicochemical characteristics (Table 1).

For the following studies PEG-PBAEmid vectors were used unless otherwise specified. This formulation was compared to conventional non-PEGylated PBAE gene vectors which, as previously reported, formed gene vectors with a diameter over 100 nm, high polydispersity and positive surface charge. The a slight adjustment on the formulation methods, namely the drop wise addition of the DNA solution to the polymer solution at a rate of approximately 1 ml/min, resulted in better compacted sub-100 nm non-PEGylated gene vectors with highly positive surface charge that was used for the following studies. Lyophilization of these nanoparticles using 2% sucrose as a cryopreservant, and storage for 24 hours at room temperature, drastically increased the size and polydispersity of PBAE gene vectors, while only minor changes were observed with the PEG-PBAE gene vectors (Tables 2 and 3). Also, drastic changes were noted with the PBAE (PBAE-CP) gene vectors when stored in artificial CSF (aCSF), while the PEG-PBAE (PBAE-BPN) vectors showed only minor changes with the same treatment (Table 4).

TABLE 1

Physicochemical properties of PEG-PBAE based gene vectors.

| | Hydrodynamic Diameter ± SEM (nm) | ζ-potential ± SEM (mV) | PDI |
|---|---|---|---|
| PEG-PBAE$_{low}$ | 55 ± 2.54 | 0.4 ± 3.2 | 0.18 |
| PEG-PBAE$_{mid}$ | 50 ± 2.79 | 2.5 ± 5.77 | 0.15 |
| PEG-PBAE$_{high}$ | 51 ± 0.97 | 2.1 ± 6.24 | 0.15 |

Size, ζ-potential and polydispersity (PDI) were measured by dynamic light scattering (DLS) in 10 mM NaCl at pH 7.0 and are presented as average of at least 3 measurements±standard error (SEM).

TABLE 2

Physicochemical properties and diffusivity of PEG-PBAE and PBAE based gene vectors.

| | Hydrodynamic Diameter ± SEM (nm) | ζ-potential ± SEM (mV) | PDI |
|---|---|---|---|
| PBAE | 116 ± 11.3 | 16.6 ± 4.5 | 0.5 |
| PBAE (drop wise DNA addition) | 83 ± 0.2 | 21.2 ± 1.6 | 0.1 |
| PEG-PBAE | 50 ± 2.7 | 2.5 ± 5.8 | 0.15 |
| PBAE (post lyophilzation) | 178 ± 9.4 | 0.6 ± 0.6 | 0.4 |
| PEG-PBAE (post lyophilization) | 73 ± 2.3 | 2 ± 0.1 | 0.23 |

Size, ζ-potential and polydispersity (PDI) were measured by dynamic light scattering (DLS) in 10 mM NaCl at pH 7.0 and are presented as average of at least 3 measurements±standard error (SEM). PBAEmid polymer was used for the formulation of these nanoparticles.

PBAE-based gene vectors for gene delivery to the lung and brain were generated. Conventional particles (CP, PBAE-CP), were formulated by compacting plasmid DNA with non-PEGylated PBAE only. These particles displayed a particle hydrodynamic diameter of ~85 nm and a positive surface charge (ζ-potential ~30 mV) (Table 3). A blend of PBAE and PEGylated PBAE at an optimized ratio based on PBAE mass (w/w ratio of 2:3 PBAE:PBAE-PEG) compacted plasmid DNA more tightly (~50 nm in diameter) and provided near neutral surface charge (~2 mV), indicating that the particle surface was densely shielded with PEG chains. These particles are referred to as PBAE-mucus penetrating particles, or PBAE-MPP, when used for lung mucus penetration. When used in studies for brain tissue penetration, these particles are named PBAE-brain penetrating nanoparticles, or PBAE-BPN. The physicochemical properties of PBAE-BPN in artificial CSF (aCSF) is presented in Table 4.

Conventionally PEGylated PLL/DNA (PLL-CP; a replicate of the CK30PEG10k DNA-NP (Konstan et al., *Hum. Gen. Ther.* 15(12):1255-1269 (2004)) and non-PEGylated PEI/DNA (PEI-CP, Neuberg et al., *Adv. Genet.* 88:263-288 (2014) were also generated. The physicochemical properties of PEI-CP and PLL-CP are presented in Table 6.

TABLE 3

Physicochemical properties of PEG-PBAE (PBAE-MPP) and PBAE (PBAE-CP) based gene vectors compared fresh, after 24 hour storage at room temperature, and lyophilized.

| | Storage[a] | Hydrodynamic Diameter ± SEM (nm)[b] | PDI[b] | ζ-potential ± SEM (mV)[c] |
|---|---|---|---|---|
| PBAE-CP | Fresh | 84 ± 2.8 | 0.1 | 31.0 ± 1.3 |
| | 24 h at RT | 262 ± 3.6 | 0.2 | 0.7 ± 1.2 |
| | Lyophilized | 178 ± 9.4 | 0.4 | 0.6 ± 0.6 |
| PBAE-MPP | Fresh | 50 ± 1.1 | 0.1 | 0.5 ± 0.2 |
| | 24 h at RT | 54 ± 1.9 | 0.1 | 1.6 ± 0.1 |
| | Lyophilized | 73 ± 2.3 | 0.2 | 2 ± 0.1 |

[a]PBAE-based DNA-NP were characterized directly after the formulation, following 24 h storage at room temperature (RT) or following lyophilization and subsequent rehydration.
[b]Hydrodynamic diameter and PDI were measured by dynamic light scattering (DLS) in water (pH 7.0). Data represents mean ± SEM (n ≥ 3).
[c]ζ-potential was measured by laser Doppler anemometry in 10 mM NaCl (pH 7.0). Data represents mean ± SEM (n ≥ 3).

TABLE 4

Physicochemical properties of PEG-PBAE (PEG-BPN) in artificial CSF (aCSF).

| | Hydrodynamic Diameter ± SEM (nm)[a] | | ζ-potential ± SEM (mV)[b] | PDI[a] |
|---|---|---|---|---|
| | Number mean | Z-average | | |
| PBAE-CP | 108 ± 1.5 | 150 ± 1 | 35.3 ± 1.6 | 0.1 |
| PBAE-BPN | 53 ± 1.5 | 82 ± 0.1 | 2.0 ± 0.3 | 0.1 |
| PBAE-CP in aCSF[c] | 310 ± 35 | 1340 ± 486 | 14.5 ± 2.4 | 0.8 |
| PBAE-BPN in aCSF[c] | 53 ± 1.2 | 95 ± 2.1 | -1.3 ± 1.0 | 0.2 |

[a]Size and polydispersity index (PDI) were measured by dynamic light scattering (DLS) in ultra pure water and are presented as an average of at least 3 measurements ± standard error (SEM).
[b]ζ-potential was measured by laser Doppler anemometry in 10 mM NaCl at pH 7.0 and is presented as an average of at least 3 measurements ± standard error (SEM).
[c]NP were incubated in aCSF at 37° C. for 5 min prior to size, ζ-potential and PDI measurements.

Following incubation of PBAE and PEG-PBAE gene vectors in ultra-pure water in room temperature, PEG-PBAE demonstrated high stability over 1 week while PBAE started increasing in size after 20 hours and reached PDI>0.5 after 30 hours indicating aggregation and lack of colloidal stability (FIG. 1A). This is important even without the use of storage techniques such as lyophilization.

Figure 1C:
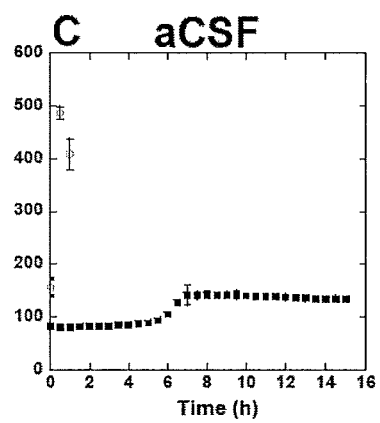

To predict the particle stability of gene vectors following in vivo administration, their in vitro stability in BALF and aCSF was characterized at 37° C. over time. PBAE immediately aggregated after their addition in these physiological solutions of high ionic strength. The gene vectors reached PDI>0.5 at 1 hour incubation in aCSF or BALF, indicating rapid loss of colloidal stability. PEG-PBAE retained their colloidal stability in BALF with a sub-100 nm hydrodynamic diameter over 20 hours of incubation. The hydrodynamic diameter of PEG-PBAE increased to 80 nm following addition to aCSF and remained stable over 6 hours. After 6 hours the gene vectors doubled in size and retained their colloidal stability for up to 15 hours (FIGS. 1B and 1C). Thus, the dense PEGylation and blended formulation of PEG-PBAE allows for a drastically improved stability profile.

Example 2: PEG-PBAE Nanoparticles Provide Effective Gene Transfer to the Lung Cells In Vitro and In Vivo Materials and Methods Cell Culture Human bronchial epithelial (BEAS-2B) cells (ATCC, Manassas, Va.) were cultured in DMEM/F12 (Invitrogen Corp., Carlsbad, Calif.) supplemented with 10% FBS and 1% pen/strep. When cells were 70-80% confluent on passage one, they were immediately re-seeded in 24-well plates to assess transfection. U87 human gioblastoma cells were provided by Dr. Henry Brem and were cultured in Dulbecco's modified Eagle's medium (DMEM, Invitrogen Corp., Carlsbad, Calif.) supplemented with 1% penicillin/streptomycin (pen/strep, Invitrogen Corp., Carlsbad, Calif.) and 10% heat inactivated fetal bovine serum (FBS, Invitrogen Corp., Carlsbad, Calif.). When cells were 70-80% confluent, they were reseeded 24-well plates to assess transfection and cell uptake of gene vectors.

In Vitro Transfection

To assess in vitro transfection cells were seeded at an initial density of $5.0 \times 10^4$ cells/well. After 24 h, cells were incubated with pBAL plasmid in gene vector form (1 µg DNA/well) in media for 5 h at 37° C. Cationic polymer-based gene vector transfection was compared to free plasmid control. Subsequently, nanoparticles and culture media were replaced with fresh media. After additional 5 days of incubation at 37° C., media was removed and 0.5 ml of 1× Reporter Lysis Buffer was added. Cells were subjected to three freeze-and-thaw cycles to assure complete cell lysis, and supernatants were obtained by centrifugation. Luciferase activity in the supernatant was then measured using a standard luciferase assay kit (Promega, Madison, Wis.) and a 20/20n luminometer (Turner Biosystems, Sunnyvale, Calif.). The relative light unit (RLU) was normalized to the total protein concentration of each well measured by the Pierce™ BCA Protein Assay Kit.

Assay for Cell Uptake

To assess cell uptake, cells were seeded at an initial density of $5.0 \times 10^4$ cells/well. After 24 h, cells were incubated with Cy3 labeled plasmid in gene vector form (1 µg DNA/well) in media. After 5 hours the media was removed and cells were thoroughly washed 3 times with 1×PBS and incubated with 1 volume of 0.25% Trypsin with EDTA for 5 min at 37° C. Three volumes of DMEM medium with 10% FBS were added to neutralize trypsin. Nanoparticle cell uptake was measured using the Accuri C6 flow cytometer (BD Biosciences, USA) with an FL2 ban-pass filter with emission detection wavelength of 585/40 nm. Data were analyzed using the BD Accuri C6 software. Thresholds were determined using untreated samples and gene vector cell uptake was compared to free plasmid.

Multiple Particle Tracking

Multiple particle tracking (MPT) was used to quantify the MSD of fluorescently labeled particles in freshly expectorated cystic fibrosis (CF) mucus, as previously described (Suk et al., *J. Control Release*, 178:8-17 (2014)). The mucus samples were immediately placed on ice upon collection and studied on the same day. A total of 11 individual samples were used for this study. A 1 µl solution of fluorescently labeled particles at a plasmid DNA concentration of 10 µg/ml was added to 30 µl of CF mucus, placed in custom made microwells and equilibrated for 30 min at room temperature. Movies were recorded over 20 s at an exposure time of 66.7 ms by an Evolve 512 EMCCD camera (Photometrics, Tucson, Ariz.) mounted on an inverted epifluorescence microscope (Axio Observer D1; Carl Zeiss, Hertfordshire, UK) equipped with a 100×/1.46 NA oil-immersion objective. Movies were then analyzed using a custom made MATLAB code to simultaneously extract x, y-coordinates of the hundreds of particles centroids and calculate individual and ensemble-averaged mean square displacement as a function of timescale. To minimize the effect of dynamic error in our measurement, we calculated the MSD at 1 s. The theoretical diffusion rates of DNA-NP in water were calculated using the Stokes-Einstein equation.

In Vivo Gene Vector Distribution and Airway Gene Transfer

To study gene vector distribution in the large and small airways, a 50 µl solution of gene vectors carrying Cy3 labeled plasmid at a 0.5 mg/ml concentration was administered intratracheally using a microsprayer (Penn Century-Micro Sprayer, Model IA-1C, Philadelphia, Pa., USA) to anesthetized Balb/c mice (female, 6-8). PEG-PBAEmid gene vectors were used and compared to PEI and PEG-PLL gene vectors. Animals were sacrificed after 30 min, lungs flash frozen in OCT, cryosectioned (Leica CM 1905 cryostat), stained with DAPI (Molecular Probes, Eugene, Oreg.) and imaged using confocal LSM 710 microscope under 20× magnification (Carl Zeiss; Hertfordshire, UK). Non treated mice were used to determine settings with no background fluorescence.

To assess in vivo transgene expression a 50 µl solution of gene vectors carrying pBAL luciferase expressing plasmid at a 0.5 mg/ml concentration was administered intratracheally using a microsprayer (Penn Century-Micro Sprayer, Model IA-1C, Philadelphia, Pa., USA) or intranasally to anesthetized Balb/c mice (female, 6-8). For the first experiment, PEG-PBAE nanoparticles with a core non-PEG PBAE polymer component of varying molecular weights (PEG-PBAElow, PEG-PBAEmid and PEG-PBAEhigh) were administered intratracheally and compared to conventional PEI and PEG-PLL gene vectors.

Non-treated mice were used to measure background luminescence and free plasmid was administered as a control. Animals were sacrificed after 1 week and luciferase activity on lung tissue homogenates was measured using a standard luciferase assay kit (Promega, Madison, Wis.) and a 20/20n luminometer (Turner Biosystems, Sunnyvale, Calif.). For the following experiments PEG-PBAEmid (henceforth PEG-PBAE) was used. EG-PBAE and PEI gene vector transfection efficacy was compared following intratracheal or intranasal administration.

To assess the transfection efficacy following repeated dosing a multi-dose study was performed. Mice were intratracheally dosed once or twice with PEG-PBAE (25 µg plasmid per mouse) carrying pBACH plasmid (mCherry) followed by administration of pBAL plasmid DNA (luciferase). These two plasmids are identical except for the reporter coding sequences. The dosing interval chosen was 2 weeks and animals were sacrificed 1 week following pBAL administration. The transfection efficacy of PEG-PBAE was also studied following storage in an aqueous solution and following lyophilization using 2% sucrose for cryopreservation. To assess long term transgene expression, luciferase expressing PEG-PBAE gene vectors were administered and mice were sacrificed at different time points.

Statistical Analysis

Statistically significant differences between two groups were analyzed with a two-tailed Student's t test assuming unequal variances or paired student's t test when allowed. Multiple comparisons were performed using one-way analysis of variance (ANOVA) followed by post hoc test using SPSS 18.0 software (SPSS Inc. Chicago, Ill.).

Results

Gene Delivery In Vitro

Figure 2A:
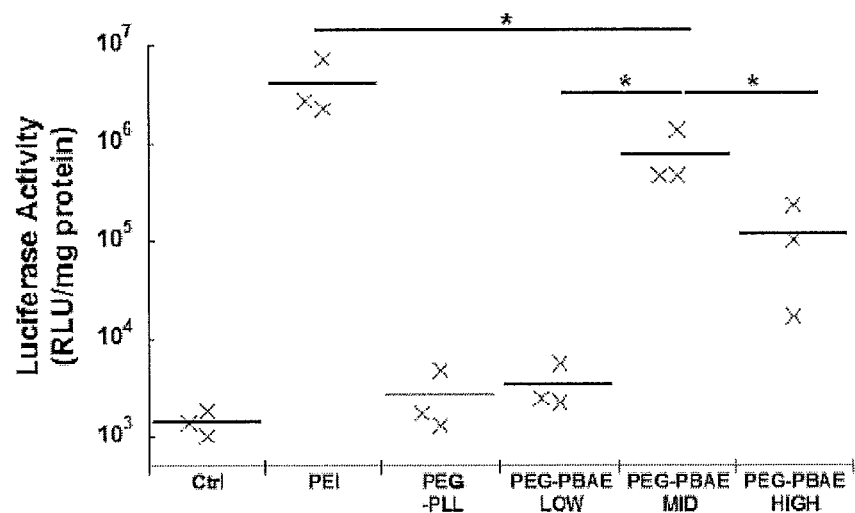
FIG. 2A is a graph showing luciferase activity (RLU/mg protein) of bronchial airway epithelial cells transfected with vectors Ctrl, PEI, PEG-PLL, PEG-PBAE (MID) and PEG-PBAE (HIGH), respectively. * Denotes statistically significant (p<0.05) difference.

The transfection efficacy of these gene vectors was compared to conventionally used polyethylenimine (PEI) and PEG-poly-L-lysine (PEG-PLL) gene vectors (developed by Copernicus, Inc.) in bronchial epithelial cells. Despite their dense PEG coating, PEG-PBAE(mid) and PEG-PBAE (high) demonstrated high transfection efficacy, while PEG-PBAElow resulted in significantly lower transfection (FIG. 2A). All PEG-PBAE formulations had significantly lower in vitro transfection than PEI gene vectors. This may be attributed to their dense PEG surface coating reducing cell uptake and endosome escape.

Figure 2B:
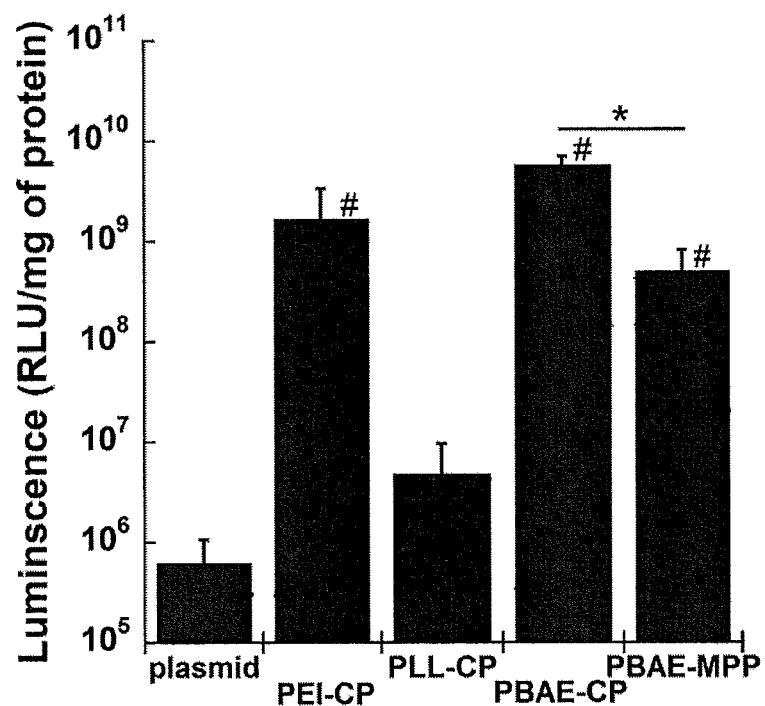
FIG. 2B is a bar graph showing luciferase activity (luminescence (RLU/mg of protein)) following in vitro transfection of human bronchial airway epithelial cells (BEAS-2B) using various particles carrying pBAL. * Denotes statistically significant difference (p<0.05). # Denotes statistically significant differences (p<0.05) compared to PLL-CP and a plasmid DNA control.

The in vitro transfection efficiency of PBAE-MPP in BEAS-2B human bronchial epithelial cells to that achieved by PBAE-CP, PEI-CP and PLL-CP were compared (FIG. 2B). PBAE-CP exhibited the highest transfection efficiency, presumably attributed to the biodegradable nature of PBAE that facilitates intracellular release of the packaged plasmid DNA. In accordance with previous reports that PEGylation may reduce in vitro transfection, PBAE-MPP exhibited significantly lower in vitro transfection efficiency compared to uncoated PBAE-CP. However, PBAE-MPP transfected BEAS-2B cells as efficiently as non-PEGylated PEI-CP, and significantly greater than PLL-CP. This ability of PBAE-MPP to retain high in vitro transfection efficiency and colloidal stability in physiological conditions could enhance its overall gene transfer efficacy in vivo.

Gene Delivery to the Lung

Figure 3D:
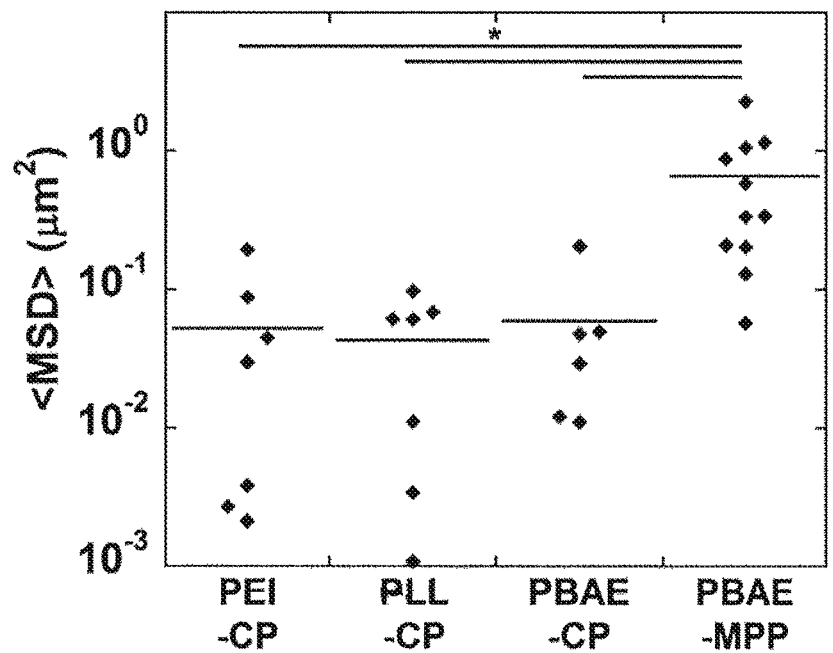
FIG. 3D is a dot-plot showing the ensemble-averaged geometric means of MSD (<MSD>, $\mu m^2$) of PEG-PBAE (PBAE-MPP) particles and conventional particles (CP) of PEI (PEI-CP), PEG-PLL (PLL-CP), and PBAE (PBAE-CP) at a timescale of 1 s in individual mucus samples. *Denotes statistically significant difference (p<0.05).

The diffusion of PEG-PBAE in comparison to PEI and PEG-PLL was investigated in freshly expectorated sputum from cystic fibrosis patients, using multiple particle tracking (MPT). MPT allows for simultaneous tracking of hundreds of nano-objects in various biological environments, providing quantitative assessments of their diffusion rates as represented by mean square displacement (MSD); MSD is a square of distance traveled by nano-objects during a given time interval. As previously demonstrated, PEI and PEG-PLL were strongly hindered with constrained non-Brownian time-lapse traces. In contrast, PEG-PBAE trajectories spanned over greater distances indicating unhindered diffusion in CF sputum (FIG. 3A). Based on the trajectories, the ensemble averaged MSD (<MSD>) over a time scale of 1 second was calculated; PEG-PBAE presented significantly higher MSD at 1 second in comparison to PEI and PEG-PLL (FIG. 3B). The distribution of logarithmic MSD (log 10 MSD) of hundreds of individual gene vectors was also investigated (FIG. 3C). Defining rapidly moving gene vectors by log 10 MSD≥−1, at least half of PEG-PBAE gene vectors were able to efficiently penetrate CF sputum, whereas only 12.2% of PEI and 18.2% of PEG-PLL could do so. Also, PBAE-MPP diffused significantly faster ($p<0.05$) than the conventional DNA-NP (FIG. 3D)

Figure 3E:
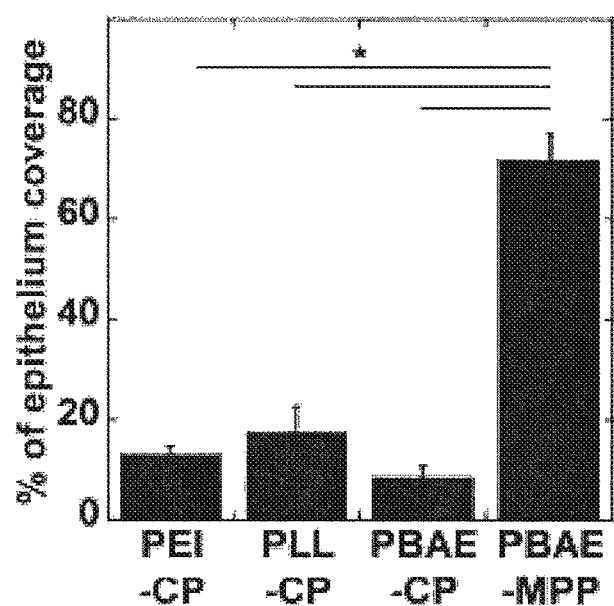
FIGS. 3E to 3H are bar graphs showing in vivo distribution of gene vector particles PEG-PBAE (PBAE-MPP) when compared to conventional particles (CP) of PEI (PEI-CP), PEG-PLL (PLL-CP), and PBAE (PBAE-CP) following intratracheal administration.
Figure 3F:
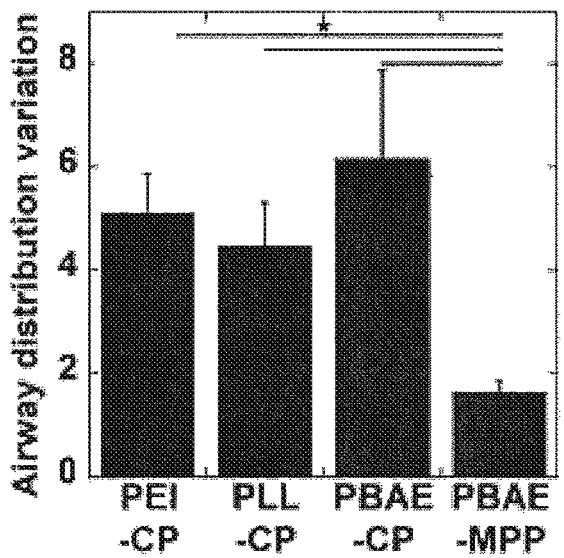
Figure 3G:
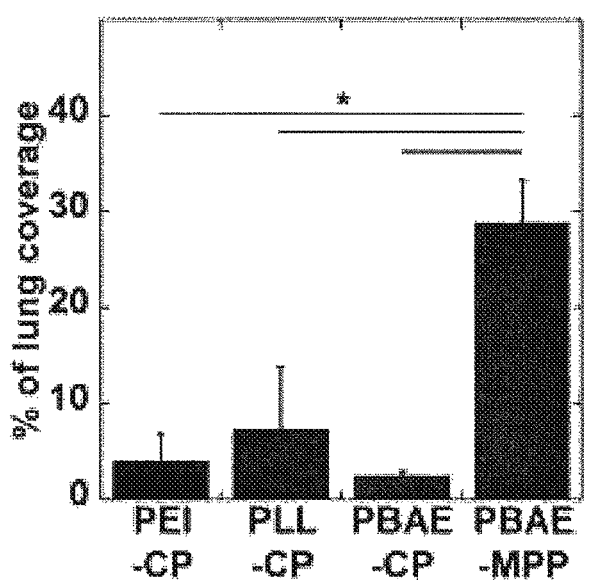
Figure 3H:
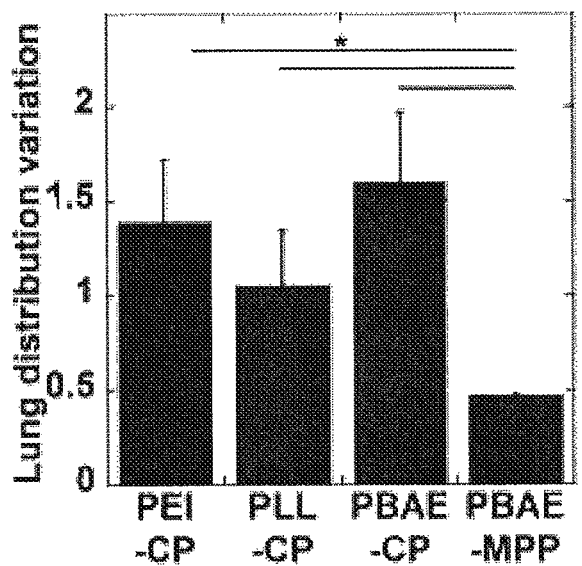

In accordance with the ex vivo particle tracking results, PEG-PBAE homogeneously distributed in the large airways and effectively reached the alveoli covering the entire lung parenchyma, following intratracheal administration to the mouse lungs. Mice dosed identically with PEI or PEG-PLL demonstrated sparse areas of highly accumulated gene vectors in the large airways, suggesting aggregation and entrapment of gene vectors in the luminal mucus gel layer covering the airway epithelium. In addition, a very limited amount of these gene vectors reached the lung parenchyma (FIGS. 3E-3H) PEG-PBAE (also referred to herein as PBAE-MPP, PBAE-mucus penetrating particles) exhibited widespread distribution throughout the lung airways, whereas other conventional DNA gene vectors (PBAE-CP, PEI-CP and PLL-CP) were all sparsely distributed. The airway coverage of PBAE-MPP was approximately 70%, with minimal variation in airway distribution (i.e. highly uniform distribution), in sharp contrast to 20% coverage at best with large variations observed for all other DNA-NP (FIGS. 3E and 3F). Similar results were observed in the lung parenchyma (FIGS. 3G and 3H), likely due to the dense surface PEG coatings that reduce particle aggregation and phagocytosis by alveolar macrophages.

Figures 4A, 4B:
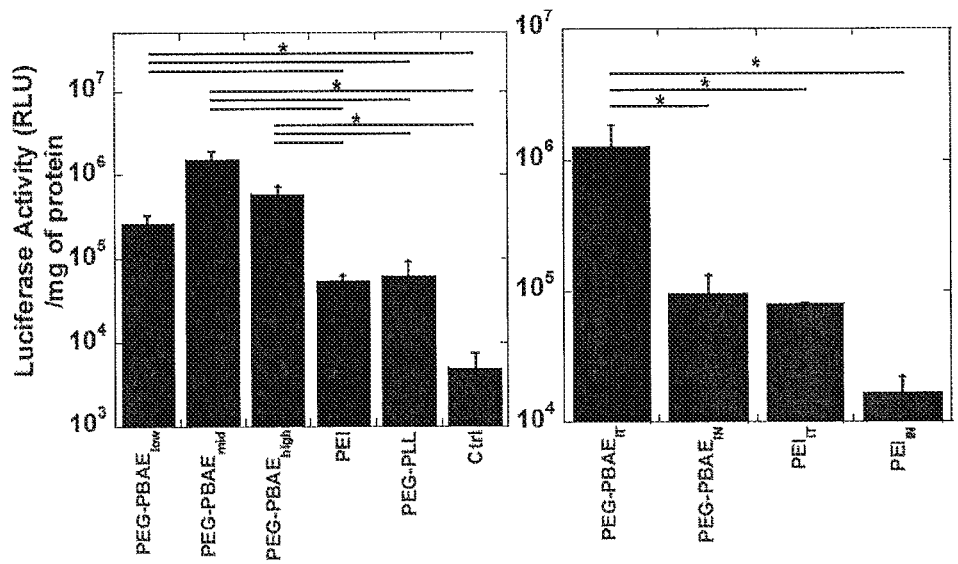
FIGS. 4A and 4B are histograms showing the luciferase activity (RLU)/mg of protein for each of the PEG-PBAE (LOW), PEG-PBAE (MID) and PEG-PBAE (HIGH) PEI, PEG-PLL and control (Ctrl) (FIG. 4A), PEG-PBAE$_{IT}$, PEG-PBAE$_{IN}$, PEI$_{IT}$ and PEI$_{IN}$ (FIG. 4B) gene vectors, respectively. Data represents the mean±SEM. * Denotes statistical significance P<0.05.

Following administration of gene vectors carrying a luciferase expressing plasmid driven by a β-actin promoter (pBAL), the level of transgene expression mediated by different vector types was compared. PEG-PBAE gene vectors with both high and low molecular weights resulted in significantly higher transfection in comparison to PEI and PEG-PLL (FIG. 4A). In fact, PEG-PBAEmid resulted in 25 and 28-fold higher transfection than PEI and PEG-PLL respectively. Moreover, the intranasal administration of PEG-PBAE (PEG-PBAE$_{IN}$), despite a large fraction being retained in nostril or delivered to gastrointestinal tract, resulted in transgene expression comparable to that achieved by intratracheal administration of PEI (PEI$_{IT}$) (FIG. 4B) where the gene vectors are directly aerosolized in the respiratory tract.

Figures 5A, 5B:
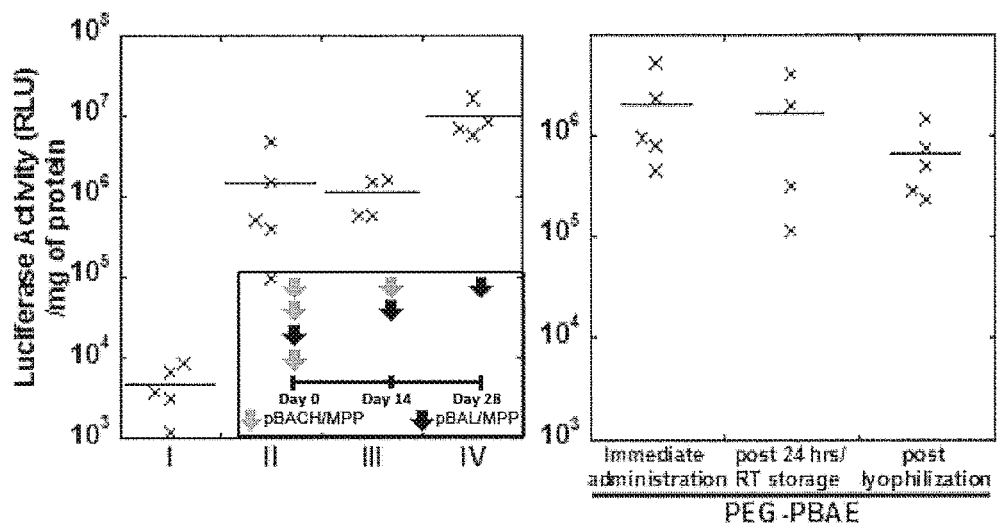
FIG. 5A is a dot blot, showing luciferase activity (RLU)/mg of protein for repeated intratracheal administrations of PEG-PBAE (n=4-5). *Denotes statistically significant difference from Group I (p<0.05). Shown in the inset is treatment with PBAE-MPP carrying pBACH plasmid DNA (grey arrows), or the pBAL plasmid DNA (black arrows); the two plasmids are identical except for different reporter coding sequences.
FIGS. 5B and 5C are graphs showing luciferase activity (RLU)/mg of protein for luciferase expression by PEG-PBAE using different storage methods (FIG. 5B), or different time points following intratracheal administration of PBAE-MPP (FIG. 5C), respectively.
Figure 5C:
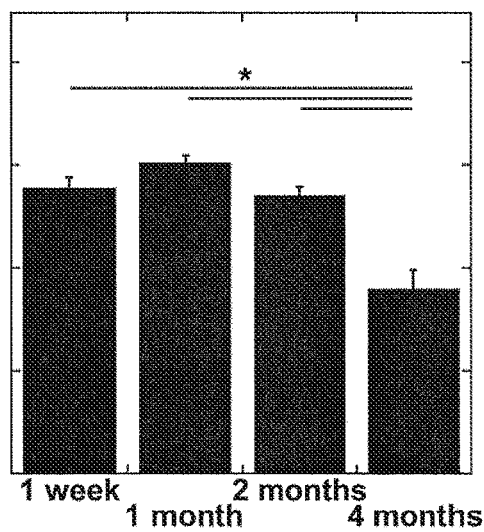

Repeated administrations of PEG-PBAE gene vectors did not decrease transfection efficacy. The dosing regime with the vector was as follows: (n=4-5) mice were dosed once or twice with PBAE-MPP carrying pBACH with a 2 week interval, and 2 weeks after the final pBACH dose, PBAE-MPP carrying pBAL were administered. Luciferase expression was quantified 1 week after the final administration. Groups I and II represent mice treated with a single dose of pBACH (negative control) and pBAL (positive control), respectively. Mice in Groups III and IV were exposed to a single dose or double dose of pBACH, respectively, and subsequently dosed with pBAL. The two plasmids are identical except for the reporter coding sequences (FIG. 5A). A phenomenon observed in viral gene delivery due to the vector-inactivating immune response against viral vectors (FIG. 5A). To assess the effect of different storage methods on in vivo gene transfer, transfection efficiency of freshly made PEG-PBAE gene vectors was compared to PEG-PBAE stored in room temperature for 24 hours and PEG-PBAE lyophilized and subsequently reconstituted. No statistically significant difference in transfection efficiency was observed among three groups (FIG. 5B). Importantly, the high level transfection achieved by PEG-PBAE and the use of a β-actin promoter resulted in long term transgene expression over at least 1 month (FIG. 5C).

Figure 6A:
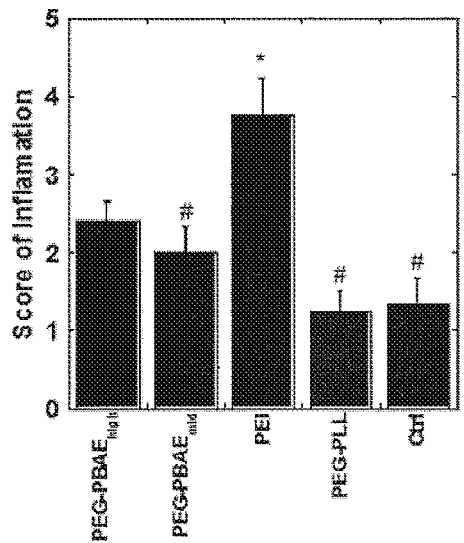
FIGS. 6A and 6B are histograms showing the score of inflammation (FIG. 6A) and total cells ($10^5$/ml of BALF) (FIG. 6B) for each of, PEG-PBAE(HIGH), PEG-PBAE (MID), PEI, PEG-PLL and control (Ctrl), respectively, following intra tracheal administration of cationic polymer based gene vectors. * denotes statistically significant difference from Ctrl (p<0.05) and # denotes significant difference from PEI administered animals (p<0.05).
Figure 6B:
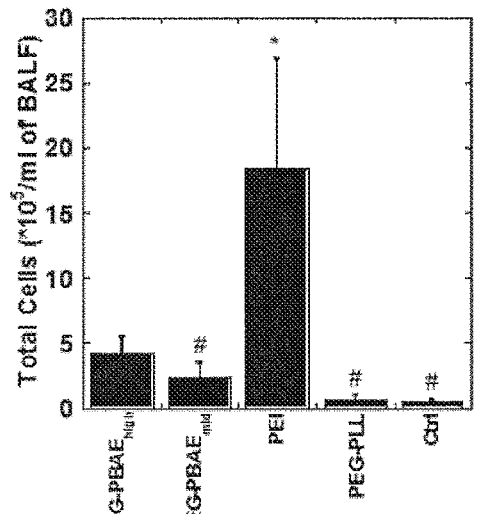

Gene vector toxicity constitutes an important limitation of cationic polymer based nanoparticles. The fact that PBAE are biodegradable and have a relatively low charge density promises a favorable safety profile for gene delivery. Indeed, following intratracheal administration PEG-PBAE demonstrated minimal lung inflammation comparable to that of PEG-PLL and non-treated mice and significantly lower than that of PEI gene vectors which are the gold standard of cationic polymer based gene therapy (FIGS. 6A-6B).

Figure 6C:
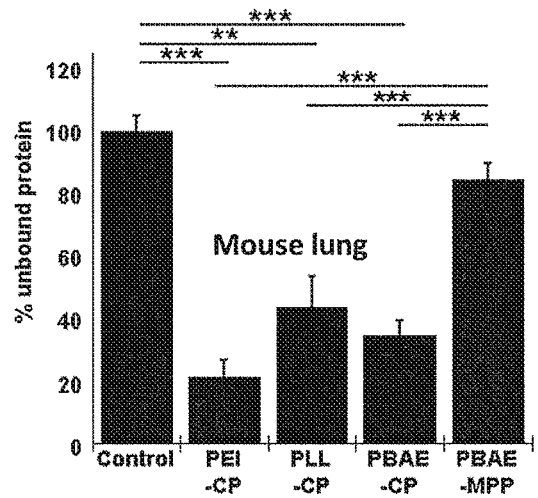
FIGS. 6C and 6D are bar graphs showing adsorption of pulmonary proteins onto PEG-PBAE (PBAE-MPP), PEI (PEI-CP), PEG-PLL (PLL-CP), and PBAE (PBAE-CP), or control particles. Western blot-based quantification of unbound protein levels following incubation of different particles with mouse lung lysate (n=8, FIG. 6C) and human CF mucus lysate (n=4, FIG. 6D) at a protein concentration of 1.3 mg/ml. Differences are statistically significant as indicated (*p<0.05, p<0.01, *p<0.001).
Figure 6D:
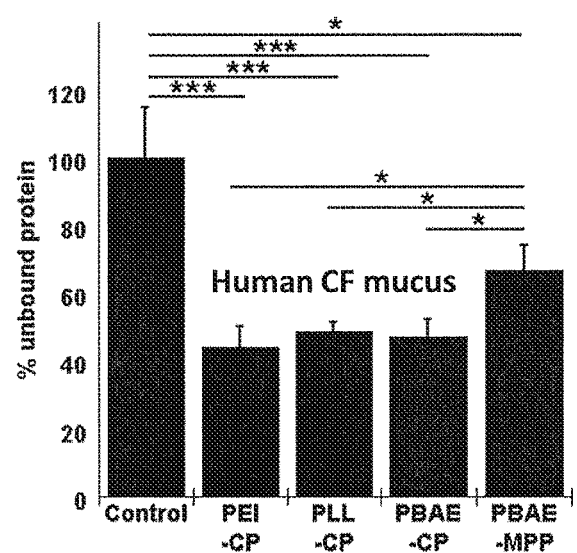

Following the incubation in mouse lung lysates, protein adsorption on the surface of PBAE-MPP was negligible, whereas 79%, 56% and 66% of total proteins were found associated with PEI-CP, PLL-CP and PBAE-CP, respectively (FIG. 6C). Likewise, PBAE-MPP exhibited significantly improved resistance against the adsorption of proteins present in human CF mucus compared to all other particle formulations (FIG. 6D). Of note, the conventional PEG coating of PLL-CP failed to provide an enhanced surface shielding compared to non-PEGylated particles, suggesting that a dense surface coverage of PEG is required to effectively preclude the adsorption of pulmonary macromolecules onto nanoparticles.

Example 3: PEG-PBAE Gene Vectors Provide High Level and Widespread Gene Transfer to the Brain Materials and Methods
Cell Culture Rat brain primary astrocytes were provided by Dr. Arun Venkatesan. Rat brain primary mixed cultures were isolated form neonatal P3-P6 rats and astrocytes were isolated with the conventional shake off method. Cells were cultured in DMEM/F12 (Invitrogen Corp., Carlsbad, Calif.) supplemented with 10% FBS and 1% penicillin/streptomycin. When cells were 70-80% confluent on passage one, they were immediately re-seeded in 24-well plates to assess transfection and cell uptake of gene vectors.
Multiple Particle Tracking Multiple particle tracking (MPT) was used to estimate the mean square displacement (MSD) of fluorescent gene vectors in ex vivo rodent brain slices. Briefly, brain was harvested from healthy and F98 tumor inoculated adult Fisher rats and incubated in aCSF for 10 minutes on ice. Brain was sliced into 1.5 mm coronal slices using a Zivic brain matrix slicer (Zivic Instruments, Pittsburgh, Pa.) and placed on custom made slides. Half a microliter of fluorescently labeled gene vectors was injected on the cerebral cortex or the tumor tissue at a depth of 1 mm using a 50 µl Hamilton Neuro Syringe (Hamilton, Reno, Nev.) mounted on a stereotaxic frame. Tissues were covered by a 22 mm×22 mm coverslip to reduce tissue movement and bulk flow. Particle trajectories were recorded over 20 seconds at an exposure time of 66.7 ms by a Evolve 512 EMCCD camera (Photometrics, Tucson, Ariz.) mounted on an inverted epifluorescence microscope (Axio Observer D1, Zeiss; Thornwood, N.Y.) equipped with a 100×/1.46 NA oil-immersion objective.

Movies were analyzed with a custom made MATLAB code to extract x, y-coordinates of gene vectors centroids over time and calculate the mean square displacement of each particle as a function of time. Similarly, MPT was used to estimate the mean square displacement (MSD) of fluorescent gene vectors in freshly expectorated mucus from cystic fibrosis patients collected at the Johns Hopkins Adult Cystic Fibrosis Program.
In Vivo Brain Distribution Study Following CED Female Fischer 344 rats weighing 120-140 g were anesthetized with a mixture of ketamine-xylazine. A midline scalp incision was made to expose the coronal and sagittal sutures and a burr whole was drilled 3 mm lateral to the saggital suture and 0.5 mm posterior to the bregma. Following the administration of nanoparticle solution the skin was closed using biodegradable sutures (POLYSORB™ Braided Absorbable Sutures 5-0) and BACITRACIN was applied. A 33 gauge 50 µl Hamilton Neuro Syringe mounted to a stereotaxic headframe was lowered to a depth of 3.5 mm and a 20 µl solution of gene vectors was administered. To account for injection variability, two separate experiments were performed. First, Cy3 labeled PBAE or PEG-PBAE gene vectors were individually administered at a plasmid concentration of 1 mg/ml in normal saline. Second, Cy3 labeled PBAE and Cy5 labeled PEG-PBAE were co-injected at a plasmid concentration of 1 mg/ml per particle type in normal saline. The rate of infusion was set at 0.33 µl/min, using a Chemyx Inc. Nanojet Stereotaxic syringe pump (Chemyx, Stafford, Tex.). Animals were sacrificed 2 hours following CED.

Freshly harvested brains were fixed in 4% formaldehyde overnight followed by gradient sucrose solution processing before cryosection. Tissues were sectioned coronally into 100 micrometer thick slices using Leica CM 1905 cryostat. Slices were stained with DAPI (Molecular Probes, Eugene, Oreg.) and imaged for DAPI (cell nuclei), Cy3 and Cy5 or Alexa Fluor 488 (eGFP) using confocal LSM 710 microscope under 5× and 10× magnification (Carl Zeiss; Hertfordshire, UK). Settings were carefully optimized to avoid background fluorescence based on non-injected control rat brains. Laser power, pinhole, gain, offset and digital gain were selected separately for each magnification and kept constant throughout the study.

Figures 7A, 7B, 7C, 7D:
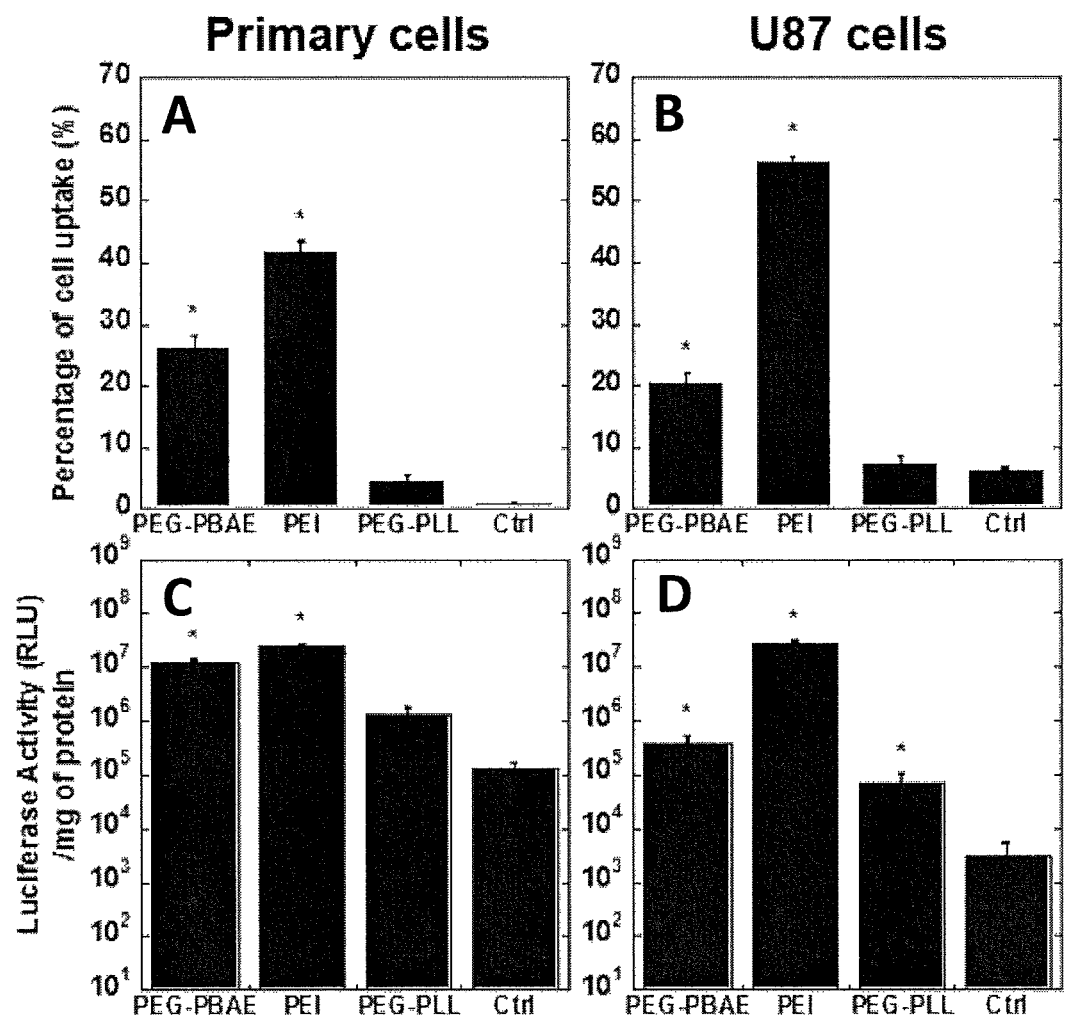
FIGS. 7A and 7B are histograms showing the percentage of cell uptake (%) for each of PEG-PBAE, PEI, PEG-PLL and control (Ctrl) vectors in primary cells (FIG. 7A) and U87 human glioblastoma cells (FIG. 7B), respectively.
FIGS. 7C and 7D are histograms showing luciferase activity (RLU)/mg protein for each of PEG-PBAE, PEI, PEG-PLL and control (Ctrl) vectors in primary cells (FIG. 7C) and U87 human glioblastoms cells (FIG. 7D), respectively. Data represents the mean±SEM. *Denotes statistical significance (P<0.05) difference from free plasmid.
Figure 7E:
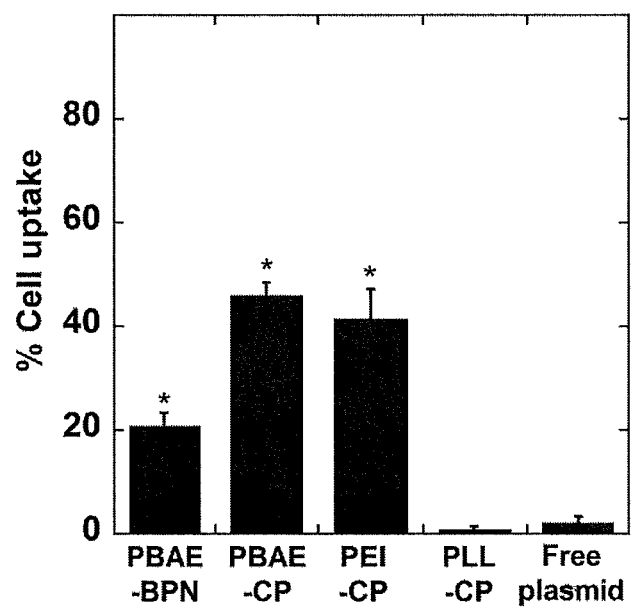
FIG. 7E is a bar graph showing flow cytometric analysis of in vitro gene vector cell uptake (%) in F98 Glioblastoma cells following treatment with fluorescently tagged PEG-PBAE (PBAE-BPN), PEI (PEI-CP), PEG-PLL (PLL-CP), PBAE (PBAE-CP) gene vectors of free plasmid for 5 hours.
Figure 7F:
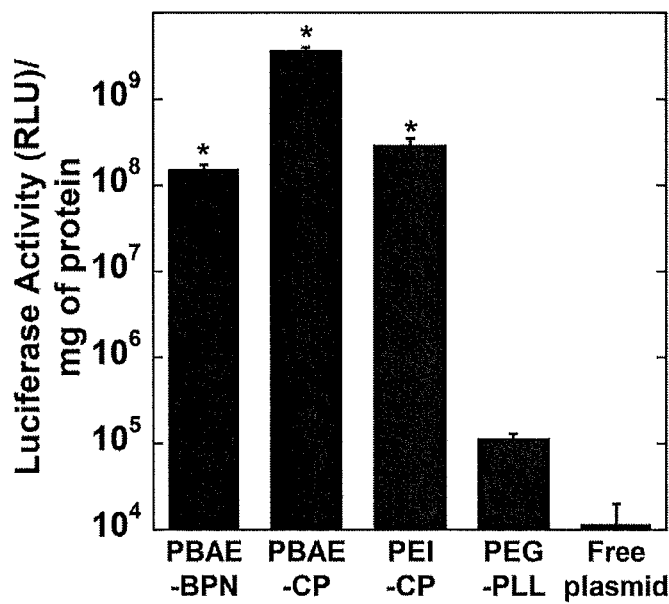
FIG. 7F is a bar graph showing in vitro transfection of luciferase expressing plasmid to F98 Glioblastoma cells by PEG-PBAE (PBAE-BPN), PEI (PEI-CP), PEG-PLL, PBAE (PBAE-CP) gene vectors or free plasmid. Data represents the mean±SEM. * Denotes statistically significant (p<0.05) difference from free plasmid control.

For both experiments the nanoparticle volume of distribution following CED administration was quantified using a custom MATLAB script that subtracted the background fluorescence and thresholded the fluorescent intensities at 10% of the maximum intensity. Nanoparticle fluorescence in the corpus callosum due to backflow was excluded from quantification. Every 100 µm slice within 2 mm of the injection plane was imaged. The area of distribution on each slice was summated to calculate the total volume of nanoparticle distribution.
Results
Gene Delivery to the Brain The cell uptake and transgene expression mediated by PEG-PBAE, in comparison to conventional PEI and PEG-PLL gene vectors, was assessed in primary rodent astrocytes as well as U87 human glioblastoma cells in vitro. PEG-PBAE vectors were taken up by cells 6 and 3-fold more than PEG-PLL, for primary astrocytes and human glioblastoma cells, respectively. However, PEI gene vectors were taken up by cells 1.5 and 2.8 fold more than PEG-PBAE for primary astrocytes and human glioblastoma cells, respectively (FIGS. 7A and 7B). Luciferase expression following PEG-PBAE treatment did not differ significantly from PEI for primary astrocytes while PEG-PBAE transfected U87 cells significantly lower than PEI (FIGS. 7C and 7D). The cellular uptake and in vitro transfection of F98 glioblastoma cells showed that PEG-PBAE was taken up by about 20% of the cells, and the luciferase-expressing plasmid was effectively translated in the cells (FIGS. 7E and 7F).
Diffusion of Nanoparticles in Healthy Rodent Brain Next, the diffusion of PEG-PBAE and PBAE in healthy rodent brain, using MPT was studied. As expected, due to their positive surface charge, the PBAE were strongly hindered in the brain parenchyma with constrained non-Brownian time-lapse traces. In contrast, PEG-PBAE trajectories spanned over greater distances, indicating the unhindered diffusion in brain tissue (FIG. 8A). Based on the trajectories, the ensemble averaged MSD (<MSD>) over 1 second was calculated; PEG-PBAE presented significantly higher <MSD> in comparison to PBAE (FIG. 8B). The distribution of logarithmic MSD (log 10 MSD) of hundreds of individual gene vectors was also investigated. Defining rapidly moving gene vectors by log 10 MSD≥-1, 65% of PEG-PBAE could rapidly penetrate the brain in comparison to only 19% of PBAE (FIG. 8C).
Diffusion of Nanoparticles in Brain Tumor Tissue Gene vector diffusion was also studied in F98 glioblastoma tissue using similar techniques. Both gene vectors diffused more rapidly in tumor tissue in comparison to non-tumor tissue. However, PEG-PBAE achieved significantly higher tumor penetration in comparison to PBAE gene vectors (FIGS. 9A-9C).

Convection Enhanced Delivery

Figure 10A:
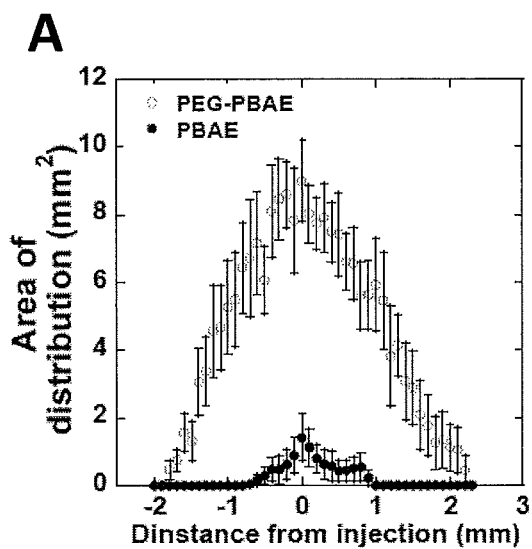
FIG. 10A is a graph showing area of distribution ($mm^2$) of gene vectors as a function of distance from injection site (mm) for PBAE (●) and PBAE-PEG (○) respectively following CED, averaged from at least n=4. Error bars represent standard error in mean.
Figure 10B:
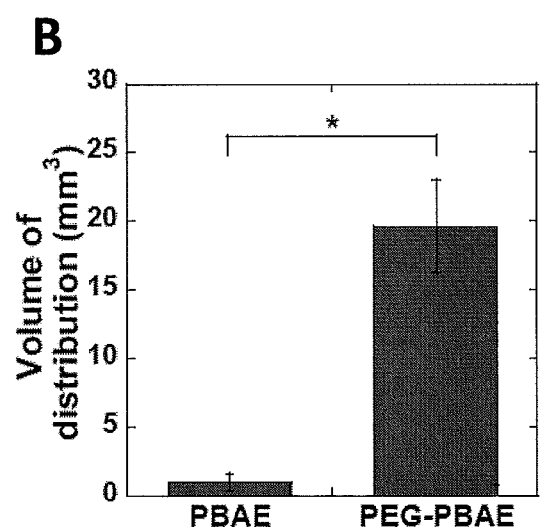
FIG. 10B is a histogram showing volume of distribution of gene vectors ($mm^3$) for PBAE and PEG-PBAE, respectively. * Denotes statistical significance, P value<0.01.

The gene vectors were also administered in the rodent striatum using convection enhanced delivery (CED). Following co-administration of PBAE and PEG-PBAE, PBAE were confined in the injection site while PEG-PBAE rapidly and homogeneously distributed through the entire striatum. The two gene vectors were separately administered and the area and volume of distribution were compared. Within the coronal plane of injection, PEG-PBAE covered a 6.3-fold larger area than PBAE did (FIG. 10A) and the difference in distribution was statistically significant (p<0.05). Moreover, the overall volume of distribution of PEG-PBAE was calculated to be 22-fold higher than for PBAE (FIG. 10B). This observation was also demonstrated by 3D reconstruction of the gene vector distribution.

Figure 10C:
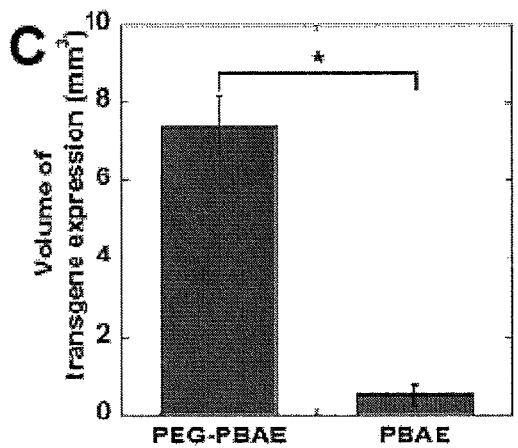
FIG. 10C is a histogram showing volume of transgene expression ($mm^3$) of gene vectors for PEG-PBAE and PBAE, respectively. *p<0.05 (n=3).
Figure 10D:
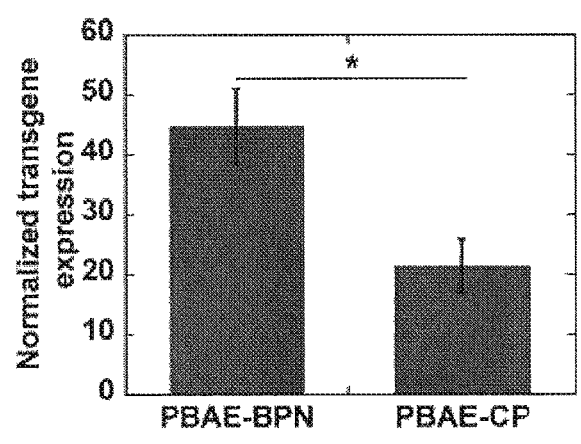
FIG. 10D is a bar graph showing normalized transgene expression following CED of PEG-PBAE (PBAE-BPN, PBAE-brain penetrating particles) and PBAE-CP in the rat striatum. The expression level of eGFP was normalized to a non-treated control brain. Data represents the mean±SEM (N=8 rats).

This difference resulted in a dramatic improvement in the distribution of transgene expression between PBAE and PEG-PBAE. PEG-PBAE were able to effectively transfect cells far from the injection site while PBAE resulted in transgene expression only in cells in the immediate vicinity to the injection site. In fact the volume of transfection was 13.9 fold higher for PEG-PBAE in comparison to PBAE (FIG. 10C). This observation can better be demonstrated using 3D reconstruction of the transfected cells. Also, PEG-PBAE (PBAE-BPN, PBAE-brain penetrating particles) provided 2-fold higher overall transgene expression compared to PBAE-CP (FIG. 10D). This is most likely due to the improved brain distribution of PBAE-BPN that allowed for transgene delivery in greater number of cells compared to PBAE-CP. This finding underscores that in vitro screening alone is limited in nature and the effects of extracellular environments must be factored in for the development of synthetic gene vectors for in vivo and ultimately clinical applications.

Figure 11A:
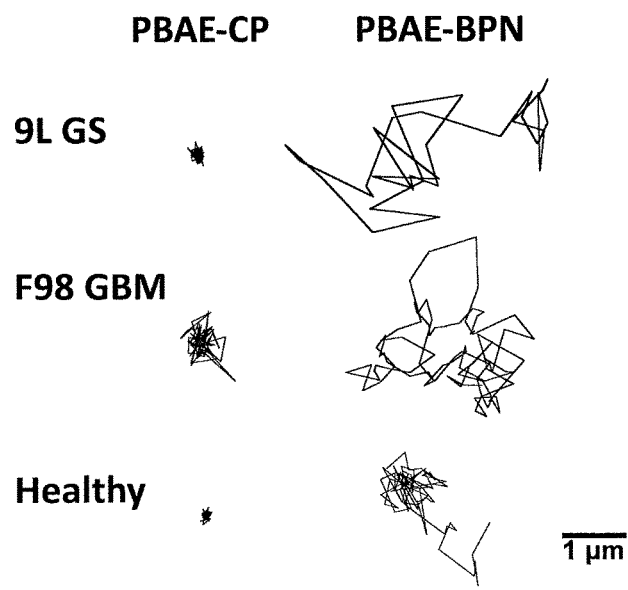
FIG. 11A shows a schematic of representative particle trajectories over 4.5 sec for gene vectors in ex vivo rodent brain (healthy) and brain tumor (F98 GBM and 9L GS) tissues.
Figure 11B:
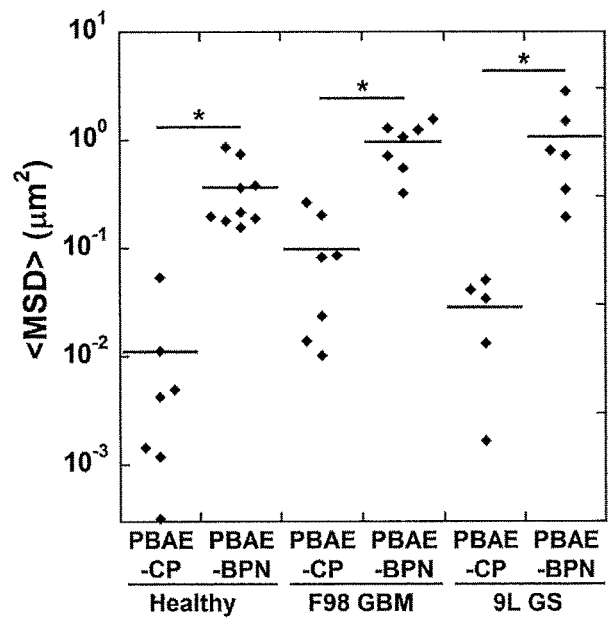
FIG. 11B is a dot plot showing the geometric mean of mean square displacements (MSD) of gene vectors in ex vivo rodent brain at time scale of 1 sec with with N≥500 particles tracked for each experiment.
Figure 12A:
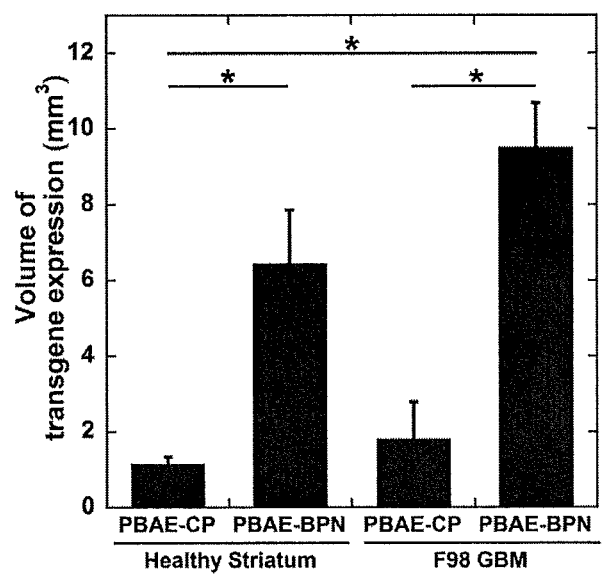
FIG. 12A is a bar graph showing image-based MATLAB quantification of volume of distribution of eGFP transgene expression ($mm^3$) in healthy rodent striatum and orthotropic F98 tumor. Data represents the mean±SEM. *p<0.05 (n=4-6).
Figure 12B:
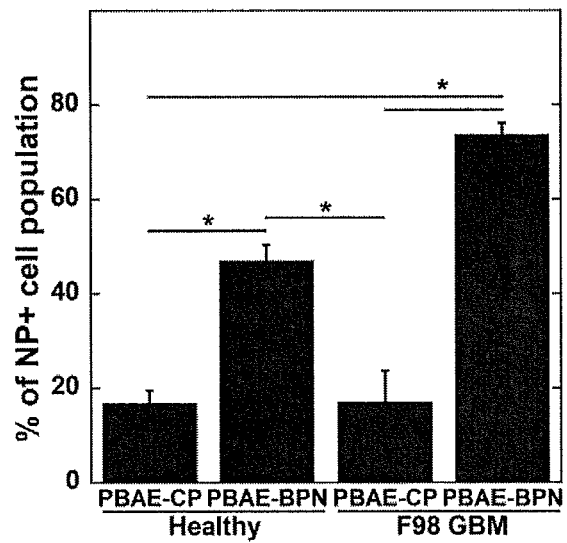
FIG. 12B is a bar graph showing percentage of nanoparticle positive (NP+) cell population following CED in healthy striatum and orthotopic F98 tumor.
Figure 12C:
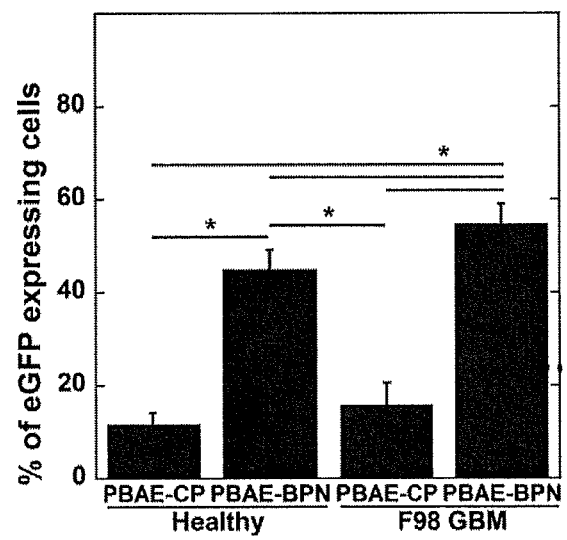
FIG. 12C is a bar graph showing percentage of eGFP-expressing cells following CED in healthy striatum and orthotopic F98 tumor.
Figure 12D:
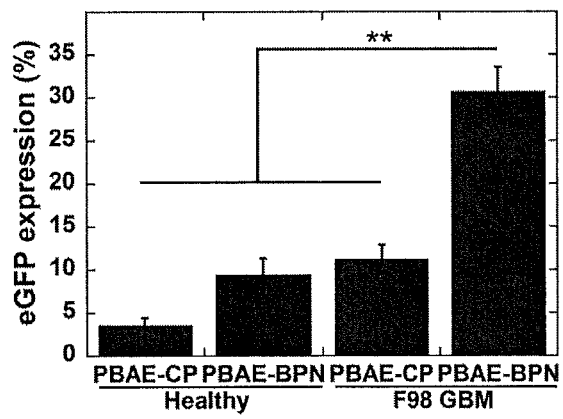
FIG. 12D is a bar graph showing normalized eGFP transgene expression (%) following CED administration of gene vectors in the healthy rodent striatum and F98 tumor. eGFP expression was analyzed using Western blot. The expression level of GFP was normalized to a non-treated control brain and GAPDH. Data represents the mean±SEM (n=8). Data represents the mean±SEM. ** Denotes statistically significant difference p<0.01.
Figure 12E:
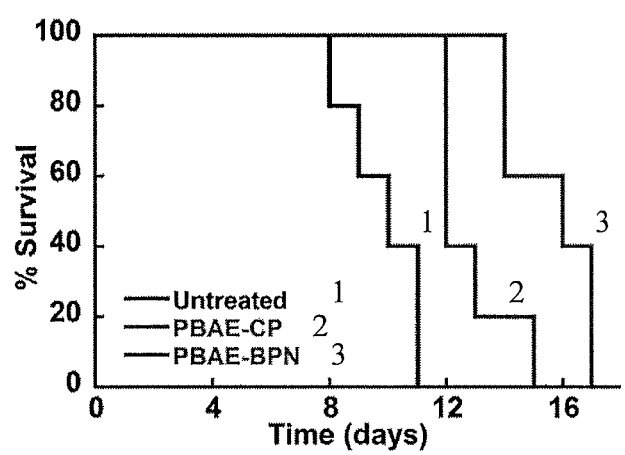
FIG. 12E is a Kaplan-Meier survival curve showing an orthotopic F98 glioblastoma model following CED treatment with PBAE-CP and PBAE-BPN pTK gene carriers and intravenous ganciclovir (IV GCV). Log-rank test demonstrates statistically significant difference in median survival between the three groups.
Figure 13A:
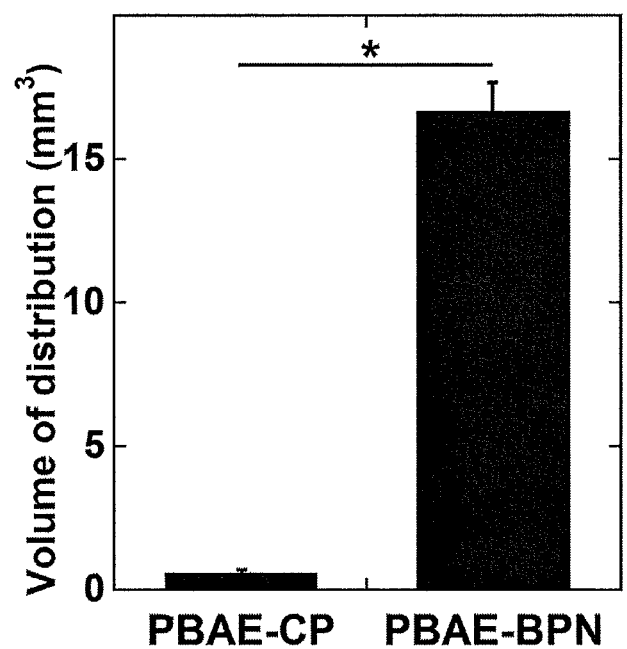
FIG. 13A is a bar graph showing an image based MATLAB quantification of volume of distribution for PBAE-CP and PBAE-BPN following CED for at least n=3 mice treated with PBAE-based gene vectors carrying a p53 expressing plasmid. * Denotes statistical significance P<0.01.
Figure 13B:
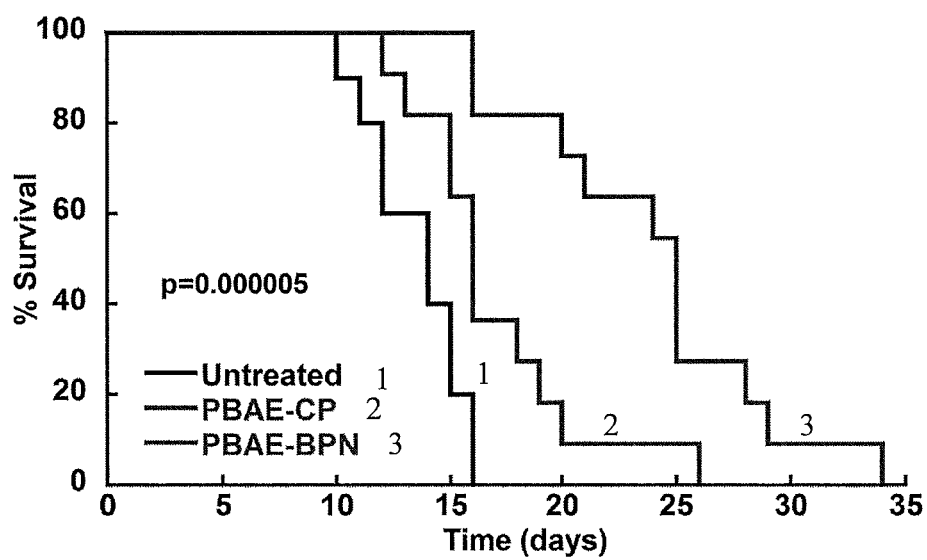
FIG. 13B is a Kaplan-Meier survival curve of an orthotopic 9L GS model following CED treatment with PBAE-CP and PBAE-BPN p53. Log-rank test demonstrates statistically significant difference in median survival between PBAE-BPN treated group and the other two groups.
Figure 14:
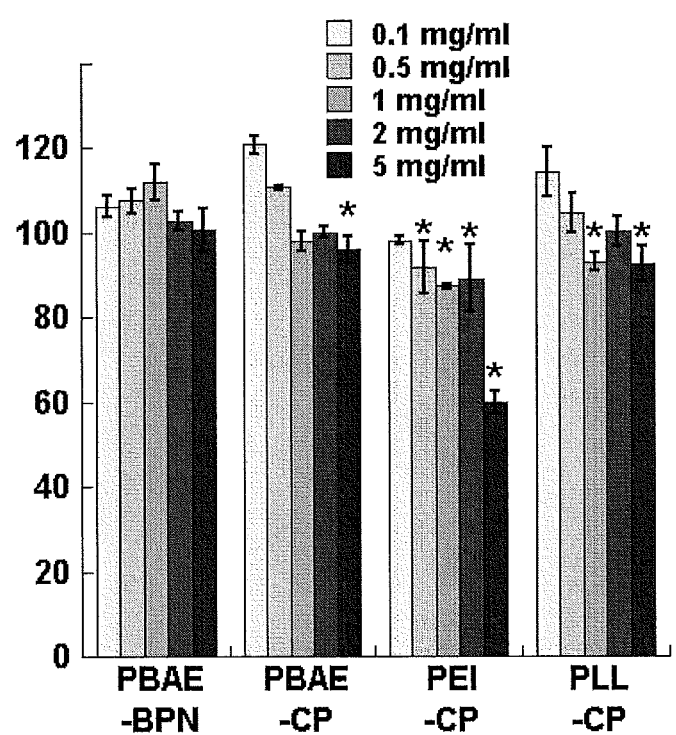
FIG. 14 is a bar graph showing the safety profile of PBAE-BPN. HT22 hippocampal neuronal cells were treated with varying concentrations of PBAE-BPN and conventional gene vectors (PBAE-CP, PEI-CP and PLL-CP). Cell viability was measured after 24 h of incubation and compared to untreated controls. Data are represented as mean±SEM. *Denotes statistically significant difference from 100% viability (p<0.05).

Example 4: PEG-PBAE Gene Vectors Provide High Level and Widespread Gene Transfer to Brain Tumors The diffusion of PBAE-based gene vectors ex vivo in healthy brain parenchyma and brain tumors is presented in FIGS. 11A and 11B. PBAE-brain penetrating nanoparticles (PBAE-BPN) showed significantly greater diffusion in the tissues when compared to conventional particles (PBA-CP). PBAE-BPN gene vectors showed greater percentage of transgene expression in healthy brain and brain tumors (FIGS. 12A-12D). The therapeutic effect of PBAE-BPN carrying pTK gene was significantly greater over no treatment, or treatment with PBAE-CP (FIG. 12E). Similarly, the therapeutic effect of PBAE-BPN carrying p53 gene was significantly greater over no treatment, or treatment with PBAE-CP (FIG. 13B). The PBAE-based gene vectors disclosed herein are safe on neuronal cells, as demonstrated by the cell viability assay performed on HT22 hippocampal neuronal cells (FIG. 14). The viability of HT22 cells was unaltered when incubated with up to 5 mg/ml PBAE-BPN for 24 hours.

Figure 15:
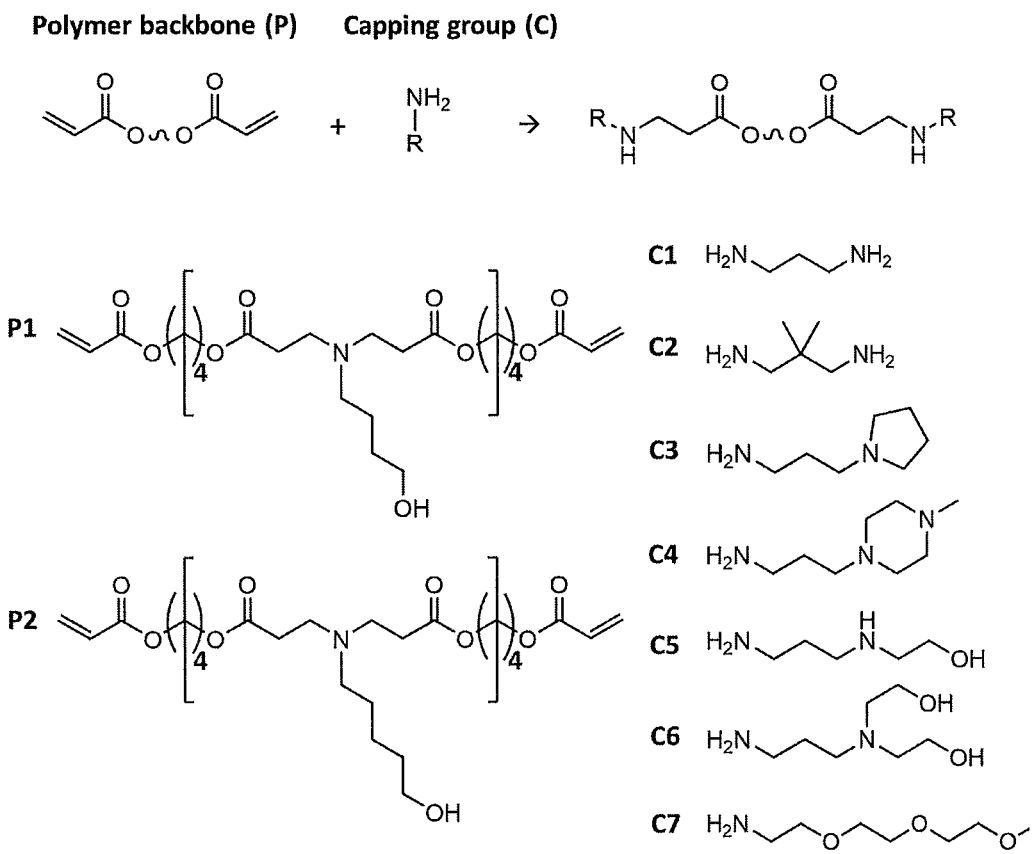
FIG. 15 is a schematic of the PBAE polymer library design.
Figure 17A:
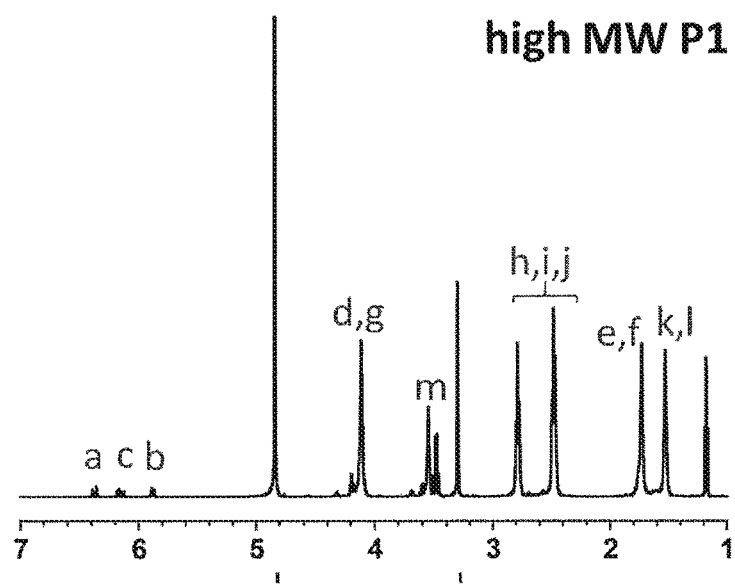
FIGS. 17A-17E are $^1$H NMR spectra of respective PBAE polymers and intermediates indicated in FIGS. 15 and 16.
Figure 17B:
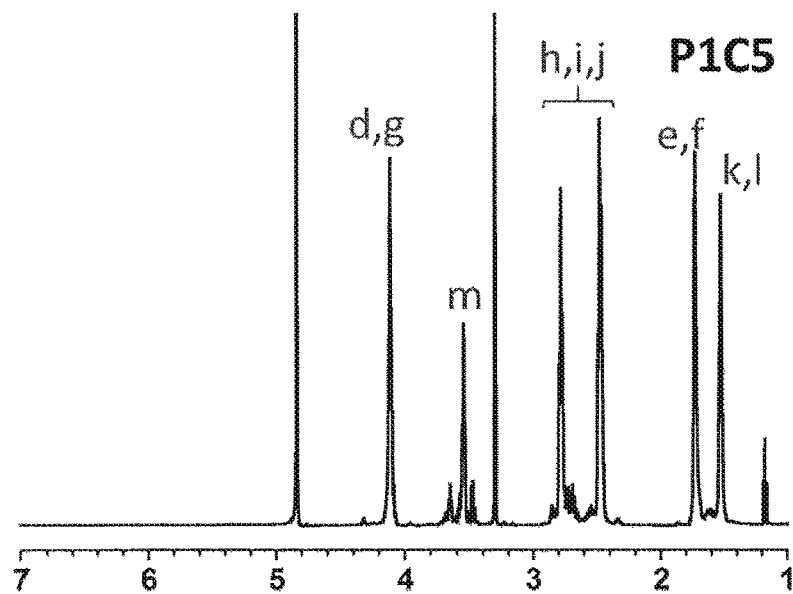
Figure 17C:
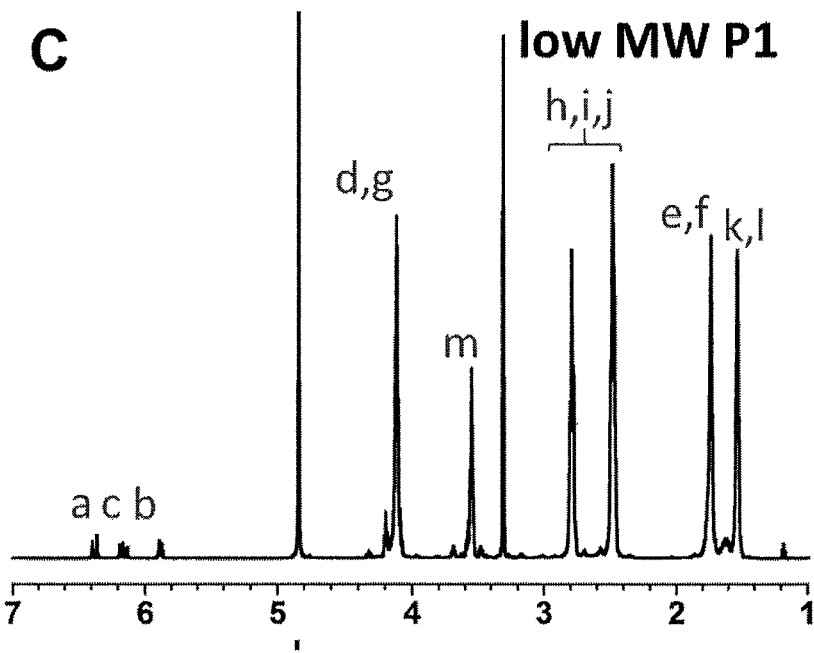
Figure 17D:
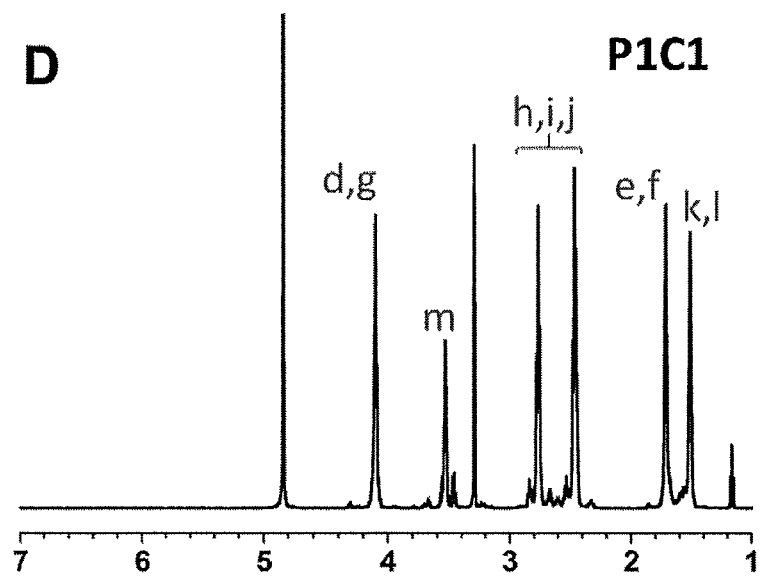
Figure 17E:
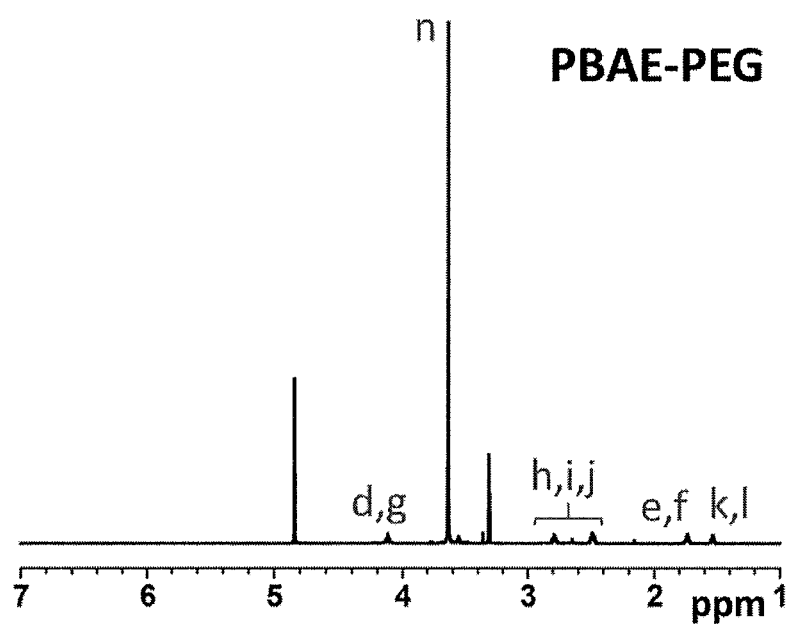

Example 5: Structure PBAE Polymer Library and Physicochemical Properties of PBAE Particles Formulated with Various Core Polymers The chemical structures of the PBAE polymers used herein are presented in FIGS. 15 and 16. Uncapped PBAE polymers were synthesized by a Michael addition reaction of diacrylates (1, 4-butanediol diacrylate) and amine alcohols (4-amino-1-butanol or 5-amino-1-pentanol) to yield P1 and P2. Subsequently, uncapped PBAE polymers were capped with one of the C1-C7 capping groups. FIGS. 17A-17E demonstrate the $^1$H NMR spectra of respective PBAE polymers and intermediates.

The physicochemical properties of the PBAE-PEG particles formulated with various core polymers from the PBAE polymer library are presented in Table 5. Physicochemical properties of the conventional particles generated from PEI or PLL (PEI-CP or PLL-CP) are presented in Table 6.

TABLE 5

Physicochemical properties of the PBAE-PEG particles.

| PBAE Polymer | Hydrodynamic Diameter ± SEM (nm) | PDI | ζ-potential ± SEM (mV) |
| --- | --- | --- | --- |
| P1C1 | 50 ± 0.9 | 0.1 | 1.1 ± 0.6 |
| P1C2 | 47 ± 0.6 | 0.2 | 1.9 ± 1.1 |
| P1C3 | 59 ± 1.0 | 0.1 | −0.9 ± 0.3 |
| P1C4 | 57 ± 4.0 | 0.1 | 2.3 ± 1.2 |
| P1C5 | 51 ± 0.3 | 0.1 | 1.9 ± 0.4 |
| P1C6 | 58 ± 2.0 | 0.1 | 2.7 ± 1.3 |
| P1C7 | 57 ± 1.0 | 0.1 | 1.2 ± 1.9 |
| P2C1 | 46 ± 1.9 | 0.1 | −0.3 ± 0.6 |
| P2C2 | 50 ± 3.5 | 0.3 | 14 ± 0.7 |
| P2C3 | 57 ± 10.6 | 0.2 | 6.9 ± 0.6 |
| P2C4 | 45 ± 0.2 | 0.3 | 3.8 ± 0.5 |
| P2C5 | 55 ± 2.3 | 0.2 | 1.6 ± 1.8 |
| P2C6 | 49 ± 6.8 | 0.3 | −0.7 ± 10.2 |
| P2C7 | 44 ± 0.3 | 0.1 | 0.3 ± 0.4 |

TABLE 6

Physicochemical properties of PEI-CP and PLL-CP particles.

| | Hydrodynamic Diameter ± SEM (nm)$^a$ | PDI$^a$ | ζ-potential ± SEM (mV)$^b$ |
| --- | --- | --- | --- |
| PEI-CP | 42 ± 1.0 | 0.2 | 27 ± 1.4 |
| PLL-CP | 47 ± 3.4 | 0.3 | 0.9 ± 1.6 |

$^a$Hydrodynamic diameter and PDI were measured by dynamic light scattering (DLS) in water (pH 7.0). Data represents mean ± SEM (n ≥ 3).
$^b$ζ-potential was measured by laser Doppler anemometry in 10 mM NaCl (pH 7.0). Data represents mean ± SEM (n ≥ 3).

We claim:

1. A method of making nanoparticles densely coated with a hydrophilic, neutrally charged polymer, for the delivery of nucleic acids across biological barriers, comprising
    blending polymer comprising poly (β-amino ester) (PBAE) and polymer comprising PBAE conjugated to a hydrophilic, neutrally charged polymer comprising polyethylene glycol or a copolymer thereof, to form a polymer blend wherein the molar ratio of the polymer comprising PBAE to the polymer comprising PBAE conjugated polyethylene glycol or a copolymer thereof is between 25 and 1 and yields colloidally stable nanoparticles with a hydrodynamic diameter less than 100 nm and a near neutral surface charge;
    adding nucleic acid to the blended polymer, wherein up to 10 volumes of nucleic acid are added to one volume of the blended polymer at a steady rate of up to 10 ml/min, and wherein the mass ratio of the nucleic acid to the blended polymer is altered to produce colloidally stable nanoparticles with a hydrodynamic diameter less than 100 nm and a near neutral surface charge; and
    purifying the nanoparticles.

2. The method of claim 1, wherein the first polymer is poly (β-amino ester) polymer.

3. The method of claim 1, wherein the mass ratio of the PBAE polymer to the nucleic acid is up to 100.

4. The method of claim 3, wherein the mass ratio of the PBAE polymer to the nucleic acid is about 60.

5. The method of claim 1, wherein the concentration of the blended polymer is up to 2,000 times the concentration of the nucleic acid in their respective solutions.

6. The method of claim 5, wherein the concentration of the blended polymer is about 300 times the preferred nucleic acid concentration of 0.1 mg/ml.

7. The method of claim 1 wherein the nucleic acid is added to the blended polymer at a rate of about 1 ml/min.

* * * * *